United States Patent
Austin et al.

(10) Patent No.: US 11,802,312 B2
(45) Date of Patent: Oct. 31, 2023

(54) DEVICES AND METHODS FOR MULTI-DIMENSIONAL GENOME ANALYSIS

(71) Applicants: Dimension Genomics Inc, San Diego, CA (US); DIMENSIONGEN, Grand Cayman (KY)

(72) Inventors: Michael David Austin, San Diego, CA (US); William Ridgeway, Encinitas, CA (US)

(73) Assignees: Dimension Genomics Inc.; DIMENSIONGEN, Grand Cayman (KY)

(*) Notice: Subject to any disclaimer, the term of this patent is extended or adjusted under 35 U.S.C. 154(b) by 0 days.

(21) Appl. No.: 17/997,174

(22) PCT Filed: Aug. 9, 2021

(86) PCT No.: PCT/US2021/045155
§ 371 (c)(1),
(2) Date: Oct. 26, 2022

(87) PCT Pub. No.: WO2022/035729
PCT Pub. Date: Feb. 17, 2022

(65) Prior Publication Data
US 2023/0193382 A1    Jun. 22, 2023

Related U.S. Application Data

(60) Provisional application No. 63/087,131, filed on Oct. 2, 2020, provisional application No. 63/063,728, filed on Aug. 10, 2020.

(51) Int. Cl.
C12Q 1/68        (2018.01)
C12Q 1/6874    (2018.01)
C12Q 1/6806    (2018.01)

(52) U.S. Cl.
CPC ........ *C12Q 1/6874* (2013.01); *C12Q 1/6806* (2013.01)

(58) Field of Classification Search
CPC ............................ C12Q 1/6813; C12Q 1/6869
See application file for complete search history.

(56) References Cited

U.S. PATENT DOCUMENTS 5,252,743 A    10/1993    Barrett et al.
5,451,683 A    9/1995    Barrett et al.
(Continued)

FOREIGN PATENT DOCUMENTS

WO        9718326        5/1997
WO        0073503        12/2000
(Continued)

OTHER PUBLICATIONS

Wen Jian et al, "Purification of Nucleic Acids in Microfluidic Devices", Analytical Chemistry, vol. 80, No. 17, Aug. 29, 2008, pp. 6472-6479.
(Continued)

*Primary Examiner* — Kenneth R Horlick
(74) *Attorney, Agent, or Firm* — Garrett H. Anderson

(57) ABSTRACT

A method of tracking proximity relationships is disclosed, comprising: (a) introducing a body into a solution of bio-molecule(s), said body comprising at least two capture probes, wherein each capture probe comprises a barcode and a capture domain, and at least one capture probe is a releasable capture probe, connected to the body via at least one cleavable linker; (b) allowing at least two capture probes to bind to their respective target bio-molecule(s) via their respective capture domains; and (c) releasing the at least one releasable capture probe from the body by cleaving its at least one cleavable linker.

20 Claims, 17 Drawing Sheets

(56) References Cited

U.S. PATENT DOCUMENTS

| | | | |
|---|---|---|---|
| 5,840,862 | A | 11/1998 | Bensimon et al. |
| 6,696,022 | B1 | 2/2004 | Chan et al. |
| 6,919,211 | B1 | 7/2005 | Fodor et al. |
| 6,955,915 | B2 | 10/2005 | Fodor et al. |
| 7,122,647 | B2 | 10/2006 | Bensimon et al. |
| 7,368,234 | B2 | 5/2008 | Bensimon et al. |
| 9,926,552 | B2 | 3/2018 | Craighead et al. |
| 10,106,848 | B2 | 10/2018 | Ramsey et al. |
| 10,434,512 | B2 | 10/2019 | Tegenfeldt et al. |
| 2003/0011901 | A1 | 1/2003 | Wayne et al. |
| 2014/0037834 | A1 | 2/2014 | Nottingham |
| 2014/0162271 | A1* | 6/2014 | Ramadass ............ C12Q 1/6806 435/6.12 |
| 2014/0378322 | A1 | 12/2014 | Hindson et al. |
| 2015/0037660 | A1 | 2/2015 | Bedjaoui et al. |
| 2016/0006062 | A1 | 1/2016 | Rechberger et al. |
| 2017/0027566 | A1 | 2/2017 | Moustafa |
| 2018/0216162 | A1 | 8/2018 | Belhocine et al. |
| 2019/0285644 | A1* | 9/2019 | Regev ................ C12N 15/1065 |
| 2020/0071746 | A1* | 3/2020 | Chen ....................... C40B 50/14 |

FOREIGN PATENT DOCUMENTS

| | | |
|---|---|---|
| WO | 2014164739 | 10/2014 |
| WO | 2015134785 | 9/2015 |
| WO | 2020047002 A1 | 3/2020 |
| WO | 2020047005 | 3/2020 |
| WO | 2020123301 A2 | 6/2020 |
| WO | 2020123305 | 6/2020 |
| WO | 2020176788 A1 | 9/2020 |
| WO | 2020198071 A1 | 10/2020 |
| WO | 2021059446 | 4/2021 |

OTHER PUBLICATIONS

Koo Hyung-Jun et al, "Design and characterization of hydrogel-based microfluidic devices with biomimetic solute transport networks", Biomicrofluidics, vol. 11, No. 2, Mar. 1, 2017, p. 024104.

Sheikhi Amir et al, "Modular microporous hydrogels formed from microgel beads with orthogonal thermo-chemical responsivity: Microfluidic fabrication and characterization", METHODSX, vol. 6, Jan. 1, 2019, pp. 1747-1752.

Annette Denker et al, "The second decade of 3C technologies: detailed insights into nuclear organization", Jan. 1, 2016, pp. 1357-1382.

Caló et al., "Biomedical Applications of Hydrogels: A Review of Patents and Commercial Products." European Polymer Journal 65 (2015): 252-67. https://doi.org/10.1016/j.eurpolymj.2014.11.024.

Casavant et al., "Suspended Microfluidics." Proceedings of the National Academy of Sciences of the United States of America 110, No. 25 (2013): 10111-16. https://doi.org/10.1073/pnas.1302566110.

Chan et al., "A Simple DNA Stretching Method for Fluorescence Imaging of Single DNA Molecules." Nucleic Acids Research 34, No. 17 (2006). https://doi.org/10.1093/nar/gkl593.

Conti et al., "Molecular Combing" (2001) Current Protocols in Cytometry John Wiley & Sons, Inc..

Cook et al., "The Effects of Secondary Structure and O2 on the Formation of Direct Strand Breaks upon UV Irradiation of 5-Bromodeoxyuridine-Containing Oligonucleotides." Chemistry and Biology 6, No. 7 (1999): 451-59. https://doi.org/10.1016/S1074-5521(99)80063-5.

Dai et al., "The Polymer Physics of Single DNA Confined in Nanochannels." Advances in Colloid and Interface Science 232 (2016): 80-100. https://doi.org/10.1016/j.cis.2015.12.002.

Dekker et al., Science 295, 1306-11, 2002.

Dixon et al., Nature 485, 376-80, 2012.

Doddridge et al., "UV-Induced Strand Break Damage in Single Stranded Bromodeoxyuridine-Containing DNA Oligonucleotides." Chemical Communications, No. 18 (1998): 1997-98. https://doi.org/10.1039/a804416c.

Dostie et al., Genome research 16, 1299-1309, 2006.

Dowen et al., Cell 159, 374-87, 2014.

Drouin et al., "High-Resolution R-Banding at the 1250-Band Level: III. Comparative Analysis of Morphologic and Dynamic R-Band Patterns (RHG and RBG)." Hereditas 114, No. 1 (Feb. 14, 2008): 65-77. https://doi.org/10.1111/j.1601-5223.1991.tb00554.x.

Du et al., "Intelligent Nucleic Acid Delivery Systems Based on Stimuli-Responsive Polymers." Soft Matter 6, No. 5 (2010): 835-48. https://doi.org/10.1039/B915020J.

Gačnin et al., "Biomedical Applications of DNA-Based Hydrogels." Advanced Functional Materials 30, No. 4 (Jan. 11, 2020): 1906253. https://doi.org/10.1002/adfm.201906253.

Gibb et al., "Single-Stranded DNA Curtains for Real-Time Single-Molecule Visualization of Protein-Nucleic Acid Interactions." Analytical Chemistry 84, No. 18 (2012): 7607-12. https://doi.org/10.1021/ac302117z.

Gueroui et al., "Observation by Fluorescence Microscopy of Transcription on Single Combed DNA." Proceedings of the National Academy of Sciences of the United States of America 99, No. 9 (2002): 6005-10. https://doi.org/10.1073/pnas.092561399.

He et al., "Preparation of Polymer Single Chain Nanoparticles Using Intramolecular Photodimerization of Coumarin." Soft Matter 7, No. 6 (2011): 2380. https://doi.org/10.1039/c0sm01383h.

Jerkovic et al., "Understanding 3D Genome Organization by Multidisciplinary Methods." Nature Reviews. Molecular Cell Biology 0123456789 (2021). https://doi.org/10.1038/s41580-021-00362-w.

Juncker et al., "Autonomous Microfluidic Capillary System." Analytical Chemistry 74, No. 24 (2002): 6139-44. https:// doi.org/10.1021/ac0261449.

Kempfer et al., "Methods for Mapping 3D Chromosome Architecture." Nature Reviews Genetics 21, No. 4 (2020): 207-26. https://doi.org/10.1038/s41576-019-0195-2.

Kloxin et al., "Photodegradable Hydrogels for Dynamic Tuning of Physical and Chemical Properties." Science 324, No. 5923 (Apr. 3, 2009): 59-63. https://doi.org/10.1126/science.1169494.

Koetting et al., "Stimulus-Responsive Hydrogels: Theory, Modern Advances, and Applications." Materials Science and Engineering: R: Reports 93 (Jul. 2015): 1-49. https://doi.org/10.1016/j.mser.2015.04.001.

Lawce et al., "Cytogenetics: An Overview." In The AGT Cytogenetics Laboratory Manual, edited by Marilyn S. Arsham, Margaret J. Barch, and Helen J. Lawce, 25-85. Hoboken, NJ, USA: John Wiley & Sons, Inc., 2017. https://doi.org/10.1002/9781119061199.ch2.

Lawce et al., "Peripheral blood cytogenetic methods." In The AGT Cytogenetics Laboratory Manual, edited by Marilyn S. Arsham, Margaret J. Barch, and Helen J. Lawce, 87-117. Hoboken, NJ, USA: John Wiley & Sons, Inc., 2017. https://doi.org/10.1002/9781119061199.ch3.

Lebofsky et al., "Single DNA Molecule Analysis: Applications of Molecular Combing." Briefings in Functional Genomics and Proteomics 1, No. 4 (2003): 385-96. https://doi.org/10.1093/bfgp/1.4.385.

Leriche et al., "Cleavable Linkers in Chemical Biology." Bioorganic and Medicinal Chemistry 20, No. 2 (2012): 571-82. https://doi.org/10.1016/j.bmc.2011.07.048.

Lieberman-Aiden et al., Science 326, 289-93, 2009.

Nguyen et al., "3D Mapping and Accelerated Super-Resolution Imaging of the Human Genome Using in Situ Sequencing." Nature Methods, 2020. https://doi.org/10.1038/s41592-020-0890-0.

Phillips-Cremins et al., Cell 153, 1281-95, 2013.

Pirrung et al., "A General Method for the Spatially Defined Immobilization of Biomolecules on Glass Surfaces Using 'Caged' Biotin." Bioconjugate Chemistry 7, No. 3 (1996): 317-21. https://doi.org/10.1021/bc960013v.

Rao et al, Cell 159, 1665-80, 2014.

Schurra et al., "Combing Genomic DNA for Structural and Functional Studies." The Nucleus: vol. 2: Chromatin, Transcription, Envelope, Proteins, Dynamics, and Imaging 464, No. Nov. 2008: 71. https://doi.org/10.1007/978-1-60327-461-6.

Shiroguchi et al., "Digital RNA Sequencing Minimizes Sequence-Dependent Bias and Amplification Noise with Optimized Single-Molecule Barcodes." Proceedings of the National Academy of Sciences of the United States of America 109, No. 4 (2012): 1347-52. https://doi.org/10.1073/pnas.1118018109.

(56) References Cited

OTHER PUBLICATIONS

Smith et al., "Highly-Multiplexed Barcode Sequencing: An Efficient Method for Parallel Analysis of Pooled Samples." Nucleic Acids Research 38, No. 13 (2010). https://doi.org/10.1093/nar/gkq368.
Stryer, L. "Fluorescence Energy Transfer as a Spectroscopic Ruler." Annual Review of Biochemistry 47, No. 1 (Jun. 1978): 819-46. https://doi.org/10.1146/annurev.bi.47.070178.004131.
Szabo et al., "Principles of Genome Folding into Topologically Associating Domains." Science Advances 5, No. 4 (2019). https://doi.org/10.1126/sciadv.aaw1668.
Tanyeri et al., "A Microfluidic-Based Hydrodynamic Trap: Design and Implementation." Lab on a Chip 11, No. 10 (2011): 1786-94. https://doi.org/10.1039/c0lc00709a.
Tøstesen et al., "Stitchprofiles.Uio.No: Analysis of Partly Melted DNA Conformations Using Stitch Profiles." Nucleic Acids Research 33, No. SUPPL. 2 (2005): 573-76. https://doi.org/10.1093/nar/gki424.
Volkmuth et al., "DNA Electrophoresis in Microlithographic Arrays." Nature 358, No. 6387 (1992): 600-602. https://doi.org/10.1038/358600a0.
Wang et al., "Single-Molecule Studies of Repressor-DNA Interactions Show Long-Range Interactions." Proceedings of the National Academy of Sciences of the United States of America 102, No. 28 (2005): 9796-9801. https://doi.org/10.1073/pnas.0502917102.
Wu et al., "On-Demand Removable Hydrogels Based on Photolabile Cross-Linkings as Wound Dressing Materials." Journal of Materials Chemistry B 7, No. 37 (2019): 5669-76. https://doi.org/10.1039/C9TB01544B.
Wu et al., "Resonance Energy Transfer: Methods and Applications." Analytical Biochemistry 218, No. 1 (Apr. 1994): 1-13. https://doi.org/10.1006/abio.1994.1134.
Zhang et al., "Preparation of Megabase-Sized DNA from a Variety of Organisms Using the Nuclei Method for Advanced Genomics Research." Nature Protocols 7, No. 3 (2012): 467-78. https://doi.org/10.1038/nprot.2011.455.
Zhao et al., Nat. Genet. 38, 1341-47, 2006.

\* cited by examiner

DEVICES AND METHODS FOR MULTI-DIMENSIONAL GENOME ANALYSIS

CROSS-REFERENCE TO RELATED APPLICATIONS

This document claims the benefit of priority to U.S. Provisional Application Ser. No. 63/063,728, filed Aug. 10, 2020, and to U.S. Provisional Application Ser. No. 63/087,131 filed Oct. 2, 2020 each of which is hereby incorporated by reference in its entirety.

BACKGROUND

It is well established that discrete and distant genomic sequence elements could regulate gene function over long distance (https://www.genome.gov/Funded-Programs-Projects/ENCODE-Project-ENCyclopedia-Of-DNA-Elements). In recent years, it has become evident that the spatial organization of the genome is key for its function. How genome regulates its functions is associated with not only the primary level of linear sequence information, but also physical configurations in which the genome resides. How sequence elements and other cellular components interact with each other in cis or trans in a spatial and temporal fashion impacts how they function. Mammalian genomes are spatially organized into subnuclear compartments, territories, high order folding complexes, topologically associating domains (TADs), and loops to facilitate gene regulation and other important chromosomal functions such as replications. These structures are likely a source for many aberrant genomic recombination and errors with pathological consequences or biological impacts. It has been proposed that chromosomal territories, compartments, topologically associating domains (TAD), chromatin loop and local direct regulatory factors binding, bending and kinks of the genomic DNA polymers are regulated in a complex and sophisticated manner involving many nuclear and cellular components such as transcription factors, repressors, insulators, transactivators and enzymes. How exactly these 3-dimensional territories, compartments, TADs, and loops are generated or regulated is still under intensive investigation and unclear. Technologies able to directly visualize and map these intricate dynamic interactions in their native genomic, subcellular and subnuclear context would be extremely valuable for understanding how the primary sequencing information links with the 3-D organization of the genome, and thus contribute to a better understanding and characterization of the regulation of genes and ultimately biological and pathophysiological functions and consequences.

Chromosome conformation capture (3C) approaches, referred to in this document as "proximity 3D mapping" (Dekker et al., Science 295, 1306-11, 2002; Zhao et al., Nat. Genet. 38, 1341-47, 2006; Dostie et al., Genome research 16, 1299-1309, 2006; Lieberman-Aiden et al., Science 326, 289-93, 2009) have been widely used to study chromatin organization in different species and cell types. These methods and their variations employ formaldehyde-mediated crosslinking followed by in-situ enzymatic digestion and proximity ligation to infer spatial relationships between genomic loci. They have been instrumental in elucidating the principles of chromatin folding. Studies using these techniques have confirmed the existence of multiple layers of genome organization such as chromosome territories, compartments (Lieberman-Aiden et al., Science 326, 289-93, 2009), topologically associating domains (TADs) (Dixon et al., Nature 485, 376-80, 2012), sub-TADs (Phillips-Cremins et al, Cell 153, 1281-95, 2013), insulated neighborhoods (Dowen et al., Cell 159, 374-87, 2014), and chromatin loops (Rao et al, Cell 159, 1665-80, 2014).

The vast majority of proximity 3D Mapping methods rely on formaldehyde-mediated crosslinking, which creates extensive covalent linkages of protein-protein and protein-DNA in chromatin. These crosslinks can mask certain restriction sites and prevent their full digestion. The ligation of partially digested fragments leads to an imprecise inference of their actual genomic proximity. New crosslinking strategies, which can ideally expose all potential restriction sites, are required to ubiquitously capture proximal contacts at all length scales. Furthermore, the existing methods are limited to capturing proximity information at specific moment in time, typically with minimal control over the nature of the precise time-point. Ideally, proximity information can be collected at a specific desired time point, and/or collected over a specific time-duration variation in proximity relationships within that time-duration monitored. In addition, digestion of a sample that comprises long nucleic acid molecules will likely preclude the ability to elucidate precise long-range structural variation information from the sample, especially if the sample originates from diverse pooled cells.

In addition to proximity 3D mapping methods, an additional set of 3D physical mapping methods, which includes the "super-resolution microscopy" methods [Jerkovic, 2021] have been developed to enable fluorescent interrogation of structural information of a sample in-situ, typically with multiplexing techniques that allow for parallel interrogation of multiple locations simultaneously, while maintaining the physical integrity of the sample, unlike the "proximity 3D mapping" methods that require digestion of the sample. However, such 3D physical mapping methods have limited capability of spatial and temporal analysis, if entirely with the fixed folded configuration. In addition, resolution of proximity relationships and multiplexing throughput is challenged by interrogating samples, such as metaphase chromosomes, that occupy small volumes (single microns) of 3D space.

There remains a need for additional compositions and methods for identifying and evaluating the physical proximity and structure of various molecular complexes and entities over a variety of specific time-points and time-durations, while maintaining the long-range integrity of the sample. Here we present new devices and methods to dynamically interrogate and analyze long nucleic acid molecules and their associated higher order nucleic acid structures.

SUMMARY OF THE INVENTION

Provided herein are methods and devices for analyzing the higher order nucleic acid structure of a long nucleic acid molecule that include: (a) positioning at least a portion of a long nucleic acid molecule with a higher order structure within a slit channel of a microfluidic device such that at least portion of said portion can be elongated, (b) interrogating the dynamic state of the higher order structure.

Also provided herein are methods and devices for analyzing the dynamic higher order nucleic acid structure of a long nucleic acid molecule that include: (a) positioning at least a portion of a long nucleic acid molecule with a higher order structure within a slit channel of a microfluidic device such that at least portion of said portion can be elongated, (b) interrogating a physical map along said elongated portion and interrogating the higher order structure.

Also provided herein are methods and devices for analyzing the dynamic higher order nucleic acid structure of a long nucleic acid molecule that include: (a) positioning at least a portion of a long nucleic acid molecule with a higher order structure within a slit channel of a microfluidic device such that at least portion of said higher order structure can be elongated, (b) interrogating a physical map along said elongated portion and interrogating the higher order structure.

Also provided herein are methods and devices for analyzing the dynamic higher order nucleic acid structure of a long nucleic acid molecule that include: (a) fixing at least a portion of a long nucleic acid molecule with a higher order structure within a porous gel material; (b) exposing said structure to at least one reagent.

Also provided herein are methods and devices for analyzing the higher order nucleic acid structure of a long nucleic acid molecule that include: (a) swelling at least a portion of a long nucleic acid molecule by digesting or denaturing the proteins associated with said molecule (b) fixing at least a portion of said swollen long nucleic acid molecule with a higher order structure within a porous gel material; (c) exposing said structure to at least one reagent.

Also provided herein are methods for analyzing the higher order nucleic acid structure of a long nucleic acid molecule that include: (a) binding two labelling bodies that comprise a FRET pair, each to different locations on a long nucleic acid molecule that comprises a higher order nucleic acid structure; (b) interrogating and monitoring the FRET signal generated by the acceptor of the pair with an optical interrogation system.

Also provided herein are methods for analyzing the higher order nucleic acid structure of a long nucleic acid molecule that include: (a) binding two labelling bodies that comprise a FRET pair, each to different locations on different long nucleic acid molecules that each comprises a higher order nucleic acid structure; (b) interrogating and monitoring the FRET signal generated by the acceptor of the pair with an optical interrogation system.

Also provided here are methods for analyzing the higher order nucleic acid structure of a long nucleic acid molecule that include: (a) introducing a body in a solution of biomolecule(s), said body comprising at least two capture probes, wherein each capture probe comprises a barcode and a capture domain, and at least one capture probe is a releasable capture probe, connected to the body via at least one cleavable linker; (b) Allowing at least two capture probes to bind to their respective target bio-molecule(s) via their respective capture domains; (c) Releasing the at least one releasable capture probe from the body by cleaving its at least one cleavable linker.

The disclosure is further elucidated through reference to the following numbered aspects of the embodiments herein:

1. Aspects of the present disclosure include a fluidic device comprising an enclosed slit fluidic channel configured to accommodate a long nucleic acid molecule comprising at least one higher order nucleic acid structure when at least a portion of said molecule in an elongated state, and a fluorescent interrogation system configured to interrogate said long nucleic acid molecule.
2. The device of aspect 1, further comprising said long nucleic acid molecule. 3. The device of aspect 2, wherein the long nucleic acid molecule comprises at least one fluorescent labelling body. 4. The device of aspect 1, wherein the enclosed slit fluidic channel has a depth of less than 3 times the focal depth of the fluorescent interrogation system. 5. The device of aspect 1, wherein the enclosed slit fluidic channel has a depth of no more than 1 micron. 6. The device of aspect 1, wherein the enclosed slit fluidic channel has a depth of no more than 500 nm. 7. The device of aspect 1, wherein the enclosed slit fluidic channel has a depth of no more than 100 nm. 8. The device of aspect 1, wherein the enclosed slit fluidic channel has a depth of no more than 50 nm. 9. The device of aspect 1, wherein the enclosed slit fluidic channel has a depth of no more than 25 nm. 10. The device of aspect 2, wherein at least a portion of said molecule in an elongated state specifies a physical map. 11. The device of aspect 10, wherein said physical map is a linear physical map. 12. The device of aspect 10, wherein said physical map comprises fluorescent labelling bodies. 13. The device of aspect 2, wherein the structure is interrogated at a first time point and at a second time point. 14. The device of aspect 13, wherein interrogation at the first time point indicates a first physical conformation, and interrogation at the second time point indicates a second physical conformation. 15. The device of aspect 2, wherein the long nucleic acid molecule is exposed to a reagent while in the fluidic device before the interrogation 16. The device of aspect 2, wherein the long nucleic acid molecule is exposed to a reagent while in the fluidic device during the interrogation. 17. The device of aspect 2, wherein the higher order nucleic acid structure correlates with a trait. 18. The device of aspect 2, wherein the higher order nucleic acid structure correlates with a condition. 19. The device of aspect 18, wherein the condition is a disease. 20. The device of aspect 18, wherein interrogation of the state of the higher order nucleic acid structure at a first time point generates information related to the condition. 21. The device of aspect 20, wherein interrogation of the higher order nucleic acid structure at a second time point generates information related to the condition. 22. The device of aspect 2, wherein the higher order nucleic acid structure comprises a nucleosome. 23. The device of aspect 2, wherein the higher order nucleic acid structure comprises a nucleosome clutch. 24. The device of aspect 2, wherein the higher order nucleic acid structure comprises chromatin. 25. The device of aspect 2, wherein the higher order nucleic acid structure comprises a chromatin nanodomain. 26. The device of aspect 2, wherein the higher order nucleic acid structure comprises a CCCTC binding factor. 27. The device of aspect 2, wherein the higher order nucleic acid structure comprises a loop. 28. The device of aspect 2, wherein the higher order nucleic acid structure comprises a topologically associating domain. 29. The device of aspect 2, wherein the higher order nucleic acid structure comprises a loop domain. 30. The device of aspect 2, wherein the higher order nucleic acid structure comprises a compartment A. 31. The device of aspect 2, wherein the higher order nucleic acid structure comprises a compartment B. 32. The device of aspect 2, wherein the higher order nucleic acid structure comprises an enhancer promoter complex. 33. The device of aspect 2, wherein the higher order nucleic acid structure comprises an insulator complex. 34. The device of aspect 2, wherein the higher order nucleic acid structure comprises a transcription factor complex. 35. The device of aspect 2, wherein the higher order nucleic acid structure comprises a CTCF protein. 36. The device of aspect 2, wherein the higher order nucleic acid structure comprises a PDS5 protein. 37. The device of aspect 2, wherein the higher order nucleic acid structure comprises a WAPL protein. 38. The device of aspect 2, wherein the higher order nucleic acid structure comprises heterochromatin. 39. The device of aspect 2, wherein the higher order nucleic acid structure comprises euchromatin. 40. The device of aspect 2, wherein the higher order nucleic acid structure comprises a heterochromatin-euchromatin boundary. 41. The device of aspect 2, wherein the higher order nucleic acid structure comprises a transcription factor. 42. The device of aspect 2, wherein the higher order nucleic acid structure comprises a methyl-binding protein. 43. The device of aspect 2, wherein the higher order nucleic acid structure comprises an exogenous nucleic acid genome integration complex. 44. The device of aspect 43, wherein the exogenous nucleic acid genome integration complex comprises a viral genome integration complex. 45. The device of aspect 43, wherein the exogenous nucleic acid genome integration complex comprises a recombinant nucleus acid. 46. The device of aspect 2, wherein the higher order nucleic acid structure comprises an extrachromosomal episome physical docking complex. 47. The device of aspect 46, wherein the extrachromosomal episome physical docking complex hosts a chromosome through at least one binding site. 48. The device of aspect 2, wherein the higher order nucleic acid structure comprises extrachromosomal nucleic acid deriving from a host chromosome.

49. Aspects of the present disclosure include a fluidic device comprising a fluidic channel comprising a porous gel capable of fixing at least a portion of a long nucleic acid molecule comprising at least one higher order nucleic acid structure, and at least one reagent.
50. The fluidic device of aspect 49, wherein a long nucleic acid molecule comprising at least one higher order nucleic acid structure has at least a portion of said molecule fixed in the porous gel. 51. The fluidic device of aspect 50, wherein the long nucleic acid molecule comprises at least one fluorescent labelling body. 52. The fluidic device of aspect 50, wherein the long nucleic acid molecule is interrogated by a fluorescent interrogation system. 53. The fluidic device of aspect 49, wherein a time point for fixing the long nucleic acid molecule to the gel is selected based on selection criteria. 54. The device of aspect 53, wherein the selection criteria of the time-point for fixing the long nucleic acid molecule is in reference to an event. 55. The device of aspect 54, wherein the event comprises an introduction of a reagent. 56. The device of aspect 54, wherein the event comprises a change in a particular environmental condition. 57. The device of aspect 54, wherein the event comprises the result of an analysis of an optical interrogation of said long nucleic acid molecule. 58. The device of aspect 54, wherein the event comprises identification of a state of cell in which said long nucleic acid molecule is contained. 59. The device of aspect 58, wherein the state is a particular point of a cell cycle. 60. The device of aspect 59, wherein the point of the cell cycle is interphase. 61. The device of aspect 59, wherein the point of the cell cycle is prophase. 62. The device of aspect 59, wherein the point of the cell cycle is prometaphase. 63. The device of aspect 59, wherein the point of the cell cycle is metaphase. 64. The device of aspect 59, wherein the point of the cell cycle is anaphase. 65. The device of aspect 59, wherein the point of the cell cycle is telophase. 66. The device of aspect 58, wherein the state is in a particular point of a cell life. 67. The device of aspect 66, wherein the particular point of a cell life is apoptosis. 68. The device of aspect 58, wherein the state exhibits a particular cell morphology. 69. The device of aspect 68, wherein the cell morphology comprises blebbing. 70. The device of aspect 68, wherein the cell morphology comprises plasmolysis. 71. The device of aspect 68, wherein the cell morphology comprises karyorrhexis. 72. The device of aspect 68, wherein the cell morphology comprises pyknosis. 73. The device of aspect 68, wherein the cell morphology comprises endocytosis. 74. The device of aspect 68, wherein the cell morphology comprises phagocytosis. 75. The device of aspect 68, wherein the cell morphology comprises viral budding. 76. The device of aspect 68, wherein the cell morphology comprises secreting lysis. 77. The device of aspect 66, wherein the cell is undergoing nucleic acid fragmentation. 78. The device of aspect 66, wherein the state is undergoing a certain enzymatic activity. 79. The device of aspect 78, wherein the enzymatic activity is transcription. 80. The device of aspect 55, wherein the reagent exposure is initiated before the fixing in the gel. 81. The device of aspect 49, wherein the long nucleic acid molecule is fixed in the gel prior to exposure to the reagent. 82. The device of aspect 49, wherein the long nucleic acid molecule is at least partially digested of proteins before being fixed. 83. The device of aspect 49, wherein the long nucleic acid molecule's proteins are at least partially denatured before being fixed. 84. The device of aspect 82, wherein the long nucleic acid molecule is a chromosome. 85. The device of aspect 82, wherein the long nucleic acid molecule has a physical conformation that exhibits swelling. 86. The device of aspect 85, wherein the swelling results in at least a two-fold increase in volume occupied within the fluidic device. 87. The device of aspect 49, wherein at least one processing step for proximity 3D mapping comprises use of the reagent. 88. The device of aspect 49, wherein at least one processing step for 3D physical mapping comprises use of the reagent. 89. The device of aspect 49, wherein at least a portion of the long nucleic acid molecule specifies a physical map that is interrogated. 90. The device of aspect 49, wherein the higher order nucleic acid structure correlates with a trait. 91. The device of aspect 49, wherein the higher order nucleic acid structure correlates with a condition. 92. The device of aspect 91, wherein the condition is a disease. 93. The device of aspect 91, wherein interrogation of the state of the higher order nucleic acid structure at a first time point generates information related to the condition. 94. The device of aspect 93, wherein interrogation of the higher order nucleic acid structure at a second time point, generates information related to the condition. 95. The device of aspect 49, wherein the higher order nucleic acid structure comprises a nucleosome. 96. The device of aspect 49, wherein the higher order nucleic acid structure comprises a nucleosome clutch. 97. The device of aspect 49, wherein the higher order nucleic acid structure comprises chromatin. 98. The device of aspect 49, wherein the higher order nucleic acid structure comprises a chromatin nanodomain. 99. The device of aspect 49, wherein the higher order nucleic acid structure comprises a CCCTC binding factor. 100. The device of aspect 49, wherein the higher order nucleic acid structure comprises a loop. 101. The device of aspect 49, wherein the higher order nucleic acid structure comprises a topologically associating domain. 102. The device of aspect 49, wherein the higher order nucleic acid structure comprises a loop domain. 103. The device of aspect 49, wherein the higher order nucleic acid structure comprises a compartment A. 104. The device of aspect 49 wherein the higher order nucleic acid structure comprises a compartment B. 105. The device of aspect 49, wherein the higher order nucleic acid structure comprises an enhancer promoter complex. 106. The device of aspect 49, wherein the higher order nucleic acid structure comprises an insulator complex. 107. The device of aspect 49, wherein the higher order nucleic acid structure comprises a transcription factor complex. 108. The device of aspect 49, wherein the higher order nucleic acid structure comprises a CTCF protein. 109. The device of aspect 49, wherein the higher order nucleic acid structure comprises a PDS5 protein. 110. The device of aspect 49, wherein the higher order nucleic acid structure comprises a WAPL protein. 111. The device of aspect 49, wherein the higher order nucleic acid structure comprises a heterochromatin, a euchromatin, or a heterochromatin-euchromatin boundary. 112. The device of aspect 49, wherein the higher order nucleic acid structure comprises a transcription factor. 113. The device of aspect 49, wherein the higher order nucleic acid structure comprises a methyl-binding protein. 114. The device of aspect 49, wherein the higher order nucleic acid structure comprises an exogenous nucleic acid genome integration complex. 115. The device of aspect 114, wherein the exogenous nucleic acid genome integration complex comprises viral genome integration complex. 116. The device of aspect 114, wherein the exogenous nucleic acid genome integration complex comprises a recombinant nucleic acid. 117. The device of aspect 49, wherein the higher order nucleic acid structure comprises an extrachromosomal episome physical docking complex. 118. The device of aspect 117, wherein the extrachromosomal episome physical docking complex hosts a chromosome through one or more binding sites. 119. The device of aspect 49, wherein the higher order nucleic acid structure comprises extrachromosomal nucleic acid deriving from a host chromosome.

120. Aspects of the present disclosure include a method of analyzing the proximity state of two regions, the first region bound by a first labelling body and located within a first nucleic acid molecule segment that comprises a higher order nucleic acid structure, and the second region bound by a second labelling body and located within a second nucleic acid molecule segment that comprises a higher order nucleic acid structure, and wherein the first and second labelling bodies together form a FRET pair, and wherein a fluorescent imaging interrogation system monitors and detects a fluorescent signal emitted by the acceptor of the pair.

121. The method of aspect 120, wherein the first nucleic acid molecule segment and the second nucleic acid molecule segment share a common phosphodiester backbone. 122. The method of aspect 120, wherein the monitoring comprises detecting a state of the fluorescent signal. 123. The method of aspect 122, wherein the state comprises duration of detection. 124. The method of aspect 122, wherein the state comprises signal magnitude. 125. The method of aspect 122, wherein the state comprises signal polarization. 126. The method of aspect 120, wherein a population of proximity pairs are simultaneously interrogated, and a population signal is determined. 127. The device of aspect 120, wherein the monitoring occurs over a time-period. 128. The device of aspect 127, wherein the time-period spans exposure to a reagent. 129. The device of aspect 127, wherein the time-period spans exposure to a particular environmental condition. 130. The device of aspect 127, wherein the time-period spans detection of a particular state of a cell, wherein the long nucleic acid molecule is contained in said cell. 131. The device of aspect 130, wherein the state is a particular point of a cell cycle. 132. The device of aspect 131, wherein the point of the cell cycle is interphase. 133. The device of aspect 131, wherein the point of the cell cycle is prophase. 134. The device of aspect 131, wherein the point of the cell cycle is prometaphase. 135. The device of aspect 131, wherein the point of the cell cycle is metaphase. 136. The device of aspect 131, wherein the point of the cell cycle is anaphase. 137. The device of aspect 131, wherein the point of the cell cycle is telophase. 138. The device of aspect 130, wherein the state is a particular point of a cell life. 139. The device of aspect 138, wherein the particular point is apoptosis. 140. The device of aspect 139, wherein the particular point comprises nucleic acid fragmentation. 141. The device of aspect 130, wherein the state exhibits a particular cell morphology. 142. The device of aspect 141, wherein the cell morphology comprises blebbing. 143. The device of aspect 141, wherein the cell morphology comprises plasmolysis. 144. The device of aspect 141, wherein the cell morphology comprises karyorrhexis. 145. The device of aspect 141, wherein the cell morphology comprises pyknosis. 146. The device of aspect 141, wherein the cell morphology comprises endocytosis. 147. The device of aspect 141, wherein the cell morphology comprises phagocytosis. 148. The device of aspect 141, wherein the cell morphology comprises viral budding. 149. The device of aspect 141, wherein the cell morphology comprises secreting lysis. 150. The device of aspect 130, wherein the state is undergoing a certain enzymatic activity. 151. The device of aspect 150, wherein the enzymatic activity is transcription. 152. The method of aspect 120, wherein the higher order nucleic acid structure is fluorescently interrogated in a microfluidic device. 153. The method of aspect 120, wherein at least a portion of at least one of the nucleic acid molecule segments is in an elongated state. 154. The device of aspect 120, wherein the higher order nucleic acid structure correlates with a trait. 155. The device of aspect 120, wherein the higher order nucleic acid structure correlates with a condition. 156. The device of aspect 155, wherein the condition is a disease. 157. The device of aspect 155, wherein interrogation of the state of the higher order nucleic acid at a first time point structure generates information related to the condition. 158. The device of aspect 156, wherein interrogation of the state of the higher order nucleic acid at a second time point generates information related to the condition. 159. The device of aspect 120, wherein interrogation of the state of the higher order nucleic acid structure generates information related to a disease. 160. The device of aspect 120, wherein interrogation of the dynamics of the higher order nucleic acid structure generates information related to a disease. 161. The device of aspect 120, wherein the higher order nucleic acid structure comprises a nucleosome. 162. The device of aspect 120, wherein the higher order nucleic acid structure comprises a nucleosome clutch. 163. The device of aspect 120, wherein the higher order nucleic acid structure comprises chromatin. 164. The device of aspect 120, wherein the higher order nucleic acid structure comprises a chromatin nanodomain. 165. The device of aspect 120, wherein the higher order nucleic acid structure comprises a CCCTC binding factor. 166. The device of aspect 120, wherein the higher order nucleic acid structure comprises a loop. 167. The device of aspect 120, wherein the higher order nucleic acid structure comprises a topologically associating domain. 168. The device of aspect 120, wherein the higher order nucleic acid structure comprises a loop domain. 169. The device of aspect 120, wherein the higher order nucleic acid structure comprises a compartment A. 170. The device of aspect 120, wherein the higher order nucleic acid structure comprises a compartment B. 171. The device of aspect 120, wherein the higher order nucleic acid structure comprises an enhancer promoter complex. 172. The device of aspect 120, wherein the higher order nucleic acid structure comprises an insulator complex. 173. The device of aspect 120, wherein the higher order nucleic acid structure comprises a transcription factor complex. 174. The device of aspect 120, wherein the higher order nucleic acid structure comprises a CTCF protein. 175. The device of aspect 120, wherein the higher order nucleic acid structure comprises a PDS5 protein. 176. The device of aspect 120, wherein the higher order nucleic acid structure comprises a WAPL protein. 177. The device of aspect 120, wherein the higher order nucleic acid structure comprises a heterochromatin, a euchromatin, or a heterochromatin-euchromatin boundary. 178. The device of aspect 120, wherein the higher order nucleic acid structure comprises a transcription factor. 179. The device of aspect 120, wherein the higher order nucleic acid structure comprises a methyl-binding protein. 180. The device of aspect 120, wherein the higher order nucleic acid structure comprises an exogenous nucleic acid genome integration complex. 181. The device of aspect 180, wherein the exogenous nucleic acid genome integration complex comprises viral genome integration complex. 182. The device of aspect 180, wherein the exogenous nucleic acid genome integration complex comprises a recombinant nucleus acid. 183. The device of aspect 120, wherein the higher order nucleic acid structure comprises an extrachromosomal episome physical docking complex. 184. The device of aspect 183, wherein the extrachromosomal episome physical docking complex hosts a chromosome through one or more binding sites. 185. The device of aspect 120, wherein the higher order nucleic acid structure comprises extrachromosomal nucleic acid deriving from a host chromosome.

186. Aspects of the present disclosure include a method of tracking proximity relationships comprising: (a) Introducing a body into a solution of bio-molecule(s), said body comprising at least two capture probes, wherein each capture probe comprises a barcode and a capture domain, and at least one capture probe is a releasable capture probe, connected to the body via at least one cleavable linker; (b) Allowing at least two capture probes to bind to their respective target bio-molecule(s) via their respective capture domains; (c) Releasing the at least one releasable capture probe from the body by cleaving its at least one cleavable linker. 187. The method of aspect 186, wherein a single bio-molecule is bound by at least one capture domain. 188. The method of aspect 186, wherein a single bio-molecule is bound by at least two capture domains. 189. The method of aspect 186, wherein at least one capture domain within the body non-specifically binds to a nucleic acid. 190. The method of aspect 186, wherein at least one capture domain within the body specifically binds to a nucleic acid having a specific nucleic acid sequence. 191. The method of aspect 186, wherein at least one capture domain within the body specifically binds to a specific protein. 192. The method of aspect 186, wherein at least one capture domain within the body non-specifically binds to a protein. 193. The method of aspect 186, wherein at least one capture domain within the body binds to an available target bio-molecule when subjected to activation. 194. The method of aspect 193, wherein the activation comprises photo activation. 195. The method of aspect 186, wherein the barcodes belong to a relationship set. 196. The method of aspect 195, wherein the relationship set comprises identical barcodes. 197. The method of aspect 195, wherein each body has a unique relationship set of barcodes. 198. The method of aspect 195, wherein the relationship set comprises relationship sub-sets. 199. The method of aspect 198, wherein a relationship sub-set is used to identify a type of capture domain(s). 200. The method of aspect 198, wherein a relationship sub-set identifies a type of target bio-molecule(s). 201. The method of aspect 198, wherein a relationship sub-set identifies a physical location of the capture domain in the body relative to a second capture domain. 202. The method of aspect 186, wherein at least one capture domain is caged by a photolabile protecting group. 203. The method of aspect 202, wherein the photolabile protecting group is degraded by exposure to a wavelength of light. 204. The method of aspect 186, wherein the body comprises a photo cleavable linker. 205. The method of aspect 186, wherein the body comprises a first photocleavable linker vulnerable to cleavage by a first light wavelength and a second photocleavable linker vulnerable to cleavage by a second light wavelength. 206. The method of aspect 186, wherein the body comprises a cleavable linker that is enzymatically cleavable. 207. The method of aspect 186, wherein the body comprises a cleavable linker that is thermally cleavable. 208. The method of aspect 186, wherein the body comprises a cleavable linker that is chemically cleavable. 209. The method of aspect 186, wherein at least one capture probe from a first body binds to the bio-molecule, and at least one capture probe from a second body also binds to the same bio-molecule. 210. The method of aspect 186, wherein at least one releasable capture probe from a first body binds to the bio-molecule, and after said releasable capture probe is released from the first body, at least one capture probe from a second body also binds to said bio-molecule. 211. The method of aspect 186, wherein the body comprises a bead, to which all capture probes are connected to through cleavable linkers. 212. The method of aspect 211, wherein the bead is a dendrimer. 213. The method of aspect 211, wherein the bead is a nano particle. 214. The method of aspect 211, wherein the bead has a size that is selected based on the desired spatial volume of proximity relationships to be tracked. 215. The method of aspect 211, wherein the size of the bead is at least 5 nm. 216. The method of aspect 211, wherein the size of the bead is at least 10 nm. 217. The method of aspect 211, wherein the size of the bead is at least 25 nm. 218. The method of aspect 211, wherein the size of the bead is at least 100 nm. 219. The method of aspect 211, wherein the size of the bead is at least 500 nm. 220. The method of aspect 211, wherein the bead exhibits a fluorescent property. 221. The method of aspect 211, wherein the bead exhibits a Photoluminescence property. 222. The method of aspect 211, wherein the bead exhibits a magnetic property. 223. The method of aspect 186, wherein the at least one bound bio-molecule is a long nucleic acid molecule. 224. The method of aspect 223, wherein said long nucleic acid molecule comprises a higher order nucleic acid structure. 225. The method of aspect 223, wherein at least a portion of the long nucleic acid molecule is further processed. 226. The method of aspect 225, wherein the long nucleic acid molecule is bound to a releasable capture domain. 227. The method of aspect 226, wherein the processing is performed after the release of the releasable-capture domain from the body. 228. The method of aspect 225, wherein the processing comprises combing. 229. The method of aspect 225, wherein the processing comprises elongating in a microfluidic device. 230. The method of aspect 225, wherein the processing comprises generating a physical map. 231. The method of aspect 225, wherein the processing comprises sequencing. 232. The method of aspect 225, wherein the processing comprises hybridization of a nucleic acid molecule. 233. The method of aspect 225, wherein the processing comprises binding of a fluorescent probe. 234. The method of aspect 225, wherein the processing comprises amplification of at least a portion a nucleic acid. 235. The method of aspect 225, wherein the processing comprises an enzymatic reaction. 236. The method of aspect 225, wherein the processing comprises ligation. 237. The method of aspect 225, wherein the processing comprises digestion using a restriction enzyme. 238. The method of aspect 225, wherein the processing comprises nicking using a nicking enzyme. 239. The method of aspect 225, wherein the processing comprises an incorporation of a nucleotide using a polymerase.
240. Aspects of the present disclosure include a method of assaying for higher order nucleic acid complex structure of a long nucleic acid, the method comprising positioning the higher order nucleic acid complex structure in a visualization region, determining a first physical map for at least a portion of the higher order nucleic acid complex, subjecting the higher order nucleic acid complex to a reaction, and determining a second physical map for the at least a portion of the higher order nucleic acid complex.
241. The method of aspect 240, wherein the reaction comprises partial degradation of the higher order nucleic acid complex. 242. The method of aspect 240, wherein the reaction comprises addition of an exogenous component to the higher order nucleic acid complex. 243. The method of aspect 240, comprising subjecting the higher order nucleic acid complex to a second reaction, and determining a third physical map for the at least a portion of the higher order nucleic acid complex. 244. The method of any one of aspects 240 or 243, wherein the long nucleic acid is not subjected to cleavage of a phosphodiester bond. All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

The terms used in this specification generally have their ordinary meanings in the art, within the context of the invention, and in the specific context where each term is used. Certain terms are discussed below, or elsewhere in the specification, to provide additional guidance to the practitioner in describing the devices and methods of the invention and how to make and use them. It will be appreciated that the same thing can typically be described in more than one way. Consequently, alternative language and synonyms may be used for any one or more of the terms discussed here. Synonyms for certain terms are provided. However, a recital of one or more synonyms does not exclude the use of other synonyms, nor is any special significance to be placed upon whether or not a term is elaborated or discussed herein. All publications, patent applications, patents, and other references mentioned herein are incorporated by reference. In the case of conflict, the present specification, including definitions, will control. In addition, the materials, methods, and examples are illustrative only and are not intended to be limiting.

The invention is also described by means of particular examples. However, the use of such examples anywhere in the specification, including examples of any terms discussed herein, is illustrative only and in no way limits the scope and meaning of the invention or of any exemplified term. Likewise, the invention is not limited to any particular embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF DRAWINGS

For all drawings, the use of roman numerals: i), ii), iii), iv), etc are to denote a passage of time. Unless specifically stated, the figures are not drawn to scale.

DETAILED DESCRIPTIONS

Definitions

Figure 1:
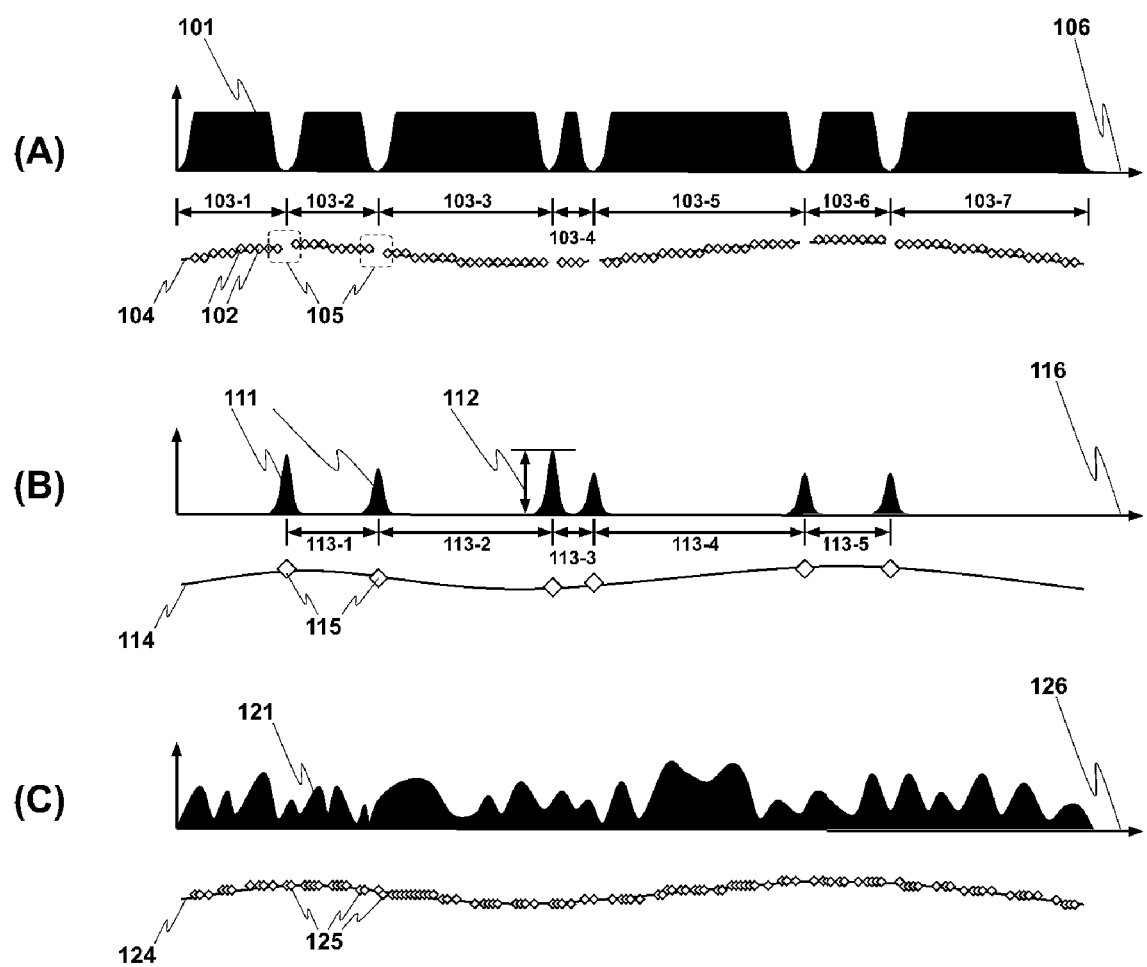
FIG. 1(A) demonstrates an embodiment of generating a linear physical map along the length of a long nucleic acid molecule by cleaving the molecule at known recognition sites producing an ordered pattern of lengths.
FIG. 1(B) demonstrates an embodiment of generating a linear physical map by attaching label bodies at known recognition sites producing an ordered pattern of segments.
FIG. 1(C) demonstrates an embodiment of generating a linear physical map by attaching label bodies along the length of molecule in a manner such the density of the labelling bodies correlates with the underlying AT/CG ratio FIG. 2 demonstrates an enclosed fluidic device and method for generating combed linearly elongated nucleic acid molecule in parallel fashion, with (i) showing the molecules being flown into an enclosed channel, and with (ii) showing said molecules after the roof is removed from the channel.

As used herein, "about" or "approximately" in the context of a number shall refer to a range spanning +/−10% of the number, or in the context of a range shall refer to an extended range spanning from 10% below the lower limit of the listed range to 10% above the listed upper limit of the range.

The use of the term "or" in the claims is used to mean "and/or" unless explicitly indicated to refer to alternatives only or the alternatives are mutually exclusive, although the disclosure supports a definition that refers to only alternatives and "and/or."

The words "a" and "an," when used in conjunction with the word "comprising" in the claims or specification, denotes one or more, unless specifically noted.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

The use of the term "combination" is used to mean a selection of items from a collection, such that the order of selection does not matter, and the selection of a null set (none), is also a valid selection when explicitly stated. For example, the unique combinations including the null of the set {A,B} that can be selected are: null, A, B, A and B.

Sample. The term "sample," as used herein, generally refers to a biological sample of a subject which at least partially contains nucleic acid originating from said subject. The biological sample may comprise any number of macromolecules, for example, cellular long nucleic acid molecules. The sample may be a cell sample. The sample may be a cell line or cell culture sample. The sample may be a CTC (circulating tumor cells) or CFC (circulating fetal cells) sample. The sample can include one or more cells. The sample may be one or more droplets containing a biological material. The sample can include one or more microbes. The biological sample may be a nucleic acid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

Nucleic Acid. The terms "nucleic acid", "nucleic acid molecule", "oligonucleotide" and "polynucleotide", "nucleic acid polymer", "nucleic acid fragment", "polymer" are used interchangeably and refer to a polymeric form of nucleotides of any length, either deoxyribonucleotides or ribonucleotides, or analogs thereof. The terms encompass, e.g., DNA, RNA and modified forms thereof. Polynucleotides may have any three-dimensional structure, and may perform any function, known or unknown. Non-limiting examples of polynucleotides include a gene, a gene fragment, exons, introns, messenger RNAs (mRNA), transfer RNAs, ribosomal RNAs, lncRNAs (Long noncoding RNAs), lincRNAs (long intergenic noncoding RNAs), ribozymes, cDNA, ecDNAs (extrachromosomal DNAs), artificial minichromosomes, cfDNAs (circulating free DNAs), ctDNAs (circulating tumor DNAs), cffDNAs (cell free fetal DNAs), recombinant polynucleotides, branched polynucleotides, plasmids, vectors, isolated DNA of any sequence, control regions, isolated RNA of any sequence, nucleic acid probes, and primers.

Unless specifically stated otherwise, the nucleic acid molecule can be single stranded, double stranded, or a mixture there-of. For example, there may be hairpin turns or loops. Unless specifically stated otherwise, the nucleic acid molecule may contain nicks.

Long Nucleic Acid. Unless specifically stated otherwise, a "long nucleic acid fragment" or "long nucleic acid molecule" is double strand nucleic acid of at least 1 kbp in length, and is thus a kind of macromolecule, and can span to an entire chromosome. It can originate from any source, man-made or natural, including single cell, a population of cells, droplets, an amplification process, etc. It can include nucleic acids that have additional structure such as structural proteins histones, and thus includes chromatin. It can include nucleic acid that has additional bodies bound to it, for example labelling bodies, DNA binding proteins, RNA.

Higher Order Nucleic Acid Structure. A "higher order nucleic acid structure", or "structure", or "higher order structure" refers to any 2nd, 3rd, or 4th order DNA structure, including any body bound to said nucleic acid molecule. The nucleic acid molecule may be linear or circular. Nucleic acids can have any of a variety of structural configurations, e.g., be single stranded, double stranded, triplex, replication loop or a combination of both, as well as having higher order intra- or inter-molecular secondary/tertiary/quaternary structures, e.g., chromosomal territories, chromosome boundaries, chromosome regions, compartments, Topologically Associating Domains (TAD), chromatin loop and local direct regulatory factors binding, condensing associated loops, cohesin associated loops, guide nucleic acid, argonaut complexes, CRISPR Cas9 complexes, nucleoprotein complexes, insulator complexes, enhancer-promoter complexes, ribonucleic acid (RNA), small interfering RNA (siRNA), micro RNA (miRNA), guide RNA (gRNA), long noncoding RNA (lncRNA), repeat region binding proteins, telomere modification proteins, nucleic acid repair proteins, regulatory factor binding proteins, nucleic acid binding proteins, proteins, histone deacetylase (HDAC), chromatin remodeling protein, methyl-binding protein, transcription factor transcription complexes, bending with kinks of the genomic DNA polymers such as hairpins, replication loops, triple stranded regions, in cis or trans fashion etc. The nucleotides within the nucleic acid may have any combination of epigenomic state including but not limited to such as methylation or acetylation states. The nucleic acid can originate from any source, man-made or natural, including single cell, a population of cells, droplets, an amplification process, etc. In some embodiments, these structures include compounds and/or interactions of nucleic acids and proteins. In some embodiments, these structures include 2D and 3D configurations of the nucleic acid beyond the linear 1D polymer chain. These 2D and 3D configurations can be formed via interactions with proteins, other nucleic acid molecules, or external boundary conditions. Non limiting examples of boundary conditions include a micro or nanofluidic chamber, a well on or in substrate or defined within a fluidic device, a droplet, a nucleus. The nucleic acid can include nucleic acids that has additional structure such as structural proteins including but not limited to such as any regulatory binding sites complexes, enhancer/transcription factor complex and their interaction with a nucleic acid molecule, Cohesins complex SMC (structural maintenance of chromosomes), ATPase subunits (Smc1 and Smc3), non-SMC regulatory subunits (Rad21/Scc1/Mcd1 and SA1/SA2/Scc3), Sgo1, mitotic kinases (pololike kinase 1 (Plk1) and aurora B), protein phosphatase 2A (PP2A), chromosome passenger complex (CPC), topo II decatenation, condesins, CTCF proteins, PDS5 proteins, WAPL proteins, condensin I, condensin II, CAP-G, histones and their derivative complexes, and thus includes chromatin. In some embodiments, higher order structure can include exogenous nuclei acid genome integration complex, in particular, an exogenous nuclei acid genome integration complex that comprises viral genome integration complexes or recombinant nucleus acid. In some embodiments, higher order structure can include extrachromosomal episomes physical docking complexes, in particular, where such complexes host chromosomes through binding sites. In some embodiments, the higher order nucleic acid structure comprises extrachromosomal nucleic acid deriving from a host chromosome. All of above, not limiting, could be target of labelling, physical or conformational biomarkers indicating the presence of certain state of genome organization or the shift between the states, that could be associated with pathogenomic consequences.

In particular, higher order nucleic acid structure can refer to the various levels of genome organization contained within a cell nucleus [Jerkovic, 2021], [Kempfer, 2020] either individually, collectively, or a sub-set there-of Such genomic organization starts with linear primary DNA winding around histones to form nucleosomes, which are organized into clutches, each containing ~1-2 kb of DNA. Nucleosome clutches form chromatin nanodomains (CNDs) ~100 kb in size, where most enhancer-promoter (E-P) contacts take place. At the scale of ~1 Mb, CNDs and CCCTC-binding factor (CTCF)—cohesin-dependent chromatin loops form topologically associating domains (TADs) and loop domains. On the higher scale up to 100s of megabases, chromatin segregates into gene-active and gene-inactive compartments (A and B, respectively) and into compartment-specific contact hubs, formation of sister chromatid axes. At the highest topological level, the nucleus is organized into chromosome territories.

Hybridization. As used herein, the terms "hybridization", "hybridizing," "hybridize," "annealing," and "anneal" are used interchangeably in reference to the pairing of complementary or substantially complementary nucleic acids. Hybridization and the strength of hybridization (i.e., the strength of the association between the nucleic acids) is influenced by such factors as the degree of complementary between the nucleic acids, stringency of the conditions involved, the Tm (melting temperature) of the formed hybrid, and environmental conditions. "Hybridization" methods involve the annealing of one nucleic acid to another, complementary nucleic acid, i.e., a nucleic acid having a complementary nucleotide sequence.

Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

In the context of this document, where hybridization occurs between nucleic acid strand and a double-stranded nucleic acid molecule, it should be understood that such hybridization is being done under conditions of either partial or full denaturation of the double-stranded nucleic acid molecule, unless otherwise specifically stated.

Labelling Body. A "labelling body" used herein is a physical body that can bind to a nucleic acid molecule, or to a body directly or indirectly bound to a nucleic acid molecule, which can be used to generate a signal that can be detected with interrogation, that differs from a detected signal (or lack there-of) that would be generated by said nucleic acid without said body. A labelling body may be a fluorescent intercalating dye that when bound to nucleic acid, can be used in a fluorescent imaging system to identify the presence of said nucleic acid. In another example, a labelling body may by a compound that binds specifically to methylated nucleotides, and gives a current blockade signal when transported through a nanopore, thus reporting a signal as to said molecule's methylation state. In another example, a fluorescent probe specifically hybridized to a sequence of a nucleic acid, thus providing confirmation with a fluorescent imaging system that the sequence is present on said nucleic acid. In another example, a fluorescent probe specifically binds to a specific protein (e.g.: DNA binding protein), with said protein bound to a long nucleic acid molecule. In some cases, the absence of the labelling body, is itself the signal. In some cases, the signal associated with the labelling body is an attenuation, blocking, displacement, quenching, or modification of a signal from another labelling body. Non-limiting examples include: binding of a dark labelling body to the nucleic acid to displace an existing bond fluorescent body; binding of a dark labelling body to the nucleic acid to block a fluorescent labelling body from binding; quenching a near-by fluorescent labelling body bond to a nucleic acid; directly, or indirectly, reacting with a fluorescent labelling body bond to a nucleic acid to reduce its fluorescence. In some cases, the labelling body is not physically attached to the nucleic molecule at the time of interrogating said nucleic molecule and labelling body. For example, a labelling body may be attached to a nucleic acid molecule via a cleavable linker. At the desired time, the linker is cleaved, releasing said labelling molecule which is then detected by interrogation.

Interrogation. "Interrogation" is a process of assessing the state of a nucleic acid, a long nucleic acid molecule, a higher order nucleic acid structure, a nucleic acid—protein complex, or other bio-molecule with an interrogation system. In some embodiments, the state of nucleic acid is assessed by interrogating the state of at least one labelling body on the nucleic acid by measuring a signal generated directly, or indirectly from the labelling body. It may be a binary assessment, such as the labelling body is present, or not. It may be quantitative, such as how many labelling bodies are present on a molecule. It may be a signal density or intensity along a line, an area, or volume. It may be a physical count, or distance between labelling bodies along the length the molecule.

In some embodiments, interrogation is used to generate an in-silico representation of a physical map.

In some embodiments, interrogation is used to assess the physical state of a higher order nucleic acid structure. The physical state of the structure being interrogated may comprise the topology of the molecule such as the presence of a loop structure, a set of hierarchical loop structures, the number of supercoils present in a loop or the degree to which one or more loops from the same or separate molecules are intertwined. The physical state of the structure being interrogated may comprise the accessibility of a region of the nucleic acid to a binding partner or a cis or trans acting factor. The physical state of the structure being interrogated may comprise the presence of partially replicated nucleic acid still in close proximity such as Okazaki fragments or a marker of newly synthesized nucleic acid such as results from a pulse of BrdU. The physical state of the structure being interrogated may comprise the level of cohesin left on metaphase chromosomes that has been manipulated experimentally or affected by genetic anomalies (e.g., by depleting either cohesin itself or Wapl), the resulting chromatids display substantially different lengths and shapes, becomes a quantitatively measurable biomarkers indicating of certain pathological states (Losada et al. 2005; Gandhi et al. 2006; Shintomi and Hirano 2009). The physical state of the structure being interrogated may comprise the amount, ratio, and distribution of condensins I and II in these chromatids. The physical state of structure being interrogated may comprise dynamic changes in genome organization, as in Cohesin release and sister chromatid resolution.

In some embodiments, the signal being interrogated may be fluorescent, photoluminescent, electro-magnetic, electrical, magnetic, physical, chemical, exhibit plasmon resonance or enhance raman signals by means of surface enhanced plasmon resonance.

The signal being interrogated may be analog or digital in nature. For example, the signal may be an analog density profile of the labelling body along the length of the nucleic acid in which the signal measured originates from multiple labelling bodies. In some embodiments, the state of the nucleic acid is directly interrogated without a labelling body, for example direct interrogation of long nucleic acid molecules in a cell via phase microscopy, or direct interrogation of nucleic acid via a current blockade nanopore. Non exhaustive examples of different interrogation methods that may be used an interrogation systems either separately, or in combination include fluorescent imaging, brightfield imaging, dark-field imaging, phase contrast imaging, epi-florescent imaging, total internal reflection fluorescence imaging, nearfield/evanescent field imaging, a wave guide, a zero mode waveguide, plasmonic signaling, confocal, scattering, light sheet, structured illumination, stimulated emission depletion, super resolution, stochastic activation super resolution, stochastic binding super resolution, multiphoton, nanopore sensing of a current, voltage, power, capacitive, inductive, or reactive signal (either column blockade through the pore, and tunneling across the pore), chemical sensing (eg: via a reaction), physical sensing (eg: interaction with a sensing probe), SEM, TEM, STM, SPM, AFM. In addition, combinations of different labelling bodies and interrogation methods are also possible. For example: fluorescent imaging of an intercalating dye on a nucleic acid, while translocating said nucleic acid through a nanopore and measuring the pore current.

Interrogation System. Used herein, "Interrogation System" is an automated, or semi-automated system for interrogating the sample. In some embodiments, whereby the sample is interrogated while within or on a fluidic device, the interrogation system interfaces with the fluidic device and controls the operation of the fluid device. In some embodiments, the interrogation system comprises a multitude of separate systems that together can be coordinated by a controller or user. For example, an instrument for loading sample into a fluidic device, an instrument for flowing said sample in said fluidic device, an instrument for imaging said sample in said fluidic device, a controller for operating software for analysis of said imaging data. In some embodiments, the interrogation system comprises an integration of all or a sub-set of systems.

In some embodiments whereby a sample is contained within, or on, a fluidic device, operation of the device by the interrogation system can comprise: manipulating the physical position and conformation of the package or long nucleic acid molecule via the application of external forces on said bodies; exposing the package or long nucleic acid molecule to an environmental condition or reagent for a time period; optically interrogating the static or dynamic configuration of the package or long nucleic acid molecule to facilitate analysis of their composition or as part of a feedback system to control operation of the device; extracting desired packages or long nucleic acid molecules from the device. The fluidic device and interrogation system can interface in a number of ways. A non-exhaustive list includes: fluidic ports (both open and sealed), electrical terminals, optical windows, mechanical pads, heat pipes or sinks, inductance coils, fluid dispensing, surface scanning probes. A non-exhaustive list of potential functions the interrogation system may perform on the device include: temperature monitoring, applying heat, removing heat, applying pressure or vacuum to ports, measuring vacuum, measuring pressure, applying a voltage, measuring a voltage, applying a current, measuring a current, applying electrical power, measuring electrical power, exposing the device to focused and/or unfocused electromagnetic waves, collecting the electromagnetic waves light generated or reflected from the device, in far or near-fiend setting, creating and measuring a temperature, electromagnetic force, surface energy or chemical concentration differential or gradient, dispensing liquid into a device well or port, or on the device surface, contacting the device surface or entity on the device surface with a contact probe (for example: an AFM tip).

In some embodiments, confirmation of the presence of a long nucleic acid molecule in a certain region of a fluid device and control over its physical position within said device is controlled by the interrogation system using a feedback controller system. Detection of the long nucleic acid molecule is via detection of at least one interrogated signal. In the preferred embodiment, the signal is an electromagnetic signal originating from a labelling body bound to said long nucleic acid molecule. In one embodiment, the control instrument feedback control system at least in part utilizes as input information the identification of a physical map profile within the long nucleic acid molecule, or absence of a physical map profile within the molecule.

In some embodiments, the interrogation system comprises localized computational processing modules within the system, adjacent computational processing modules via a direct communication connection, external computational processing modules via a network connection, or combination there-of Various examples of computational processing modules include: a PC, a micro-controller, an application specific integrated micro-chip (ASIC), a field-programmable gate array (FPGA), a CPU, a GPU, System on Chip, a network server, cloud computing service, or combinations there-of.

The interrogation system may include at least one fluidic dispensing tip that is capable of dispensing fluid drops at the desired x,y,z coordinates on the surface of the device, and in some embodiments, extracting fluid drops at the desired x,y,z coordinates on the surface of the fluidic device. Fluid dispensing and extracting may be in volumes of microliters, nanoliters, picoliters, femtoliters, or attoliters.

The interrogation system may be able to illuminate multiple light sources simultaneously, or in series, and be able to image multiple colors simultaneously, or in series. If imaging multiple colors simultaneously, this may be done on different cameras, on a single camera but different regions of the sensor array, or on the same sensor of the same camera. In some embodiments, the wavelength of light illuminated by the control instrument is chosen so as to interact with the sample, the sample labelling body, or a functionalized surface in some way. Non limiting examples include: photo-cleaving of the nucleic acid, photo-cleaving photo-cleavable linkers, manipulating optical tweezers, activating photo-activated reactions, de-protecting photolabile protecting groups, IR thermal heating.

Unless specifically stated otherwise, in this document any interrogation of a long nucleic acid molecule by an interrogation system comprises the embodiment where-by at least a portion of the long nucleic acid molecule is bound with at least one labelling body that comprises an intercalating fluorescent dye, and the interrogation system comprises an optical fluorescent imaging system.

Sequence. The term "sequence" or "nucleic acid sequence" or "oligonucleotide sequence" refers to a contiguous string of nucleotide bases and in particular contexts also refers to the particular placement of nucleotide bases in relation to each other as they appear in an oligonucleotide.

Sequencing can be performed by various systems currently available, such as, with limitation, a sequencing system by Illumina, Pacific Biosciences, Oxford Nanopore, Life Technologies (Ion Torrent), BGI.

Restriction Enzyme. The terms "restriction endonuclease" or "restriction enzyme" refer to enzymes that cut DNA at or near specific recognition nucleotide sequences known as "restriction sites" or "restriction recognition sites." Restriction endonuclease includes both enzymes that are able to recognize and cut methylated DNA and enzymes that only recognize un-methylated DNA. Methylated DNA includes dam methylation, dcm methylation and CpG methylation. Restriction endonucleases may recognize four, six, or eight nucleotide long restriction sites. These types of restriction endonucleases are referred to a 4-cutters, 6-cutters, and 8-cutters respectively. In some embodiments, a restriction endonuclease can be one of the following: Acll, Hindlll, Sspl, MluCI, Pcil, Agel, BspMI, BfuAI, SexAI, Mlul, BceAI, HpyCH4IV, HpyCH4III, Bael, BsaXI, AflIII, Spel, Bsrl, Bmrl, BglII, Afel, Alul, Stul, Seal, Clal, BspDI, PI-SceI, Nsil, Asel, Swal, CspCI, Mfel, Nb.BssSI, BssSal, BmgBI, Pmll, Drain, Alel, EcoPl5I, PvuII, AlwNI, BtsI-MutI, Ndel, Fatl, Nlalll, CviAII, Msll, FspEI, Xcml, BstXI, PflMI, Bed, Ncol, BseYI, Faul, Xmal, TspMI, Smal, Nt.Cvi-PII, LpnPI, Acil, Sadi, BsrBI, Hpall, Mspl, ScrFI, StyD4I, BsaJI, Bsll, Btgl, Neil, AvrII, Mnll, Nb.BbvCI, BbvCI, Nt.BbvCI, Sbfl, BpulOI, Bsu36I, EcoNI, HpyAV, BstNI, PspGI, Styl, Bcgl, Pvul, BstUI, Eagl, RsrII, BsiEI, BsiWI, BsmBI, Hpy99I, MspAll, Mspll, SgrAI, Bfal, BspCNI, PaeR7I, Xhol, Earl, Acul, Pstl, Bpml, Ddel, Sfcl, AflII, BpuEI, Smll, BsoBI, Aval, Mboll, Bbsl, Xmnl, Nb.Bsml, Bsml, EcoRI, Hgal, Zral, Aatll, PflFI, Tthl 1II, PshAI, Ahdl, Drdl, Eco53kl, Sad, BseRI, Mlyl, Plel, Nt.BstNBI, Hinfl, EcoRV, Mbol, Sau3AI, DpnII, BfuCI, Dpnl, BsaBI, Tfil, BsrDI, Nb.BsrDI, Bbvl, Btsal, Nb.BtsI, BstAPI, SfaNI, Sphl, Srfl, NmeAIII, Nael, NgoMIV, Bgll, AsiSI, BtgZI, HinPII, Hhal, BssHII, Notl, Fnu4HI, Cac8I, Mwol, Bmtl, Nhel, BspQI, Sapl, Nt.BspQI, Blpl, ApeKI, Tsel, Bspl286I, Nt.AlwI, Alwl, BamHI, BtsCI, Fokl, Haelll, Fsel, Sfil, Narl, Kasl, PluTI, Sfol, AscI, Ecil, BsmFI, PspOMI, Apal, Sau96I, NlalV, Acc65I, Kpnl, Bsal, Hphl, BstEII, Avail, Banl, BaeGI, BsaHI, Banll, Rsal, CviQI, BstZ17I, BciVI, Sall, BsmAI, BcoDI, Nt.BsmAI, ApaLI, Bsgl, AccI, Hpyl66II, Tsp45I, Hpal, Pmel, Hindi, BsiHKAI, TspRI, Apol, Nspl, BsrFal, BstYI, Haell, CviKI-1, EcoO109I, PpuMI, I-Ceul, SnaBI, I-Scel, BspHI, BspEI, Mmel, Taqal, Nrul, Hpyl88I, Hpyl88III, Xbal, Bell, HpyCH4V, Fspl, PI-PspI, MscI, BsrGI, Msel, Pad, Psil, BstBI, Dral, PspXI, BsaWI, BsaAI, or Eael.

Nickase enzymes are restriction enzymes that only cut one strand of DNA, but for the present purposes can function in a substantially similar manner to restriction enzymes in that they can sever double stranded DNA, whether to form blunt ends, overhangs or large overhangs, when accompanied by alternate means of single strand nicking such as a single-strand specific nuclease, photocleavage by photocycling of a DNA binding fluorophore such as YOYO-1, mechanical shear, BrdU incorporation and photostimulation, or a high density of cuts from one or more species of nickase.

Reference. A "genomic reference" or "reference" is any genomic data set that can be compared to another genomic data set. Any data formats may be employed, including but not limited to sequence data, karyotyping data, methylation data, genomic functional element data such as cis-regulatory element (CRE) map, primary level structural variant map data, higher order nucleic acid structure data, physical mapping data, genetic mapping data, optical mapping data, raw data, processed data, simulated data, signal profiles including those generated electronically or fluorescently. A genomic reference may include multiple data formats. A genomic reference may represent a consensus from multiple data sets, which may or may not originate from different data formats. The genomic reference may comprise a totality of genomic information of an organism or model, or a subset, or a representation. The genomic reference may be an incomplete representation of the genomic information it is representing.

The genomic reference may be derived from a genome that is indicative of an absence of a disease or disorder state or that is indicative of a disease or disorder state. Moreover, the genomic reference (e.g., having lengths of longer than 100 bp, longer than 1 kb, longer than 100 kb, longer than 10 Mb, longer than 1000 Mb) may be characterized in one or more respects, with non-limiting examples that include determining the presence (or absence) of a particular feature, a particular haplotype, a particular genetic variations, a particular structural variation, a particular single nucleotide polymorphism (SNP), and combinations thereof, referring not only to being present or absent from the genomic reference in its entirety, but also from a particular region of genomic reference, as defined by the neighboring genomic content. Moreover, any suitable type and number of characteristics of the genomic reference can be used to characterize the sample nucleic acid, as derived (or not derived) from a nucleic acid indicative of the disorder or disease based upon whether or not it displays a similar character to the reference.

In some cases, the genomic reference is a physical map. This can be generated in any number of ways, including but not limited to: raw single molecule data, processed single molecule data, an in-silico representation of a physical map generated from a sequence or simulation, an in-silico representation of a physical map generated by assembling and/or averaging multiple single molecule physical maps, or combination there-of. For example, based on a known, or partially known sequence, a simulated in-silico physical map can be generated based on the method of generating a physical map used. In an embodiment where-by the physical map comprises labelling bodies at known sequences, a discrete ordered set of segment lengths in base-pairs can be generated. In an embodiment where-by the physical map comprises a continuous analog signal of labelling signal density along the sequence length, in base-pairs based on simulated local hydrogen bonds dissociation kinetics between the double helices, in chemical moiety modification, regulatory factor association or structural folding patterns based on nucleotide sequence and predicted functional element database maps.

In some cases, the genomic reference is data obtained from microarrays (for example: DNA microarrays, MMChips, Protein microarrays, Peptide microarrays, Tissue microarrays, etc), or karyotypes, or FISH analysis. In some cases, the genomic reference is data obtained from proximity 3D mapping technologies or 3D physical mapping technologies.

In some cases, characterizations of the comparison with the genomic reference may be completed with the aid of a programmed computer processor. In some cases, such a programmed computer processor can be included in a computer control system.

Physical Mapping. "Physical mapping" or "mapping" of nucleic acid comprises a variety of methods of extracting genomic, epigenomic, functional, or structural information from a physical fragment of long nucleic acid molecule, in which the information extracted can be associated with a physical coordinate on the molecule. As a general rule, the information obtained is of a lower resolution than the actual underlying sequence information, but the two types of information are correlated (or anti-correlated) spatially within the molecule, and as such, the former often provides a 'map' for sequence content with respect to physical location along the nucleic acid. In some embodiments, the relationship between the map and the underlying sequence is direct, for example the map represents a density of AG content along the length of the molecule, or a frequency of a specific recognition sequence. In some embodiments, the relationship between the map the underlying sequence is indirect, for example the map represents the density of nucleic acid packed into structures with proteins, which in turn is at least partially a function of the underlying sequence. In some embodiments, the physical map is a linear physical map, in which the information extracted can be assigned along the length of an axis, for example, the AT/CG ratio along the major axis of long nucleic acid molecule. In the preferred embodiment, the "linear physical map" or "1D physical map" is generated by interrogating labelling bodies that are bound along an elongated portion of a long nucleic acid molecule's major axis. For clarity, a string occupying 3D space in a coiled state can be represented as straight line, and thus extracted values along the 3D coil, can be represented as binned values along a 1D representation of the string, and thus constitute a linear physical map. In some embodiments, the physical map is a "2D physical map", in which the information extracted can be assigned within a plane that comprises the molecule, for example: karyotyping. In some embodiments, the physical map is a "3D physical map", in which the information extracted can be assigned in 3D volume in which the molecule occupies. For example, tagging with super-resolution techniques to identify in (x,y,z) space the location of the tag within the chromosome as demonstrated with OligoFISSEQ [Nguyen, 2020], or in-situ genome sequencing [Payne, 2020].

The first and most widely used form of physical mapping is karyotyping, where-by metaphase chromosomes are treated with a stain process that preferentially binds to AT or CG regions, thus producing 'bands' that correlate with the underlying sequence as well as the structural and epigenomic patterns of the nucleic acid [Moore, 2001]. However, the resolution of such a process with respect to nucleotide sequence is quite poor, about 5-10 Mbp, due to the condensed nature of nucleic acid being imaged. More recent methods of using linear mapping of elongated interphase genomic DNA have been generated by imaging nucleic acid digested at known restriction sites [Schwartz, 1988, 6,147,198] (eg: see FIG. 1(A)), imaging attached fluorescent probes at nicking sites [Xiao, 2007] (eg: see Figure, 01(B)), imaging the fluorescent signature of a nucleic acid molecule's methylation pattern [Sharim, 2019], imaging the fluorescent signature of a chromatin's histone [Riehn, 2011], electrical detection of bound probes to a nucleic acid through a sensor [Rose, 2013, 2014/0272954], and electrical detection of the methylation signature on a nucleic acid using a nanopore sensor [Rand, 2017].

Another method of linear physical mapping is to measure the AT/CG relative density or local melting temperature along the length of an elongated nucleic molecule (eg: see FIG. 1(C)). Such a signal can either be used to compare against other similar maps, or against a map generated in-silico from sequence data. There are many ways of generating such a signal. For example, the signal can be fluorescent or electrical in nature. Nucleic acid can be uniformly stained with an intercalating dye, and then partially melted resulting in the relative loss of dye in regions of rich AT content [Tegenfeldt, 2009, 10,434,512]. Another method is to expose double stranded nucleic acid to two different species that compete to bind to the nucleic acid. One species is non-fluorescent and preferentially binds to AT rich regions, while the other species is fluorescent and has no such bias [Nilsson, 2014]. Yet another method is to use two different color dyes that differentially label the AT and CG regions.

Mapping using such non-condensed interphase nucleic acid polymer strands has improved upon the resolution of the primary sequence information, however the maps were stripped of any native structural folding or bound supporting proteins information and are often extracted from bulk solution of pooled samples with many potentially heterogeneous cells. Recently, 3D physical maps have been demonstrated where-by tags attached to chromosomes as specific locations are interrogated directly or indirectly to determine their relative position within the chromosome in 3D space (see [Jerkovic, 2021] for a review of the various methods). These methods can include super resolution microscopy methods such as SIM, SMLM, and STED, Oligopaint FISH methods, multiplexed oligopaint FISH methods, and OligoFISSEQ methods. In addition, also included are in-situ sequencing methods such as OligoFISSEQ [Nguyen, 2020]. Note, in this document, "3D physical Map(ping)" is different from "Proximity 3D Map(ping)", which is defined elsewhere in this document.

FIGS. 1(A), 1(B), 1(C) demonstrates a variety of different embodiments for generating and interrogating a long nucleic acid molecule linear physical map. In FIG. 1(A), a physical map of a long nucleic acid molecule 104 is generated by cleaving the molecule at particular sequence sites (eg: recognition sites for restriction enzymes) thus resulting in gaps 105 where the cleaving event took place. Along the length of a molecule, a dye is attached non-specifically (eg: using an intercalating dye) such that child molecules from the originating the parent molecule can be interrogated to generate a signal 101 that follows the physical length (0106) of the parent molecule. The signal can then be used determined the lengths and order of the individual child molecules {103-$x$}, and thus generating the parent molecule's physical map. In most embodiments of this method, the parent molecule is combed onto a surface and then cleaved, so as to maintain physical proximity and relative order of the child molecules. However, such an embodiment could also be implemented in at least a partially elongated state within an elongating channel of a confined fluidic device such that the order of the child molecules can be interrogated [Ramsey, 2015, 10,106,848]. In some embodiments, a mixture of different cleaving sites may be used simultaneously.

In FIG. 1(B), a physical map of a long nucleic acid molecule 114 is generated by sparsely binding label bodies 115 along the length of the molecule, with the binding sites correlated (or anti-correlated) with a set of specific target(s). In some methods, the labelling body is bound directly to a sequence motif target. In some methods, the labelling body generating a signal is bound indirectly via a process, for example: a sequence specific nick is generated, followed by incorporation of nucleotides starting at the nick site, some of which may be capable of generating a signal. The long nucleic acid molecule with labelling bodies is interrogated, generating signals 111 from the label bodies 115 along the physical length of the molecule 116. The distance between the signals, a collection of lengths and orders {113-$x$} then represents the molecule's physical map. In some embodiments, further information can be generated by also interpreting the relative magnitudes of the signals 112 from the various labelling sites. When fluorescent interrogation is used, different color labelling bodies can be used to represent different specific sites.

In FIG. 1(C), a physical map of a long nucleic acid molecule 124 is generated by densely binding labelling bodies 125 along the length of the molecule, such that the binding pattern correlates (or anti-correlates) with the underlying physical sequence content of the molecule. For example, the relative AT/CG content, or the relative melting temperature, or the relative density of methylated CGs. Due to the dense nature of the labelling bodies in this method, the physical map is not a collection of lengths and orders, but rather an analog signal 121 that varies in intensity along the physical length of the molecule 126.

The method of interrogation to generate a physical map is typically fluorescent imaging, however different embodiments are also possible, including a scanning probe along the length of a combed molecule on a surface, or a constriction device that measures the coulomb blockade current through or tunneling current across the constriction as the molecule translocate through.

Unless specifically stated otherwise, a physical map refers to any of the previously mentioned methods, including combinations there-of. For example, a long nucleic acid molecule may have a physical map generated from the AT/TC density with a fluorescent labelling body along the length of the molecule, and then also have a physical map generated from the methylation profile along the length of the molecule by constriction device as the molecule is transported through said constriction device.

Elongated DNA. The majority of linear physical mapping methods that use fluorescent imaging or electronic signals to extract a signal related to the underlying genomic, structural, or epigenomic content employ some form of method to at least locally 'elongate' the long nucleic acid molecule such that the resolution of the physical mapping in the region of elongation can be improved, and disambiguates reduced. A long nucleic acid molecule in its natural state in a solution will form a random coil. Thus, a variety of methods have been developed to 'uncoil' and elongate the molecule.

By binding a portion of long nucleic acid molecules on a functionalized solid surface, the molecule is elongated by flowing a solution and ultimately pulled taut, coming into full contact with the substrate surface [Bensimon, 1997, 7,368,234], a technique typically called 'combing' DNA. Alternatively, there are other long polymer elongation methods such as fluid flow induced elongation with ends anchoring on surface [Gibb, 2012], aqueous solution hydrodynamic focusing by laminar flows [Chan, 1999, 6,696,022], linearization by confining nanochannels [Tegenfeldt, 2005], long nucleic acid molecules in microfluidic device pulled by two angled opposing externally applied forces in a presence of physical obstacle features[Volkmuth, 1992], molecules hydrodynamically trapped in a fluidic device by simultaneously exposed to two opposing externally applied forces [Tanyeri, 2011].

Most of the time, the elongation state of at least a portion of the long nucleic acid molecule has to be sustained by an external force before otherwise returning to its natural random coiled state, unless at least a portion of the nucleic acid is retained in the elongated state by physical confinement without a sustaining external force [Dai, 2016].

Unless specifically stated otherwise, an 'elongated' or 'partially elongated' nucleic acid is a long nucleic acid fragment for which at least one segment of the major axis of the molecule comprising at least 1 kb can be projected against a 2D plane, and does not overlap with itself. For clarity, for embodiments where-by long nucleic acid includes additional structure, for example as when the nucleic acid is contained in chromatin, compacted with histones, the major axis refers to the larger chromatin molecule, not the nucleic acid strand itself. Therefore statements in this disclosure such as "along the length of the molecule" when referring to long nucleic acid molecules, refers to along the length of the major axis.

Proximity 3D Mapping. In this document, "proximity 3D mapping" refers to protocols that involve capturing the proximity relationship of at least two strands of nucleic acid, either of the same chromosome or not, by crosslinking them together directly or indirectly. For reference [Kempfer, 2020], and [Szabo, 2019] reviews these various techniques, of which a non-exhaustive list includes the following: 3C, 4C, 5C, Hi-C, TCC, PLAC-seq, ChIA-PET, Capture-C, C-HiC, Single-Cell HiC, GAM, SPRITE, ChIA-Drop.

Barcode. As used herein a "barcode" is a short nucleotide sequence (e.g., at least about 4, 6, 8, 10, 12, 14, 16, 18, 20, 25, 30, 35 nucleotides long) that encodes information. The barcodes can be one contiguous sequence or two or more noncontiguous sub-sequences. Barcodes can be used, e.g., to identify molecules in a partition or a bead, or a body to which an oligonucleotide is attached. In some embodiments, a bead-specific barcode is unique for that bead as compared to barcodes in oligonucleotides linked to other beads. In another example, a nucleic acid from each cell can be distinguished from nucleic acid of other cells due to the unique "cellular barcode." Such partition-specific, cellular, or bead barcodes can be generated using a variety of methods. In some cases, the partition-specific, cellular, or particle barcode is generated using a split and mix (also referred to as split and pool) synthetic scheme, for example as described in [Agresti, 2014, 2016/0060621]. More than one type of barcodes can in some embodiments be in the oligonucleotides described herein.

In some embodiments, the information associated with the barcode may be an identification of a single, a particular, a type, a sub-set, a specific selection, a random selection, a group of body, where the body may be a molecule, a higher-order nucleic acid structure, an organelle, a sample, a subject. In some embodiments, the information associated with the barcode may be a process, a time-stamp, a location, a relationship with another body and/or barcode, an experiment id, a sample id, or an environmental condition. In some embodiments multiple information content may be stored in the barcode, using any encoding technique.

In some embodiments the barcode is single strand. In some embodiments the barcode is double-stranded. In some embodiments, the barcode has both single and double strand components. In some embodiments the barcode is at least partially comprised of 2D and/or 3D structures, for example hairpins or a DNA origami structure.

In some embodiments, the information encoded in the barcode is done using error checking and/or error-correcting techniques to ensure the validity of the information stored within. For example, the use of hamming codes. In some cases where multiple information content is stored in the barcode, the separate pieces of information are encoded separately with their respective nucleotides within the barcodes. In other cases, the nucleotides can be shared using an encoding scheme. In some cases, compression techniques can be used to reduce the number of nucleotides needed.

In some embodiments, the information encoded in the barcode includes uniquely identifying the molecule to which it is conjugated. These types of barcodes are sometimes referred to as "unique molecular identifiers" or "UMIs". In still other examples, primers can be utilized that contain "partition-specific barcodes" unique to each partition, and "molecular barcodes" unique to each molecule. After barcoding, partitions can then be combined, and optionally amplified, while maintaining "virtual" partitioning based on the particular barcode. Thus, e.g., the presence or absence of a target nucleic acid comprising each barcode can be counted or tracked (e.g. by sequencing) without the necessity of maintaining physical partitions.

The length of the barcode sequence determines how many unique barcodes can be differentiated. For example, a 1 nucleotide barcode can differentiate 4, or fewer, different samples or molecules; a 4 nucleotide barcode can differentiate 256 samples or less; a 6 nucleotide barcode can differentiate 4096 different samples or less; and an 8 nucleotide barcode can index 65,536 different samples or less.

In some embodiments, the barcode sequences are designed or randomly generated using a selection software for choosing barcodes that are: without hairpin, or containing even base composition (15%-30% A,T,G and C), or without homopolymers (default allows 3 bases of same nucleotides), or without simple repeats, or without low complexity sequences, or not identical to common vector or adaptor sequences. Furthermore, barcodes can be designed to be unique even if there are 3 mismatch sequencing errors.

Barcodes are typically synthesized and/or polymerized (e.g., amplified) using processes that are inherently inexact. Thus, barcodes that are meant to be uniform (e.g., a cellular, particle, or partition-specific barcode shared amongst all barcoded nucleic acid of a single partition, cell, or bead) can contain various N−1 deletions or other mutations from the canonical barcode sequence. Thus, barcodes that are referred to as "identical" or "substantially identical" copies can in some embodiments include barcodes that differ due to one or more errors in, e.g., synthesis, polymerization, or purification errors, and thus can contain various N−1 deletions or other mutations from the canonical barcode sequence. However, such minor variations from theoretically ideal barcodes do not interfere with the methods, compositions, and kits described herein. Therefore, as used herein, the term "unique" in the context of a particle, cellular, partition-specific, or molecular barcode encompasses various inadvertent N−1 deletions and mutations from the ideal barcode sequence. In some cases, issues due to the inexact nature of barcode synthesis, polymerization, and/or amplification, are overcome by oversampling of possible barcode sequences as compared to the number of barcode sequences to be distinguished (e.g., at least about 2-, 5-, 10-fold or more possible barcode sequences), or by using error correction encoding techniques. The use of barcode technology is well known in the art, see for example [Shiroguchi, 2012] and [Smith, 2010]. Further methods and compositions for using barcode technology include those described in [Agresti, 2014, 2016/0060621].

In some embodiments, at least a portion of the barcode can also be used as a primer binding site. In some embodiments, the primer binding site is for a PCR primer. In some embodiments, all barcodes that form a set of unique barcodes contain within said barcodes a globally identical primer binding site, such that a single primer sequence can be used to bind to all barcodes. In some embodiments, the primer will be the complement sequence of the primer binding site. In other embodiments, the primer will be the same sequence as the primer binding site, as the primer will bind to a previously amplified product of the original primer binding site. In some embodiments, there may be a combination.

In addition, in some embodiments, at least a portion of the barcode can also be used a primer.

Cleavable Linker. The "cleavage domain" or "cleavable linker" represents link between at least two entities that can be used to reversibly attach said at least two entities. In some embodiments, the at least two entities are macromolecules. In some embodiments, at least one the of the entities is a substrate, or connected to a substrate.

In some embodiments, the cleavage domain linking the entities is a disulfide bond. A reducing agent can be added to break the disulfide bonds, resulting in the separation of the entities. As another example, heating can also result in degradation of the cleavage domain and separation of the entities, with or without a photosensitizer such as a gold nanoparticle. In some embodiments, laser radiation is used to heat and degrade cleavage domains, in some embodiment the laser radiation is targeted at specific locations. In some embodiments, the cleavage domain is a photo-sensitive chemical bond (e.g., a chemical bond that dissociates when exposed to light such as ultraviolet light).

Oligonucleotides with photo-sensitive chemical bonds (e.g., photo-cleavable linkers) have various advantages. They can be cleaved efficiently and rapidly (e.g., in nanoseconds and milliseconds). In some cases, photo-masks can be used such that only specific regions of the array are exposed to cleavable stimuli (e.g., exposure to UV light, exposure to light, exposure to heat induced by laser). Alternately, selective illumination can be achieved by imaging digital micromirror devices to the sample or directing focused light by means of galvanometer mirrors and imaging lenses. When a photo-cleavable linker is used, the cleavable reaction is triggered by light, and can be highly selective to the linker and consequently biorthogonal. Typically, wavelength absorption for the photo cleavable linker is located in the near-UV range of the spectrum. In some embodiments, absorption maximum of the photo-cleavable linker is from about 200 nm to about 600 nm.

Non-limiting examples of a photo-sensitive chemical bond that can be used in a cleavage domain include those described in [Leriche, 2012] and [Weissleder, 2013, 2017/0275669], both of which are incorporated by reference herein in their entireties. For example, linkers that comprise photo-sensitive chemical bonds include 3-amino-3-(2-nitrophenyl)propionic acid (ANP), phenacyl ester derivatives, 8-quinolinyl benzenesulfonate, dicoumarin, 6-bromo-7-alkixycoumarin ylmethoxycarbonyl, a bimane-based linker, and a bis-arylhydrazone based linker. In some embodiments, the photo-sensitive bond is part of a cleavable linker such as an ortho-nitrobenzyl (oNB) linker. Other examples of photo-sensitive chemical bonds that can be used in a cleavage domain include halogenated nucleosides such as bromodeoxyuridine (BrdU). BrdU is an analog of thymidine that can be readily incorporated into oligonucleotides, and is sensitive to UVB light (280-320 nm range). Upon exposure to UVB light, a photo-cleavage reaction occurs (e.g., at a nucleoside immediately 5' to the site of BrdU incorporation ([Doddridge, 1998] and [Cook, 1999]) that results in cleavage of the cleavage domain.

Other examples of cleavage domains include labile chemical bonds such as, but not limited to, ester linkages (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), an abasic or apurinic/apyrimidinic (AP) site (e.g., cleavable with an alkali or an AP endonuclease), or a phosphodiester linkage (e.g., cleavable via a nuclease (e.g., DNAase)).

In some embodiments, the cleavage domain includes a sequence that is recognized by one or more enzymes capable of cleaving a nucleic acid molecule, e.g., capable of breaking the phosphodiester linkage between two or more nucleotides. A bond can be cleavable via other nucleic acid molecule targeting enzymes, such as restriction enzymes (e.g., restriction endonucleases). For example, the cleavage domain can include a restriction endonuclease (restriction enzyme) recognition sequence. Restriction enzymes cut double-stranded or single stranded DNA at specific recognition nucleotide sequences known as restriction sites. In some embodiments, a rare-cutting restriction enzyme, e.g., enzymes with a long recognition site (at least 8 base pairs in length), is used to reduce the possibility of cleaving elsewhere.

In some embodiments, the cleavage domain includes a poly(U) sequence which can be cleaved by a mixture of Uracil DNA glycosylase (UDG) and the DNA glycosylase-lyase Endonuclease VIII, commercially known as the USER™ enzyme. Releasable entities can be available for reaction once released.

In some embodiments, the cleavage domain includes a nickase recognition site or sequence. Nickases are endonucleases which cleave only a single strand of a DNA duplex. Thus, the cleavage domain can include a nickase recognition site such that nicking of the site destabilizes the physical link between the entities, and results in them being separated.

In some embodiments, the cleavage domain comprises a nucleic acid sequence designed to be recognized and cut by a CRISPR associated system in the presence of a targeted guide RNA. In the preferred embodiments, the designed target sequences are unique, extremely rare, or non-present within the genome of the sample of interest.

In some embodiments the cleavage domain includes double strand nucleic acid such that two strands are not 100% complementary (for example, the number of mismatched base pairs can be one, two, or three base pairs). Such a mismatch is recognized, e.g., by the MutY and T7 endonuclease I enzymes, which results in cleavage of the nucleic acid molecule at the position of the mismatch.

In some embodiments, the cleavage domain includes a double strand nucleic acid which can be cleaved by melting the two strands to separate them from each other. In some embodiments, the two strands are not 100% complementary or contain a high proportion of AT pairs (>50%) such that required melting temperature is lower than the average melting temperature of a genome. In some embodiments the cleavage domain may be 2 base-pairs or more, or 3 base-pairs or more, or 4 base-pairs or more, or 5 base-pairs or more, or 6 base-pairs or more, or 8 base-pairs or more, or 10 base-pairs or more. In some embodiments, the domain melting comprises increasing the temperature, or changing the pH, changing the ionic strength of the buffer, chelation of multivalent ions or addition of a competitive binder.

Binding. "Binding", "bound", "bind" as used herein generally refers to a covalent or non-covalent interaction between two entities (referred to herein as "binding partners", e.g., a substrate and an enzyme or an antibody and an epitope). Any chemical binding between two or more bodies is a bond, including but not limited to: covalent bonding, sigma bonding, pi ponding, ionic bonding, dipolar bonding, metalic bonding, intermolecular bonding, hydrogen bonding, Van der Waals bonding. As "binding" is a general term, the following are all examples of types of binding: "hybridization", hydrogen-binding, minor-groove-binding, major-groove-binding, click-binding, affinity-binding, specific and non-specific binding. Other examples include: Transcription-factor binding to nucleic acid, protein binding to nucleic acid.

Specific and Non-Specific Binding. As used herein, the terms "specifically binds" and "non-specifically binds" must be interpreted in the context for which these terms are used in the text. For example, a body may "specifically bind" to a nucleic acid molecule but have no significant preference or bias with respect the underlying sequence of said nucleic acid molecule over some genomic length scale and/or within some genomic region. As such, in the context of molecule's sequence, the body "non-specifically binds" to said nucleic acid molecule.

When in the context of binding between physically distinct molecules, "Specific binding" typically refers to interaction between two binding partners such that the binding partners bind to one another, but do not bind other molecules that may be present in the environment (e.g., in a biological sample, in tissue) at a significant or substantial level under a given set of conditions (e.g., physiological conditions).

Preferentially Binds. The term "preferentially binds" means that in comparison between at least two different binding sites (the sites can be on the same entity, or can be physically different entities), there is a non-zero probability of binding between a certain body and both sites, however conditions can exist in which the probability of binding of the certain body is preferable at one site over another.

Affinity Group. An "affinity group" is a molecule or molecular moiety which has a high affinity or preference for associating or binding with another specific or particular molecule or moiety, its "affinity partner". The association or binding with another specific or particular molecule or moiety can be via a non-covalent interaction, such as hydrogen bonding, ionic forces, and van der Waals interactions. An affinity group can, for example, be biotin, which has a high affinity for the protein avidin or streptavidin. An affinity group, for example, can also refer to avidin or streptavidin which has an affinity for biotin. Molecules that form the basis of various affinity chromatography methods are recognizable as affinity groups. Other examples of an affinity group and specific or particular molecule or moiety to which it binds or associates with include, but are not limited to, antibodies or antibody fragments and their respective antigens, such as digoxigenin and anti-digoxigenin antibodies, lectin, and carbohydrates (e.g., a sugar, a monosaccharide, a disaccharide, or a polysaccharide), and receptors and receptor ligands.

An affinity group may be capable of click chemistry reactions. The term "click chemistry" refers to a chemical philosophy introduced by K. Barry Sharpless, describing chemistry tailored to generate covalent bonds quickly and reliably by joining small units comprising reactive groups together. Click chemistry does not refer to a specific reaction, but to a concept including reactions that mimic reactions found in nature. In some embodiments, click chemistry reactions are modular, wide in scope, give high chemical yields, generate inoffensive byproducts, are stereospecific, exhibit a large thermodynamic driving force >84 kJ/mol to favor a reaction with a single reaction product, and/or can be carried out under physiological conditions. A distinct exothermic reaction makes a reactant "spring loaded". In some embodiments, a click chemistry reaction exhibits high atom economy, can be carried out under simple reaction conditions, use readily available starting materials and reagents, uses no toxic solvents or use a solvent that is benign or easily removed (preferably water), and/or provides simple product isolation by non-chromatographic methods (crystallization or distillation). For example, an azide is a partner to a cyclooctyne or any other alkyne.

An affinity group may form one part of a reactive group in a cross-linking entity.

Any pair of affinity group and its specific or particular molecule or moiety to which it binds or associates with can have their roles reversed, for example, such that between a first molecule and a second molecule, in a first instance the first molecule is characterized as an affinity group for the second molecule, and in a second instance the second molecule is characterized as an affinity group for the first molecule.

Photolabile protecting group. A "photolabile protecting group" is a reactive functional group that interacts with an affinity group, such that when the photolabile protecting group is exposed to a certain light, the result is an increase in the likelihood said affinity group will bind to its associated binding partner, when compared to its previous protected status. Prior to such light exposure, the affinity group is commonly referred to as being "caged".

Many approaches are known in the art for caged affinity groups and methods of making and using, such as those which protect an affinity group to reduce or eliminate the affinity the affinity group possesses for a particular target binding species. These approaches can be utilized to prevent binding of a member with undesired targets which are otherwise capable of binding with the member, or for other purposes such as controlling the time and location of binding. Additionally, a variety of approaches can be utilized to ensure that the affinity of the affinity group for the target binding species is not reduced, at least not substantially, after uncaging (as compared to the affinity possessed without the involvement of caging). For instance, a non-limiting example within the process of manufacturing polymer arrays through photolithography is the protection of otherwise reactive functional groups with photolabile protecting groups (e.g., MeNPOC, NNPOC, NPPOC). These reactive functional groups are then activated for coupling with monomers within certain regions of the substrate through selective illumination, with the light possessing wavelength(s) capable of photolyzing the photolabile protecting groups and freeing the previously protected, or caged, hydroxyl groups. This approach of protecting affinity groups within a cage is certainly not limited to photolithographic synthesis of nucleic acid arrays, and many variations and adaptations of the concept are well known in the art for use with a variety of molecules, such as nucleic acids, amino acids, antibodies, etc. in a variety of approaches, chemistries, and applications.

Photoprotection of a molecule, such as biotin, is generally achieved through modification of the molecule with a photoactivatable protecting group, with the protecting group located at a critical position (e.g., deactivating a particular bond) to prevent undesired reactions while the molecule is still caged by the protecting group. The inactive, caged molecule is then uncaged through appropriate irradiation, such as illumination at one or more appropriate wavelengths, such as ultraviolet light with wavelengths shorter than 340 nm, 350 nm, 360 nm, 365 nm, 375 nm, 390 nm or more.

Many approaches are available for the caging of polymers such as oligonucleotides with photolabile protecting groups. For example, the caging protecting group may be placed on internucleotide phosphates, various positions on the sugar, or the nucleobase. Certain approaches incorporate biotin during phosphoramidite synthesis of the oligonucleotides. For background regarding the use of biotin, particularly caged protected biotin, see U.S. Pat. Nos. [Barrett, 1989, 5,252,743]; [Barrett, 1989, 5,451,683]; [Fodor, 1989, 6,919, 211]; and [Fodor, 1989, 6,955,915]; U.S. Patent Application Publication No. [Fodor, 1989, 2003/0119011]; and [Pirrung, 1996], all of which are incorporated herein by reference in their entireties for all purposes.

Capture Domain. "Capture domains" are entities that specifically or non-specifically bind to nucleic acid molecules, chromatin, or other bio-molecules such as proteins, either directly, or via a series of reactions and/or processing steps.

In some embodiments, the capture domain is a functional nucleic acid sequence configured to interact with one or more analytes, such as one or more different types of nucleic acids (e.g., RNA molecules and DNA molecules). In some embodiments, the functional nucleic acid sequence can include an N-mer sequence (e.g., a random N-mer sequence), which N-mer sequences are selected to interact with a plurality of DNA molecules. In some embodiments, the functional sequence can include a poly(T) sequence, which poly(T) sequences are configured to interact with messenger RNA (mRNA) molecules via the poly(A) tail of an mRNA transcript. In some embodiments, the functional nucleic acid sequence is the binding target of a protein (e.g., a transcription factor, a DNA binding protein, or a RNA binding protein)

Capture domains can include ribonucleotides, deoxyribonucleotides and/or peptide nucleic acids. They can contain synthetic nucleotide residues that are capable of participating in Watson-Crick type or analogous base pair interactions. In some embodiments, the capture domain is capable of priming a reverse transcription reaction to generate cDNA that is complementary to the captured RNA molecules. In some embodiments, the capture domain can prime a DNA extension (polymerase) reaction to generate DNA that is complementary to the captured DNA molecules.

In some embodiments, the capture domain can template a ligation reaction between the captured DNA molecules and the capture domain. In some embodiments, the capture domain can be ligated to one strand of the captured DNA molecules. For example, Splint® ligase along with RNA or DNA sequences (e.g., degenerate RNA) can be used to ligate a single-stranded DNA or RNA to the capture domain. In some embodiments, ligases with RNA-templated ligase activity, e.g., Splint® ligase, T4 RNA ligase 2 or KOD ligase, can be used to ligate a single-stranded DNA or RNA to the capture domain. In some embodiments, a capture domain includes a splint oligonucleotide. In some embodiments, a capture domain captures a splint oligonucleotide. In some embodiments, the capture domain includes a free 3' end that can be extended, e.g., by template dependent polymerization, to form an extended capture domain. In some embodiments, the capture domain includes a nucleotide sequence that is capable of hybridizing to nucleic acid, e.g., RNA or other analyte, present in the cells of the biological sample contacted with the array. In some embodiments, the capture domain can be selected or designed to bind selectively or specifically to a target nucleic acid. For example, the capture domain can be selected or designed to capture mRNA by way of hybridization to the mRNA poly(A) tail. Thus, in some embodiments, the capture domain includes a poly(T) DNA oligonucleotide, e.g., a series of consecutive deoxythymidine residues linked by phosphodiester bonds, which is capable of hybridizing to the poly(A) tail of mRNA. In some embodiments, the capture domain can include nucleotides that are functionally or structurally analogous to a poly(T) tail. For example, a poly(U) oligonucleotide or an oligonucleotide included of deoxythymidine analogues. In some embodiments, the capture domain includes at least 2, 3, 4, 5, 6, 7, 8, 9, 10, 11, 12, 13, 14, 15, 16, 17, 18, 19, or 20 nucleotides. In some embodiments, the capture domain includes at least 25, 30, 35, 40, 50 nucleotides. For example, hybridization sequences commonly used in FISH probes can be 40 bp in length.

In some embodiments, a capture domain includes a sequence that is capable of binding to mRNA and/or genomic DNA. For example, the capture domain can include a nucleic acid sequence (e.g., a poly(T) sequence) capable of binding to a poly(A) tail of an mRNA and/or to a poly(A) homopolymeric sequence present in genomic DNA. In some embodiments, a homopolymeric sequence is added to an mRNA molecule or a genomic DNA molecule using a terminal transferase enzyme in order to produce an analyte that has a poly(A) or poly(T) sequence. For example, a poly(A) sequence can be added to an analyte (e.g., a fragment of genomic DNA) thereby making the analyte capable of capture by a poly(T) capture domain.

In some embodiments, random sequences, e.g., random hexamers or similar sequences, can be used to form all or a part of the capture domain. For example, random sequences can be used in conjunction with poly(T) (or poly(T) analogue) sequences. Thus, where a capture domain includes a poly(T) (or a "poly(T)-like") oligonucleotide, it can also include a random oligonucleotide sequence (e.g.,"poly(T)-random sequence" domain). This can, for example, be located 5' or 3' of the poly(T) sequence, e.g., at the 3' end of the capture domain. The poly(T)-random sequence domain can facilitate the capture of the mRNA poly(A) tail. In some embodiments, the capture domain can be an entirely random sequence. In some embodiments, degenerate capture domains can be used. In some embodiments, the capture domain can comprise a universal sequence. In some embodiments, the capture domain can comprise a barcode.

The capture domain can be based on a particular gene sequence or particular motif sequence or common/conserved sequence, that it is designed to capture (i.e., a sequence-specific capture domain). Thus, in some embodiments, the capture domain is capable of binding selectively to a desired sub-type or subset of nucleic acid, for example a particular type of RNA, such as mRNA, rRNA, tRNA, SRP RNA, tmRNA, snRNA, snoRNA, SmY RNA, scaRNA, gRNA, RNase P, RNase MRP, TERC, SL RNA, aRNA, cis-NAT, crRNA, lncRNA, miRNA, piRNA, siRNA, shRNA, tasiRNA, rasiRNA, 7SK, eRNA, ncRNA or other types of RNA. In a non-limiting example, the capture domain can be capable of binding selectively to a desired subset of ribonucleic acids, for example, microbiome RNA, such as 16S rRNA.

In some embodiments, a capture domain includes an "anchor" or "anchoring sequence", which is a sequence of nucleotides that is designed to ensure that the capture domain hybridizes to the intended analyte. In some embodiments, an anchor sequence includes a sequence of nucleotides, including a 1-mer, 2-mer, 3-mer or longer sequence. In some embodiments, the short sequence is random. For example, a capture domain including a poly(T) sequence can be designed to capture an mRNA. In such embodiments, an anchoring sequence can include a random 3-mer (e.g., GGG) that helps ensure that the poly(T) capture domain hybridizes to an mRNA. In some embodiments, an anchoring sequence can be VN, N, or NN. Alternatively, the sequence can be designed using a specific sequence of nucleotides. In some embodiments, the anchor sequence is at the 3' end of the capture domain. In some embodiments, the anchor sequence is at the 5' end of the capture domain.

In some embodiments, capture domains are blocked prior to contacting the biological sample. In some embodiments, the free 3' end of the capture domain is blocked or modified. In some embodiments, the free 3' end of the capture domain can be masked by hybridized nucleic acid structures, e.g., hairpins. In some embodiments, the free 3' end of the capture domain can be blocked by chemical modification, e.g., addition of an azidomethyl group as a chemically reversible capping moiety such that the capture domains do not include a free 3' end. Blocking or modifying the capture domain, particularly at the free 3' end of the capture domain, prior to contacting the biological sample with said domains, prevents modification of the capture domain, e.g., prevents the addition of a poly(A) tail to the free 3' end of the capture domain. In some embodiments, capture domains are caged by a photolabile protecting group, and can become active via the appropriate exposure of a certain wavelength of light.

Non-limiting examples of 3' modifications include dideoxy C-3' (3'-ddC), 3' inverted dT, 3' C3 spacer, 3' Amino, and 3' phosphorylation. In some embodiments, the nucleic acid in the biological sample can be modified such that it can be captured by the capture domain. For example, an adaptor sequence (including a complementary binding domain capable of binding to the capture domain) can be added to the end of the nucleic acid, e.g., fragmented genomic DNA. In some embodiments, this is achieved by ligation of the adaptor sequence or extension of the nucleic acid. In some embodiments, an enzyme is used to incorporate additional nucleotides at the end of the nucleic acid sequence, e.g., a poly(A) tail. In some embodiments, the capture domains can be reversibly masked or modified such that the capture domain does not include a free 3' end. In some embodiments, the 3' end is removed, modified, or made inaccessible so that the capture domain is not susceptible to the process used to modify the nucleic acid of the biological sample, e.g., ligation or extension.

In some embodiments, the capture domain can be a non-nucleic acid domain. Examples of suitable capture domains that are not exclusively nucleic-acid based include, but are not limited to, proteins, peptides, aptamers, antigens, antibodies, and molecular analogs that mimic the functionality of any of the capture domains described herein.

In some embodiments, the capture domain comprises an affinity agent that can non-specifically or specifically bind to nucleic acid, chromatin, and/or proteins and thus can be used as a component of a cross-linking agent. In some embodiments, the capture domain comprises a cross-linking moiety.

In some embodiments, the cross-linking moiety may be activated by a variety of treatments or exposure to, or changes in environmental conditions.

In some embodiments, the capture domain comprises Psoralen, or derivatives there-of. In some embodiments, the capture domain comprises diazirine, or derivatives there-of. In some embodiments, the capture domain comprises Formaldehyde, or derivatives there-of. In some embodiments, the capture domain comprises any of the following, or derivatives there-of: trioxsalen, methoxypsoralen, hydroxymethyl-4,5',8-trimethylpsoralen, alkylating agents such as nitrogen mustards, cis-platin, chloroethyl nitroso urea, mitomycin C, bifunctional aldehydes, and bifunctional quinone methides.

In some embodiment, the capture domain comprises any of the following, or derivatives there-of: disuccinimidyl glutarate, disuccinimidyl suberate, disuccinimidyl tartrate, dimethyl adipimidate, dimethyl pimelimidate, dimethyl suberimidate, 1,5-difluoro-2,4-dinitrobenzene, N-maleimidopropionic acid hydrazide, 3-(2-pyridyldithio) propionyl hydrazide, bismaleimidoethane, diazarine, succinimidyl iodoacetate, N-maleimidoacet-oxysuccinimide pyridyldithio)propionate. maleimide groups, thiol reactive groups, amino groups such as primary and secondary amines, carboxyl groups, hydroxyl groups, aldehyde groups, alkyne groups, azide groups, carbonyls, haloacetyl (e.g., iodoacetyl) groups, imidoester groups, N-hydroxysuccinimide esters, sulfhydryl groups, pyridyl disulfide groups, In some embodiments, capture domains comprise photoreactive capture domains that become reactive only upon exposure to ultraviolet or visible light. Two example photoreactive chemical groups include aryl-azides and diazirines.

Capture Probe. A "capture probe" or "probe" refers a molecule that comprises a capture domain and a barcode. In some embodiments, the capture probe comprises a cleavable linker or cleavage domain, or at least a residue or at least a portion of a cleavable linker or cleavage domain. For example, a capture probe may be connected to a body through a cleavable linker, and after being released from said body via cleavage of said linker, the capture probe retains a portion of the linker. In some embodiments, the capture probe comprises a priming site. In some embodiments, the capture probe comprises one or more fluorophores. In some embodiments, the capture probe comprises a donor or acceptor of a FRET pair, or a quenching body which can quench a nearby fluorophore. In some embodiments, the capture probe comprises functional sequences, such as a functional domain. In some embodiments, the capture probe comprises an affinity group in addition to the capture domain, for example, a biotin.

Functional Domain. A "functional domain" includes a functional nucleotide sequence for a downstream analytical step in the overall analysis procedure. They are commonly useful for subsequent processing in sequencing workflows. For example, the functional sequence can include a sequencer specific flow cell attachment sequence, and/or sequencing primer sequences, e.g., a R1 primer sequence for Illumina® sequencing, and/or an R2 primer sequence for Illumina® sequencing. The functional sequences can generally be selected for compatibility with any of a variety of different sequencing systems, e.g., 454 Sequencing, Ion Torrent Proton or PGM, Illumina X10, PacBio, Nanopore, BGI, etc., and the requirements thereof. Examples of such commercialized sequencing systems and techniques, for which suitable functional sequences can be used, include (but are not limited to) Roche 454 sequencing, Ion Torrent Proton or PGM sequencing, Illumina XI 0 sequencing, PacBio SMRT sequencing, and Oxford Nanopore sequencing. Further, in some embodiments, functional sequences can be selected for compatibility with other sequencing systems, including non-commercialized sequencing systems. Examples of functional sequences and uses thereof are described in [Hindson, 2012, 2014/0378345] and [Hindson, 2014 2015/0376609], the entire contents of each of which are incorporated herein by reference.

Crosslinker. The term "crosslink", "crosslinking" or "crosslink" as used herein, refers to any stable chemical association between two or more compounds made possible via binding to a "crosslinker" (or "crosslinking agent", or "crosslinking reagent") that bridges the two or more compounds, such that they may be further processed as a unit, wherein the crosslinker comprises at least two affinity groups or capture domains which will bind with their respective target compound. Such stability may be based upon covalent and/or non-covalent bonding and may be reversed by chemical or photoactivation. The two or more compounds may be identical, similar, or different in nature. Similarly, the two or more affinity groups or capture domains may be identical, similar, or different in nature.

Combing. Defined herein, "molecular combining" or "combing" refers to the process of immobilizing at least a portion of a macromolecule, in particular nucleic acid molecules, to a substrate surface, or within a porous film on a substrate surface, such that at least a portion of the macromolecule is elongated in a plane that is substantially parallel to the surface of said substrate. The elongated portion can be fully immobilized to the substrate, or at least of portion of said portion have some degree of freedom. In some embodiments at least a portion of the molecule is elongated within a porous material film parallel to the surface of said substrate, or at least a portion of the molecule is elongated on top of a porous material film parallel to the surface of said substrate, or at least a portion of the molecule is elongated and suspended between two points. In some embodiments, the substrate surface is at least part of a fluidic device.

In one embodiment, a single nucleic acid molecule binds by one or both extremities (or regions proximal to one or both extremity) to a modified surface (e.g., silanised glass) and are then substantially uniformly stretched and aligned by a receding air/water interface. Schurra and Bensimon (2009) "Combing genomic DNA for structure and functional studies." Methods Mol. Biol. 464: 71-90; See also U.S. Pat. No. [Bensimon, 1995, 7,122,647], both of which are herein incorporated by reference in their entirety.

The percentage of fully-stretched nucleic acid molecules depends on the length of the nucleic acid molecules and method used. Generally, the longer the nucleic acid molecules stretched on a surface, the easier it is to achieve a complete stretching. For example, according to [Conti, 2003], over 40% of a 10 kb DNA molecules could be routinely stretched with some conditions of capillary flow, while only 20% of a 4 kb molecules could be fully stretched using the same conditions. For shorter nucleic acid fragments, the stretching quality can be improved with the stronger flow induced by dropping coverslips onto the slides. However, this approach may shear longer nucleic acid fragments into shorter pieces and is therefore may not suitable for stretching longer molecules. See e.g., [Conti, 2003] Conti, et al. (2003) Current Protocols in Cytometry John Wiley & Sons, Inc. and [Gueroui, 2002] Gueroui, et al. (Apr. 30, 2002) "Observation by fluorescence microscopy of transcription on single combed DNA." PNAS 99(9): 6005-6010, both of which are hereby incorporated by reference in their entirety. See also [Bensimon, 1994, 5,840,862], [Bensimon, 1995, WO 97/18326], [Bensimon, 1999, WO 00/73503], [Bensimon, 1995, 7,122,647] which are hereby incorporated by reference in their entirety. [Lebofsky, 2003] "Single DNA molecule analysis: applications of molecular combing." Brief Funct. Genomic Proteomic 1: 385-96, hereby incorporated by reference in its entirety.

In some embodiments, the long nucleic acid molecule is attached to a substrate at one end and is stretched by various weak forces (e.g., electric force, surface tension, or optical force). In this embodiment, one end of the nucleic acid molecule is first anchored to a surface. For example, the molecule can be attached to a hydrophobic surface (e.g., modified glass) by adsorption. The anchored nucleic acid molecules can be stretched by a receding meniscus, evaporation, or by nitrogen gas flow. See e.g., [Chan, 2006] "A simple DNA stretching method for fluorescence imaging of single DNA molecules." Nucleic Acids Research 34(17): e1-e6, herein incorporated by reference in it entirety.

Another embodiment, the nucleic acid molecule is stretched by dissolving the long nucleic acid molecules in a drop of buffer and running down the substrate. In a further embodiment, the long nucleic acid molecules are embedded in agarose, or other gel. The agarose comprising the nucleic acid is then melted and combed along the substrate.

In another embodiment, the molecule is attached to the substrate at least one specific point, allowing the remainder of the molecule a substantial amount of degree of freedom, such that portion of elongation in the molecule is obtained by the application of an external force on the molecule in a direction that is substantially parallel to the surface of the substrate. Examples of such embodiments include "DNA curtains" [Gibb, 2012] where-by the point of attachment is a controlled process, or the point of attachment can be random via interactions of the molecule with fluidic features, for example pillars as shown by [Craighead, 2011, U.S. Pat. No. 9,926,552].

Figure 2:
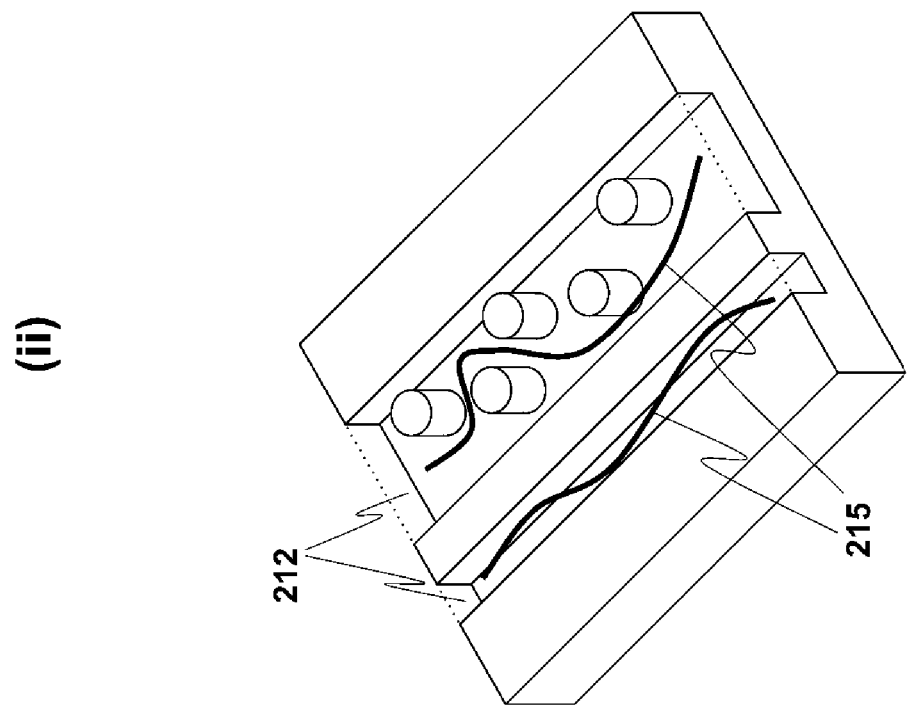
Figure 2:
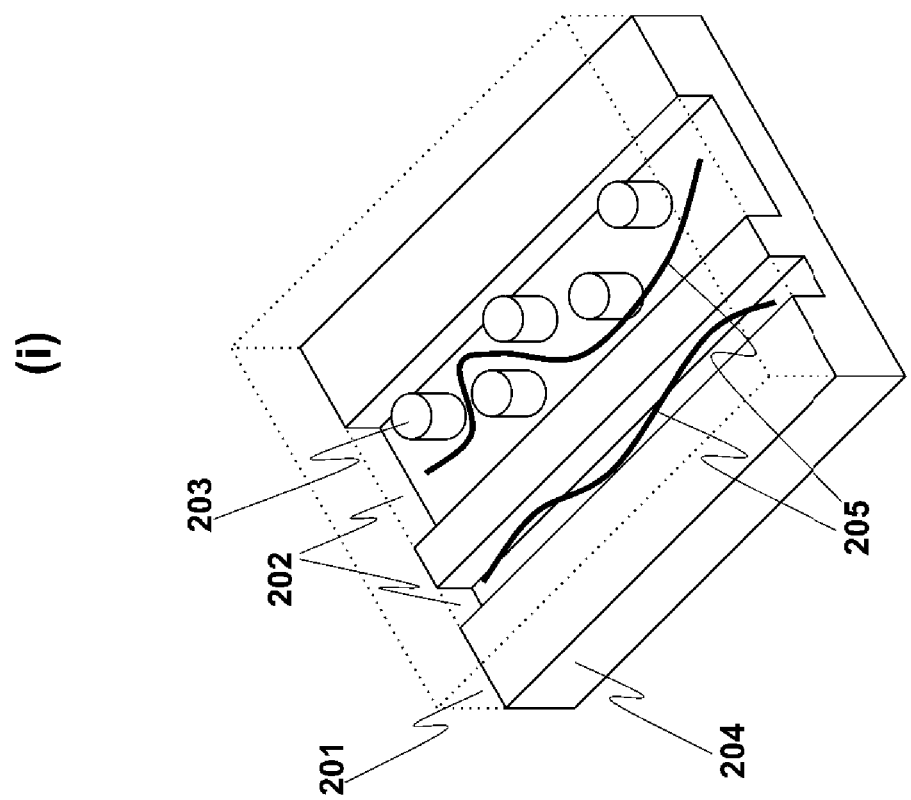

In some embodiments, molecular combing can be done with fluid flow generated by elongating the molecule in a fluidic device such that after elongation in the device, the molecule is presented in an elongated state on the surface of the device, or within a porous film on the surface of the device. In some embodiments, the fluidic channels of the device not fully confined, such that after evaporation of the transporting solution, the molecules are at least partially immobilized on the surface of the device in an elongated state. In some embodiments, as shown in in FIG. 2, a molecule 205 is elongated in a confined elongation channel of a microfluidic device (204), here with channel dimensions (202) that provide a confining environment and/or physical obstacles (203) that aid in promoting elongation. A gelling material within the solution that surrounds the molecule within the microfluidic device is then gelled. Finally, the molecules (215) are made accessible to the surface of the device via removal of the roof (201) while maintain the molecules within the gel film, or by using a porous roof material.

Microfluidic Device. The term "microfluidic device" or "fluidic device" as used herein generally refers to a device configured for fluid transport and/or transport of bodies through a fluid, and having a fluidic channel in which fluid can flow with at least one minimum dimension of no greater than about 100 microns. The minimum dimension can be any of length, width, height, radius, or cross-sectional axis. A microfluidic device can also include a plurality of fluidic channels. The dimension(s) of a given fluidic channel of a microfluidic device may vary depending, for example, on the particular configuration of the channel and/or channels and other features also included in the device.

Microfluidic devices described herein can also include any additional components that can, for example, aid in regulating fluid flow, such as a fluid flow regulator (e.g., a pump, a source of pressure, etc.), features that aid in preventing clogging of fluidic channels (e.g., funnel features in channels; reservoirs positioned between channels, reservoirs that provide fluids to fluidic channels, etc.) and/or removing debris from fluid streams, such as, for example, filters. Moreover, microfluidic devices may be configured as a fluidic chip that includes one or more reservoirs that supply fluids to an arrangement of microfluidic channels and also includes one or more reservoirs that receive fluids that have passed through the microfluidic device. In addition, microfluidic devices may be constructed of any suitable material(s), including polymer species and glass, or channels and cavities formed by multi-phase immiscible medium encapsulation. Microfluidic devices can contain a number of microchannels, valves, pumps, reactor, mixers and other components for producing the droplets. Microfluidic devices may contain active and/or passive sensors, electronic and/or magnetic devices, integrated optics, or functionalized surfaces. The physical substrates that define the microfluidic device channels can be solid or flexible, permeable or impermeable, or combinations there-of that can change with location and/or time. Microfluidic devices may be composed of materials that are at least partially transparent to at least one wavelength of light, and/or at least partially opaque to at least one wavelength of light.

A microfluidic device can be fully independent with all the necessary functionality to operate on the desired sample contained within. The operation may be completely passive, such as with the use of capillary pressure to manipulate fluid flows [Juncker, 2002], or may contain an internally power supply such as a battery. Alternatively, the fluidic device may operate with the assistance of an external device that can provide any combination of power, voltage, electrical current, magnetic field, pressure, vacuum, light, heat, cooling, sensing, imaging, digital communications, encapsulation, environmental conditions, etc. The external device maybe a mobile device such as a smart phone, or a larger desk-top device.

Figure 3:
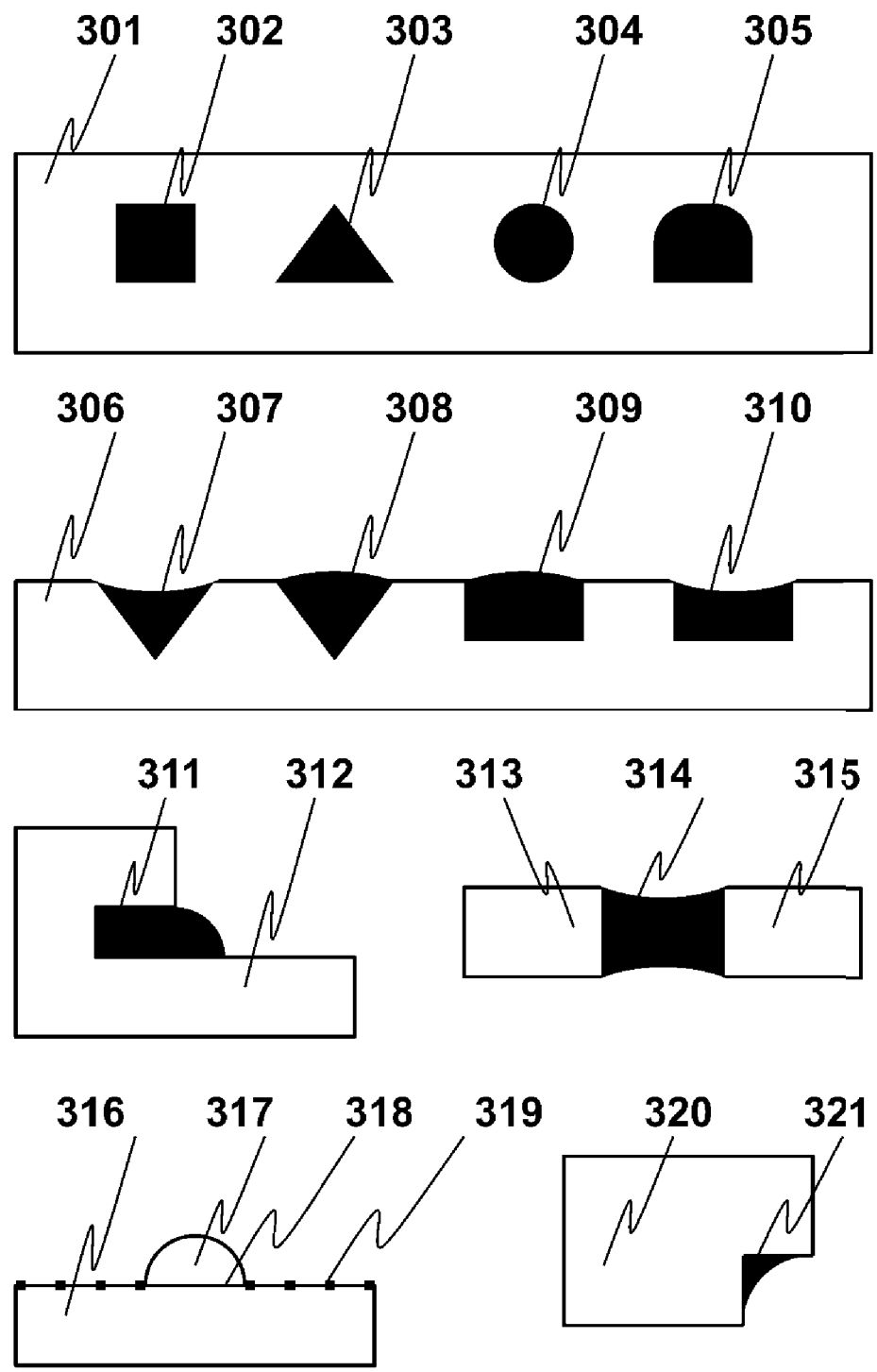
FIG. 3 demonstrates different, non-limiting embodiments of confined and non-confined channel types within a fluidic device.

The containment of the fluid within a channel can be by any means in which the fluid can be maintained within or on features defined within or on the fluidic device for a period of time. In most embodiments, the fluid is contained by the solid or semi-solid physical boundaries of the channel walls. FIG. 3 shows an example where-by channel walls with cross-sections such as rectangles (302), triangles (303), ovals (304), and mixed geometry (305) are all defined within a fluidic device (301). In other embodiments, fluidic containment within the fluidic device may be at least partially contained via solid physical features in combination with surface energy features [Casavant, 2013], or an immiscible fluid [Li, 2020]. Examples of a fluid being at least partially confined within physical boundaries include various channels physically defined on the surface of a fluidic device (306) such as grooves (307, 308) and rectangles (309, 310), all of which are filled with liquid of sufficiently minimal quantity, that surface tension allows for the liquid to be physically maintained within the channels, and not overflow. In other embodiments, the channel (311) could be a defined by a groove in a corner (312) of a fluidic device, or the channel (314) could be defined by two physically separated boundaries (313 and 315) of a fluidic device, or the channel (321) could be defined by a corner (320) of a fluidic device.

In other embodiments, the channel (317) is defined by a hydrophilic section (318) on the surface of a fluidic device (316) where-by the hydrophilic section is bounded by hydrophobic sections (319) on the surface of the fluidic device. In all cases, these embodiments are non-limiting examples.

It should be understood that some of the principles and design features described herein can be scaled to larger devices and systems including devices and systems employing channels and features reaching the millimeter or even centimeter scale channel cross-sections. Thus, when describing some devices and systems as "microfluidic," it is intended that the description apply equally, in certain embodiments, to some larger scale devices. In addition, it should be understood that some of the principles and design features described herein can be scaled to smaller devices and systems including devices and systems employing channels and features that are 100s of nanometers, or even 10s of nanometers, or even single nanometers in scale channel cross-sections. Thus, when describing some devices and systems as "microfluidic," it is intended that the description apply equally, in certain embodiments, to some smaller scale devices. As an example, a device may have input wells to accommodate liquid loading from a pipette that are millimeters in diameter, which are in fluidic connection with channels that are centimeters in length, 100s of microns wide, and 100s of nm deep, which are then in fluidic connection with nanopore constriction devices that are 0.1-10 nm in diameter.

A variety of materials and methods, according to certain aspects of the invention, can be used to form articles or components such as those described herein, e.g., channels such as microfluidic channels, chambers, etc. For example, various articles or components can be formed from solid materials, in which the channels can be formed via micromachining, film deposition processes such as spin coating and chemical vapor deposition, laser fabrication, photolithographic techniques, bonding techniques, deposition techniques, lamination techniques, molding techniques, etching methods including wet chemical or plasma processes, multi-phase immiscible medium encapsulation and the like. For patterning, a variety of methods may be employed, including but not limited to: photolithography, electron-beam lithography, nanoimprint lithography, AFM lithography, STM lithography, focused ion-beam lithography, stamping, embossing, molding, and dip pen lithography. For bonding, a variety of methods may be employed, including but not limited to: thermal bonding, adhesive bonding, surface activated bonding, fusion bonding, anodic bonding, plasma activated bonding, laser bonding, and ultra sonic bonding.

Package. A "package" is any body capable of holding contents within the defined boundary of the body. In some embodiments, the boundary is defined by a physical barrier such as a lipid bilayer or a surfactant. In some embodiments there is no barrier, such as a droplet formed by mixing two immiscible fluids. A non-exhaustive list of packages include: cells, nucleus, vesicles, exosomes, mitochondria, organelles, bacteria, virus, bubble, artificial membrane package, water-in-oil droplets, oil-in-water droplets, water-oil-water droplets, oil-water-oil droplets. In all cases, the package can be lysed (or ruptured) by various means to release the contents.

Gel. "Gels" are defined as a substantially dilute or porous system composed of a "gelling agent" that has been cross-linked ("gelled"). Non-limiting examples of gels include agarose, polyacrylamide, hydrogels [Caló, 2015], DNA gels [Gačanin, 2020]. In the context of this document, a gel and a semi-gel are equivalent, where-by a semi-gel is a gel with incomplete cross-linking and/or low concentration of the gelling agent. In some embodiments, the gel may comprise a photodegradable property. In some embodiments, the cross-linking of the gelling agent may comprise photo-activation.

Environmental Condition. An "environmental condition" may comprise any property of physics, matter, chemistry that surrounds a bio-molecule that may impact said bio-molecule's physical state, thermo-dynamic state, chemical state, or reactivity to other reagents. The impact on the bio-molecule may be due to the presence of the environmental condition, or a change in the environmental condition. An environmental condition may comprise a temperature, a pressure, a humidity level, a pH, an ionic concentration, a flow rate or direction. An environmental condition may be flux, polarization, intensity of a wavelength of light. An environmental condition may comprise a solution composition, for example a concentration of a certain reagent within a solution, or a ratio of certain reagents within a solution, or a salt composition used for a particular buffer. An environmental condition may comprise an external force acting on a bio-molecule, for example a solution or air flow rate. An environmental condition may comprise thermal conductivity property, an electrical conductivity property, an optical opacity or transparency property. An environmental condition may be an electric or magnetic field.

FRET Pair. Fluorescence resonance energy transfer ("FRET") occurs when two fluorophores (the "FRET pair") are in close proximity and when the emission spectrum of one fluorophore, the donor D, overlaps with the excitation spectrum of the other fluorphore, the acceptor A, and when D is in an excited state. The rate of energy transfer kT is given by:

$$kT = 1/\tau D (ZF/Z)6$$

where $\tau D$ is the fluorescence lifetime of D, Z is the distance between D and A, and ZF is the Forster radius. When Z=ZF, the rates of emission and energy transfer are equal, and 50% of excited donors are deactivated by energy transfer. The value of ZF is calculated from spectroscopic parameters of D and A and takes into account their relative orientation. The utility of FRET is derived from the strong dependence of the efficiency of energy transfer on the sixth power of the distance between D and A. The most efficient energy transfer occurs when the distance between D and A is close to ZF which is between two and seven nanometers for most organic fluorescent dye pairs (Wu & Brand (1994) Anal. Biochem. 218:1-13). Because of this strong distance dependence, FRET is often referred to as a "spectroscopic ruler" that is able to measure distances in the nanometer range (Stryer (1978) Ann. Rev. Biochem. 47:819-846).

External Force. An "external force" is any applied force on a body such that the force that can perturb the body from a state of rest. Non-limiting examples include hydrodynamic drag exerted by a fluid flow [Larson, 1999] (which can be imitated by a pressure differential, gravity, capillary action, electro-osmotic), an electric field, electric-kinetic force, electrophoretic force, pulsed electrophoretic force, magnetic force, dielectric-force, centrifugal acceleration or combinations there-of. In addition, the external force may be applied indirectly, for example if bead is bound to the body, and then the bead is subjected to an external force such a magnetic field, or optical teasers.

Dendrimer. The term "dendrimer" refers to a hyper-branched polymer, or body that contains a hyper-branched polymer. In certain embodiments, dendrimers, such as PAMAM dendrimers, allow precise control of the spherical polymer size.

A dendrimer comprises a dendrimer core. In certain embodiments a dendrimer core can be propargylamine, ethylenediamine, triethanolamine, pentaerythritol, azido-propyl(alkyl)amine, hydroxyethyl(alkyl)amine, tetraphenyl methane, trimesoylchloride, diamino hexane, diaminobutane, cystamine, or propylenediamine. In particular aspects dendrimer core is ethylenediamine. In some aspects the dendrimer core is at least partially composed of nucleic acid polymers. The dendrimer further comprises a repeating unit or arms. In certain aspects the repeating unit is propargylamine, ethylenediamine, triethanolamine, pentaerythritol, propylamine, propyleneimine, azido-propyl(alkyl)amine, hydroxyethyl(alkyl)amine, tetraphenyl methane, trimesoylchloride, diamino hexane, diaminobutane, cystamine, propylenediamine, and lysine. In particular aspects the repeating unit is amidoamine. A dendrimer may be a nucleic acid dendrimer. A dendrimer may be composed of combinations there-of. In certain aspects the dendrimer has a diameter of about 1 to about 1000 nm.

Fluorescently Analyzing DNA Structure in a Fluidic Slit Channel Device

Figure 4:
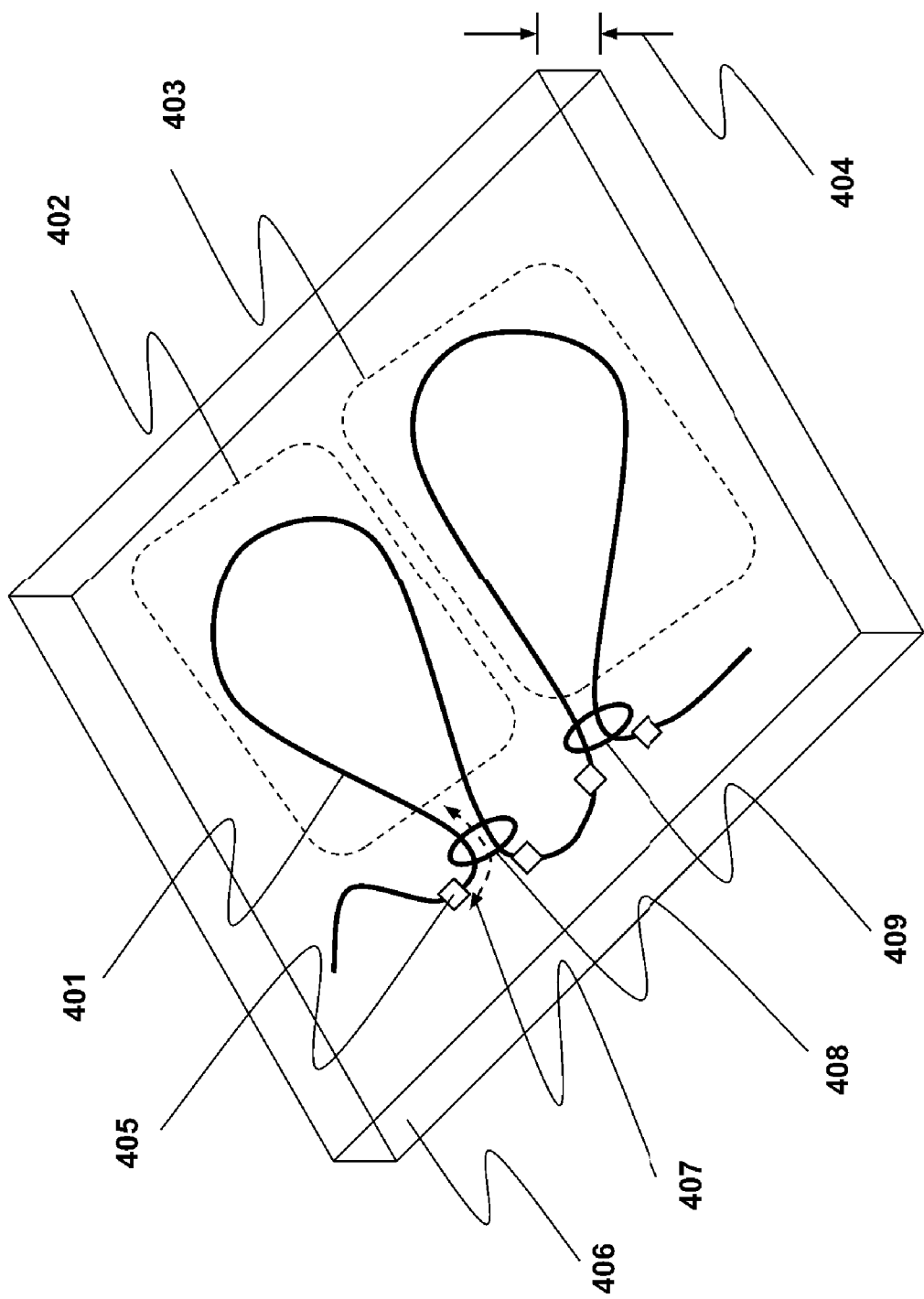
FIG. 4 demonstrates a fluidic device with a fluidic slit channel in which a long nucleic acid molecule can be elongated within the focal depth of an interrogation system, allowing for dynamic interrogation of higher order nucleic acid structures, which in this Figure are cohesin complexes.

The following set of disclosures include devices and methods for investigating a long nucleic acid molecule that comprises at least one higher order nucleic acid structures with at least one fluorescent labelling body within a fluidic slit channel device. In the preferred embodiment, at least one labelling body comprises an intercalating fluorescent dye. By fluorescent imaging a higher-order nucleic acid structure in a fluidic slit channel of a fluidic device, the state and dynamics of said structure can be controlled within the desired optical plane for interrogation, while allowing for greater flexibility of user control over the said structure's environmental conditions and reagent exposure conditions prior to and during interrogation by the interrogation system. FIG. 4 shows an example microfluidic device where-by the high-order nucleic acid structure to be investigated is vertically confined within a fluidic slit channel.

The depth of the slit may depend on a variety of factors including the focus depth of the optical interrogation system, the physical nature of the higher-order nucleic structure under investigation, or physical constraints of entropic barriers and pits used to physically control the sample. In some embodiments, the depth can be less than 5 microns, or less than 4 microns, or less than 3 microns, or less than 2 microns, or less than 1 microns, or less than 0.8 microns, or less than 0.7 microns, or less than 0.6 microns, or less than 0.5 microns, or less than 0.4 microns, or less than 0.3 microns, or less than 0.2 microns, or less than 0.1 microns, or less than 0.09 microns, or less than 0.08 microns, or less than 0.07 microns, or less than 0.06 microns, or less than 0.05 microns, or less than 0.03 microns. In some embodiments, the nucleic acid structure originates from a package that is lysed in the microfluidic device, and the contents of which are then collected within the slit. In some embodiments, the fluorescent labels and dyes are bound to the structure prior to introducing the sample the microfluidic device, while in other embodiments, the labels and dyes are bound to the structure in the device.

FIG. 4 demonstrates a particular embodiment whereby a long nucleic acid molecule (401) with a higher order nucleic acid structure is confined within a slit fluidic channel (406). In this particular embodiment, the higher order structure consists of loops (402 and 403) formed by cohesin complexes (408 and 409). In addition, fluorescent labelling bodies (405) at, or in proximity to, forward and reverse CTCF sites. The slit fluidic channel is designed to be sufficiently shallow that a portion of the structure of interest within the long nucleic acid can be maintained in an elongated state during interrogation of said portion. Interrogating a higher order nucleic acid structure with such a device and method is highly advantageous in that at least a portion of the structure of interest can be maintained within the focal depth of the interrogation system, allowing for large range associations and interactions to be observed. In the preferred embodiment, a majority of the structure can be maintained within the focal depth of the interrogation system during interrogation. In addition, the fluidic environment allows for dynamics to be captured in real-time. For example, the process of extrusion (407) of the long nucleic acid molecule through the cohesin complex can be observed, and quantified. Extrusion velocities can be determined by measuring changes in the loop size, or by including a fluorescent physical map on the molecule, or by adding labelling bodies on the long nucleic acid molecule which can act as physical reference points. In some embodiments, dynamic changes in the structure's physical conformation can be monitored in response to an introduction, or removal of a reagent. In some embodiments, dynamic changes in the structure's physical conformation can be monitored in response to a change, or maintaining of an environmental condition. The labelling bodies can be site-specific, or non-specifically bound to the long nucleic acid molecule, in order to provide land-marks for tracking. In some embodiments, such as shown in FIG. 4, site-specific CTCF forward or reverse labelling bodies can be used to monitor CTCF/cohesin complex interaction.

Figure 5:
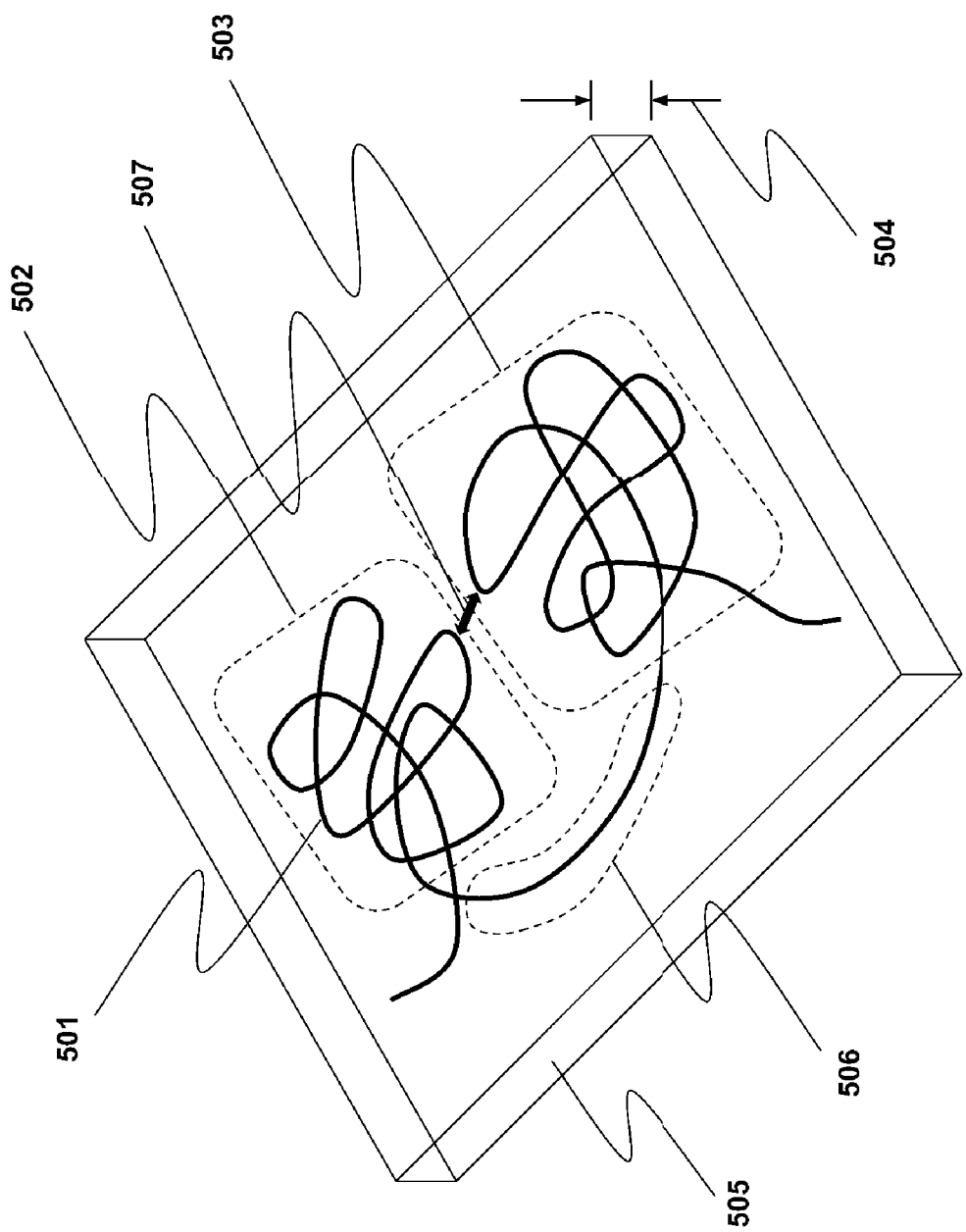
FIG. 5 demonstrates a fluidic device with a fluidic slit channel in which a long nucleic acid molecule can be elongated within the focal depth of an interrogation system, allowing for dynamic interrogation of higher order nucleic acid structures, which in this Figure are a pair of topologically associating domains.

FIG. 5 demonstrates a particular embodiment whereby a long nucleic acid molecule (501) with a higher order nucleic acid structure is confined within a slit fluidic channel (505). In this particular embodiment, the higher order structure consists of topologically associating domains (TADs) (502 and 503). The slit fluidic channel is designed to be sufficiently shallow that at least a portion of the interconnecting nucleic acid molecule (506) between the TADs can be maintained in an elongated state, allowing for the interrogation of a physical map within this region by an interrogation system. Interrogating higher order nucleic acid structures in such a device and method is highly advantageous as the interconnection regions between the TADs can be identified via the physical map by comparison to a reference, allowing for inference of the TAD's genomic composition. For example, identification of the location of the elongated portion of nucleic acid (506) via comparison of said portion's physical map to a reference allows for the determination of what portion(s) of what gene(s), promoter(s), and enhancer(s) are contained in each TAD (502 and 503). In some embodiments, the slit depth is selected to be sufficiently deep (50-2000 nm) that the TADs are capable of physically arranging to a volume similar to that in a wild cellular environment. In such a configuration, the nucleic acid within the TAD would be expected to have a high degree of non-elongated portions, making physical mapping within the TAD, or the connecting portion of nucleic acid between the TADs, challenging. However, observations concerning DNA mass, density, and physical conformation and proximity relationships concerning the TAD(s) can be performed via fluorescent interrogation. In addition, interrogation of the TAD(s) as a function of environmental conditions or changes in environmental conditions, including reagent exchanges, can be conducted. In some embodiments, the slit depth is selected such that the majority of the TAD is compressed within a 2D plane that is equal to, or less than, the focal depth of the interrogation system, as shown in FIG. 5. In this embodiment, the long nucleic acid will overlap with itself within the 2D plane, however image recognition software of the fluorescently imaged long nucleic acid molecule can be analyzed to trace the molecule's polymer chain within the image, or images. In addition, by labelling the molecule with labelling bodies to generate a physical map, proximity relationships can be inferred. For example, a proximity relationship 507 between to portions of the molecule that are different TADs.

In some embodiments wherein a portion of a higher-order nucleic acid structure is not fully contained within the focal depth of the interrogation system, multiple images may be captured at different depths of known step height (in nm), and then said images are stitched together by image analysis to generate an in-silico 3D rendering of said structure.

In some embodiments, a whole, or a part, or the higher-order nucleic acid structure can be exposed to a desired combination of reagents and environmental conditions while in the device. These reagents can include enzymes capable of modifying the structure in-situ. In some embodiments, various microfluidic features, fluid flows, and forces are used to physically manipulate and elongate the nucleic acid in the device. In some embodiments, a physical map can be generated on at least a portion of the nucleic acid that is in an elongated state. This physical map can be used as a landmark to identify the likely origin within the genome of the higher-order nucleic acid structure under investigation. In some embodiments, the physical map is generated as the structure is dynamically changing physical configuration. In some embodiments, the various microfluidic features may include pits, posts, pillars, troughs, channels, bumps, topological variations, and/or corners. In some embodiments, fluorescent probes that are bound to the nucleic acid structure can be specific, or non-specific. In some embodiments, the fluorescent probes are attached to a component of the transcription complex. Attachment can be through specific binding, or via modification and/or mutation of the components to include a fluorescent body. In some embodiments, the fluorophores used to identify different entities can be different combinations of fluorophores. In some embodiments, the different fluorophores on different entities can form a FRET pair.

Capture of Long DNA in a Porous Gel Material for 3D Analysis

In another set of embodiments, a long nucleic acid molecule comprising a higher order nucleic acid structure is fixed within a porous gel material within a fluidic channel of a fluidic device such that physical proximity relationship can be maintained for interrogation. Utilizing a fluidic device that is controlled by an interrogation system to fix a nucleic acid within a gel is highly advantageous in that such a device and method allows for the observation and selection of the time point of said structure being fixed. In addition, being fixed in a gel in a fluidic device controlled by an interrogation system allows for the control over the physical positioning of the sample to a desired location within or on the fluidic device, and allows for spatially targeting and timed control over exposure of reagents and environmental conditions to the sample, allows for automation of sample handing and interrogation, and allows for a variety of input sample types from which the long nucleic acid molecule originates.

In some embodiments, the fluidic channel in which the long nucleic acid molecule is fixed in the gel is a confined fluidic channel within the fluidic device. In some embodiments, the fluidic channel in which the long nucleic acid molecule is fixed in the gel is a non-confined fluidic channel on the fluidic device.

In some embodiments, the time point of being fixed in gel may be selected in reference to a certain event, or series of events, or combination of events. In some embodiments, the reference point may be immediately at, or approximately at, the event. In some embodiments, the reference point may be before, or after the event. In some embodiments, there may be a time duration associated, for example, 5 minutes before the event, or 5 minutes after the event.

In some embodiments, the time point of being fixed in the gel may be selected in reference to a certain time point of a cell cycle, for example when the cell is in interphase, or prophase, or prometaphase, or metaphase, or anaphase, or telophase. In some embodiments, the time point of being fixed in the gel may be selected in reference to a certain checkpoint of the cell. In some embodiments, a fixation in gel may be selected in reference to a certain time point of the cell's life, for example during apoptosis. In some embodiments, the time point of being fixed in the gel may be selected in reference to a certain time point of when a cell undergoes a specific change in morphology, for example blebbing, plasmolysis, karyorrhexis, pyknosis, endocytosis, phagocytosis, budding/lysis during viral particle secretion or DNA fragmentation. In some embodiments, the time point of being fixed in the gel may be selected in reference to a time point of when a nucleic acid structure in a cell undergoes a change in physical composition, morphology, density, conformation, or topology. In some embodiments, the time point of being fixed in the gel may be selected in reference to a time point of when a cell undergoes a certain enzymatic activity, for example transcription, replication complex formation or deconstruction, loop extrusion, gene regulation, formation or deconstruction of a transcription complex, formation or deconstruction of chromosomal condensation or compaction, sister chromatids resolution. In some embodiments, the time point of being fixed in the gel may be selected in reference to a time point when a package or long nucleic acid molecule is exposed to a certain reagent, or combination of reagents, or concentration of reagent. In some embodiments, the time point of being fixed in the gel may be selected in reference to a time point when a package or long nucleic acid molecule is exposed to a certain environmental condition or change in environmental condition. In some embodiments, the time point of being fixed in the gel may be selected in reference to a time point when a package or long nucleic acid molecule is exposed to a certain protein, enzyme, or exogenous nuclei acid such as viral genome integration, or extrachromosomal viral episome physical docking to host chromosomes through EBNA1-binding sites.

Figure 6:
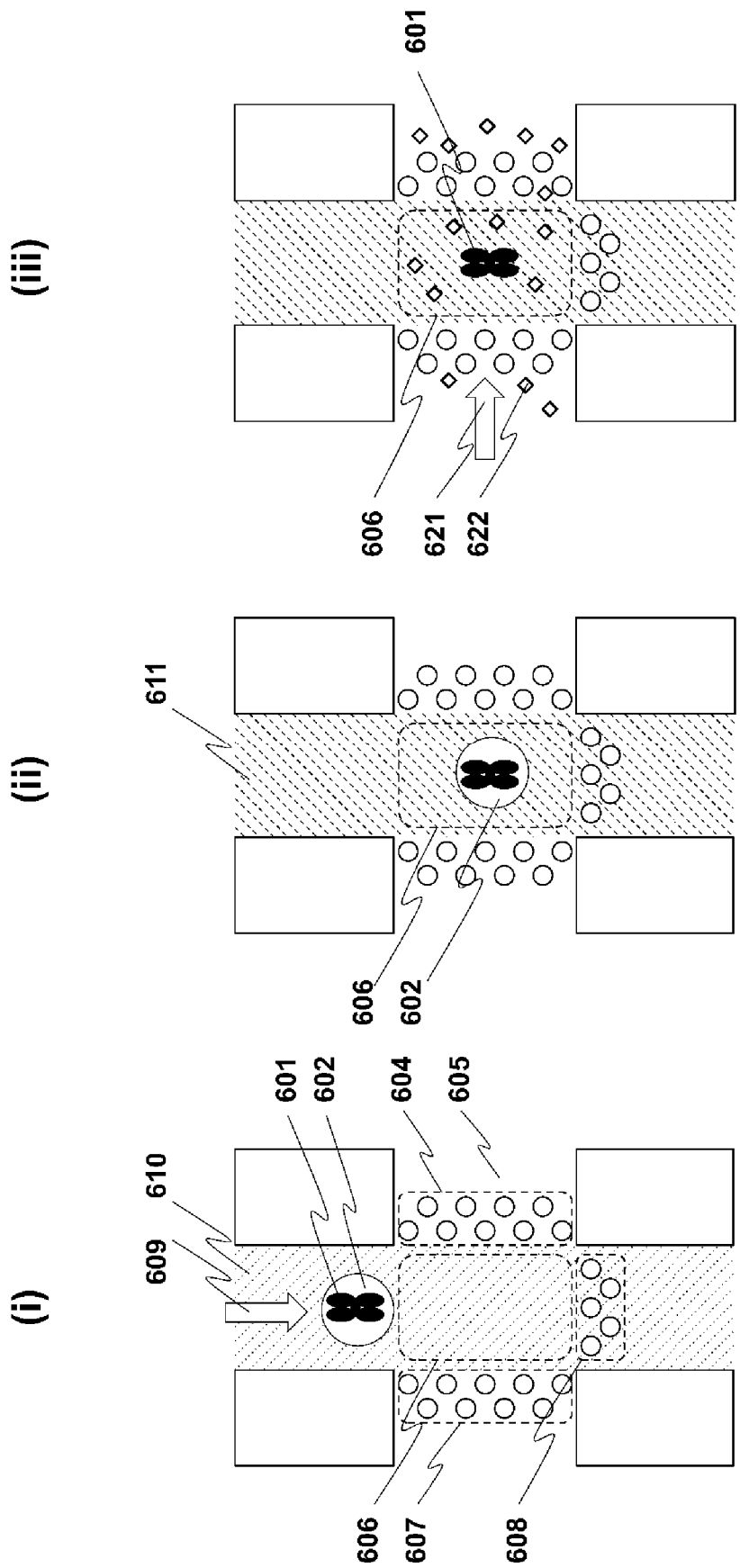
FIG. 6 demonstrates a fluidic device comprising an intersection of two fluidic channels, such that a cell containing chromosomes can be identified, lysed, and have the chromosomes fixed in a porous gelled material. The fluidic device enables flexible exposure of the chromosomes to arbitrary reagents both before, and after fixation in the gel. (i) A cell enters the device via the primary channel (ii) The cell is maintained in the intersection by the filtering features, and the surrounding gelling agent is gelled into a porous gel material. (iii) The cell is lysed via lysing agents flowing from the secondary channel, leaving the cell's chromosomes fixed in the gel.

FIG. 6 demonstrates an embodiment device and method of fixing a long nucleic acid molecule in a gel based on observations of the cell. At time point (i), a cell (602) containing at least one long nucleic acid molecule (here a chromosome: 601) is flowed (609) through a first fluidic channel (610) that includes a gelling agent in the buffer. In this embodiment, the first fluidic channel (610) intersects (606) with a second fluidic channel (605), and surrounding all exits of the intersection are fluidic filtering features (607, 608, 604) that have fluidic openings between the filtering features, wherein the fluidic openings between the filtering features are small enough to block said intact cell or long nucleic acid molecule from passing through, unless a sufficiently large external force is applied on said intact cell or long nucleic acid molecule. At a later time point (ii), the cell will enter the intersection region (606) and become trapped unable to progress through the filtering features, however the filtering features will allow for solution and reagent exchange in the intersection. The cell is then observed via interrogation with an optical interrogation system until the desired time to be fixed has been reached. In some embodiments, the reagent and environmental conditions may be maintained or altered during the observation. In some embodiments, the cell or molecules and entities within the cell may be stained or labelled with a dye, either before entry into the intersection region, or after entry into the intersection region. The dye may be fluorescent or non-fluorescent in nature. When the desired time point has been achieved, the gelling agent is then gelled, resulting in a porous gel material in the primary channel (611). Next (iii), by flowing (621) reagents (622) through the secondary channel into the intersection region (606) the cell can be lysed, with the non-chromosomal material removed, and the remaining chromosomal material remaining fixed in place in the gel. The long nucleic acid material can then be further processed while fixed in the gel, including reagent exposure, maintaining or changing environmental conditions, and interrogated.

In some embodiments, the roof of the fluidic channel is porous or removable. Thus a secondary channel is not necessary for reagent exchange. For embodiments where-by the roof is porous, reagent exchange may be done through the roof, either by flow or diffusion. For embodiments where-by the roof is removable, for example a PDMS roof bonded to a silicon oxide fluidic device, the roof may be removed after gelling of the gelling agent to allow for regent exchange directly with the material in the gel via diffusion.

In some embodiments, there are no fluidic filtering features (607, 608, 604) in the fluidic device. The package or long nucleic acid molecule is flowed in the primary channel with a gelling agent, and the flow is stopped when the package or long nucleic acid is positioned in the intersection (606), and then the gelling agent is gelled, allowing for reagent exchange through the porous gel via the secondary channel.

In some embodiments, a least one long nucleic acid molecule is selected from a population of long nucleic acid molecules, via an analysis of the interrogation data, to be fixed in a porous gel. In some embodiments, a population of long nucleic acid molecules are fixed in a gel, and a selection criteria is used to remove at least a single molecule from the population, or at least one portion of at least one single molecule from the population.

In some embodiments, the selection criteria comprises an analysis of a physical map. In some embodiments, the physical map is compared to a reference. In some embodiments, the physical map is associated with the at least one long nucleic acid molecule that is selected. In some embodiments, the physical is associated with at least one long nucleic acid molecule from the population of molecules that are not selected. In some embodiments, the selection criteria comprises the presence or absence of a labelling body on a long nucleic acid molecule.

In some embodiments, at least one package containing at least one long nucleic acid molecule is selected from a population of packages. In some embodiments, the package selection criteria is informed at least in part by an analysis of the interrogation data. In some embodiments, the package selection criteria comprises the presence or absence of at least one labelling body. In some embodiments, the package selection criteria comprises the package morphology, or package type, or originating tissue type, or disease type, or association with a disease, or state of a cell cycle.

In some embodiments, the long nucleic acid molecule within the porous gelled material undergoes at least a portion of any of the proximity 3D mapping processes (see definitions) while in the gel. Such processes may include a reagent exchange, an environmental condition, a cross-linking reaction, a digestion, a restriction cleaving, an enzymatic reaction, or a ligation.

In some embodiments, the long nucleic acid molecule within the porous gelled material undergoes at least a portion of any of the 3D physical mapping processes (see definitions) while in the gel. Such processes may include a reagent exchange, a hybridization of tags, binding of a labelling body, hybridization of a primer, hybridization of a barcode, a enzymatic process such as ligation, digestion, nicking, restriction cleaving, or polymerization, an environmental condition. In addition, optical interrogation or cycling of the various reagents with a 3D physical mapping process can be conducted wholly, or partially while the long nucleic acid molecule is fixed within the gel.

Figure 7:
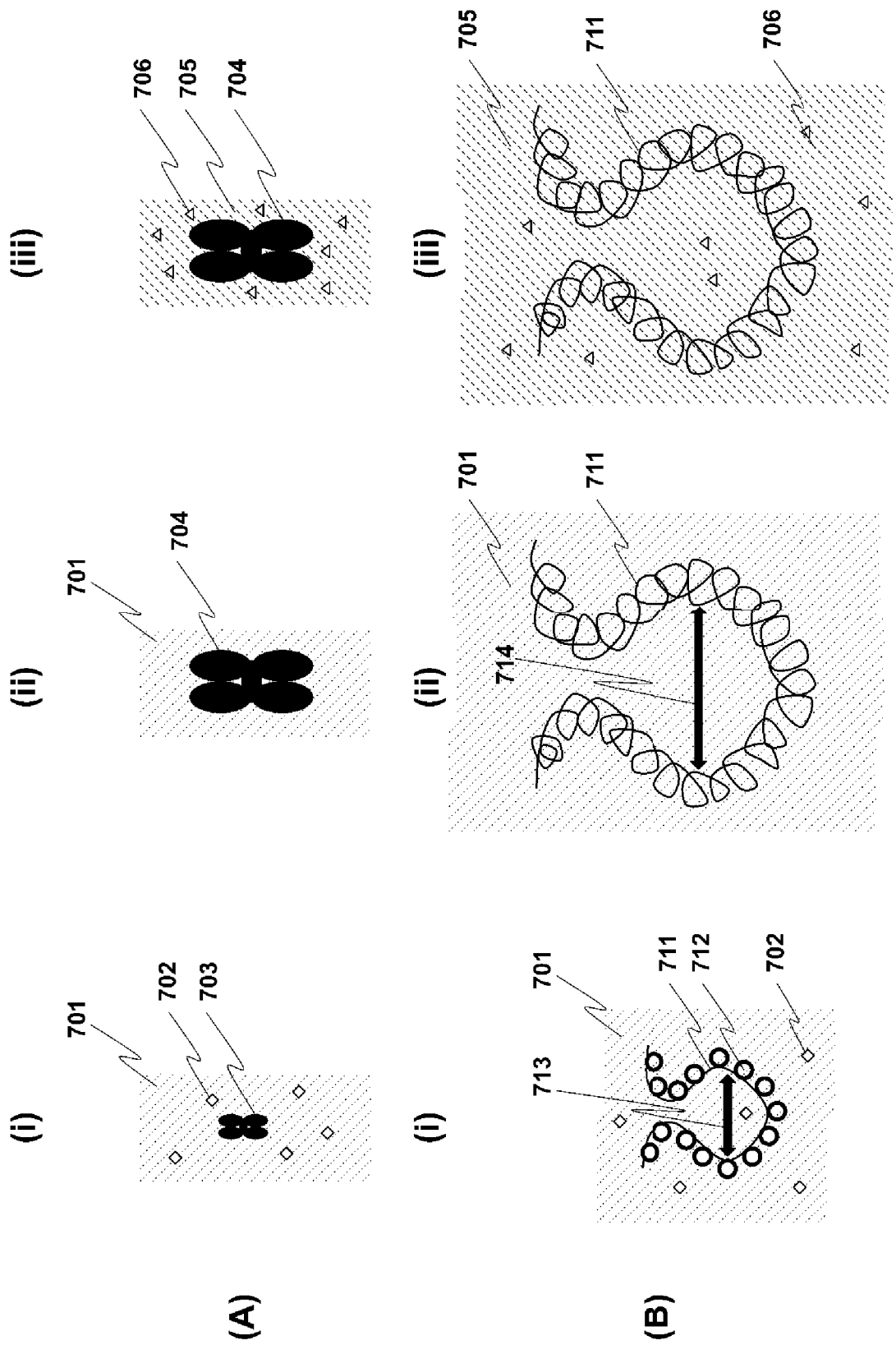
FIG. 7(A) demonstrates a chromosome being swollen and then fixed in a porous gel material to enable controlled exposure of the chromosome to a reagent in a swollen, fixed state. (i) A chromosome in the presence of a protein digestion enzyme and a solution containing a gelling agent. (ii) The chromosome swells with the digestion of the proteins. (iii) The gelling agent is gelled, fixing the swollen chromosome in a gel.
FIG. 7(B) demonstrates a zoomed in schematic of FIG. 7(A). (i) a portion of chromatin from the chromosome is exposed to a protein digestion enzyme, such that post-digestion (ii) the portion of the chromosome swells, and is then (iii) fixed in a porous gel material.
Figure 8:
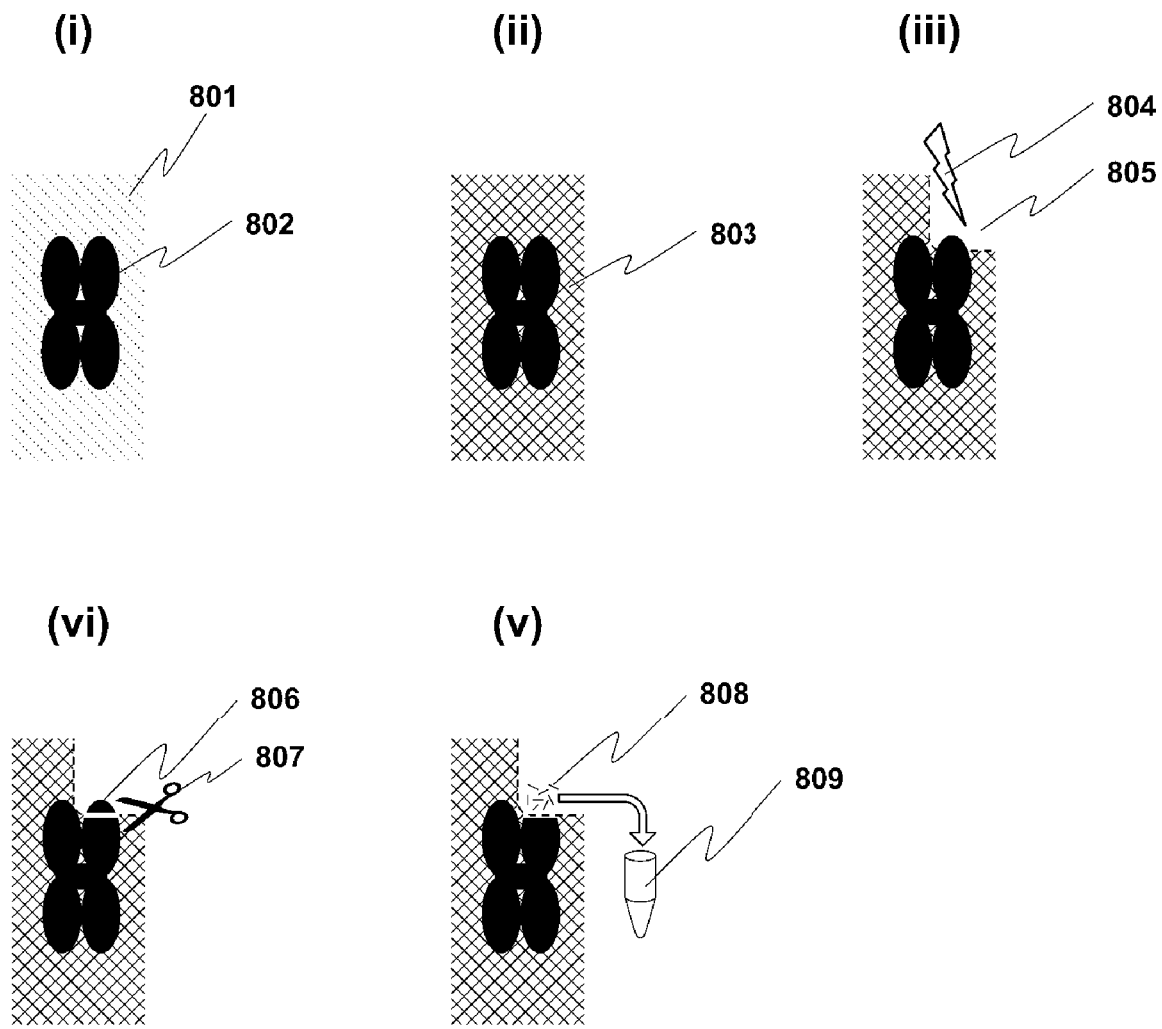
FIG. 8 demonstrates an example of selectively extracting a portion of a chromosome that is fixed in a gelled material.
Figure 9:
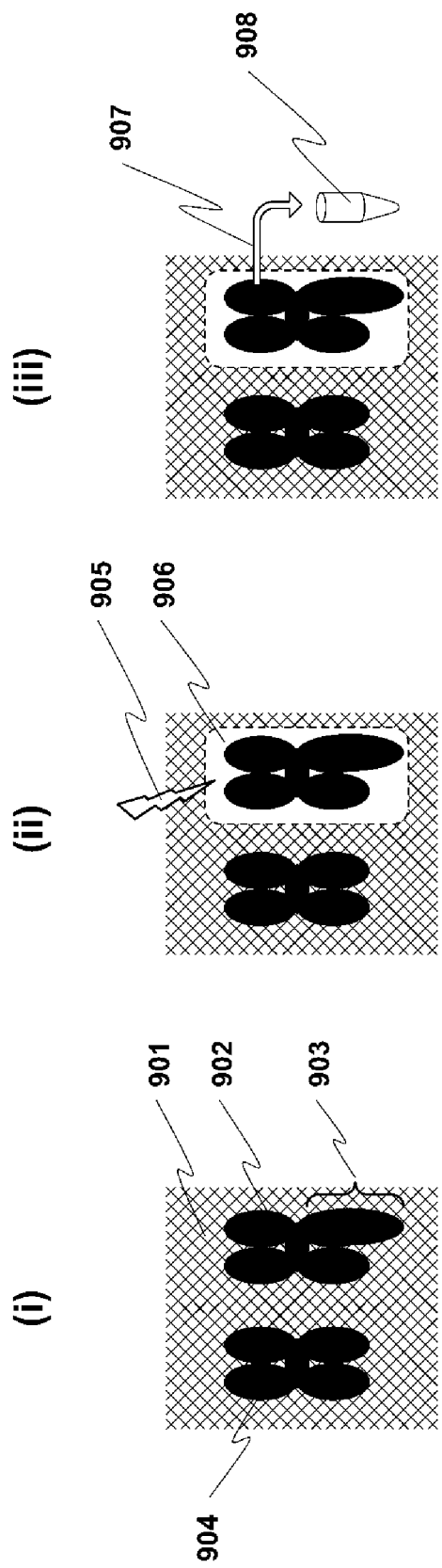
FIG. 9 demonstrates an example of selectively extracting a chromosome in its entirety that is fixed in a gelled material.

In some embodiments, the long nucleic acid molecule is at least partially removed of protein via protein digestion or protein denaturation, for example with proteinase k, or more targeted relaxation such as treatment with TOPO II, Wapl, before or after fixing in the gelled material. In some embodiments, at least a portion of a chromosome is exposed to a protein digestion or denaturation under nonturbulent conditions such that the chromosome is allowed to swell to a larger physical size within a fluidic channel or chamber of the fluidic device via polymer self-avoidance to minimize entropy, after which the expanded chromosome is then fixed in a porous gel. In the preferred embodiment, environmental conditions are maintained or modified during the swelling process to approximately, on average, maintain the proportionality of the proximity relationships within the chromosome. In some embodiments, this modification of environmental conditions is controlled via a feedback system, which is at least partially informed by data generated from optically interrogating the chromosome during the swelling process. FIG. 7(A) demonstrates this embodiment, whereby (i) a long nucleic acid molecule (here a chromosome in metaphase 703) is in a fluidic channel (701) of a fluidic device and exposed to a protein digestion enzyme (702). After digestion of the proteins, (ii) the chromosome swells in size from the original volume (704) due to polymer self-avoidance. Once swollen, (iii) the gelling agent in channel that surrounds the chromosome is gelled, allowing for reagent exchange (706) to partake in reactions with said swollen chromosome while said chromosome remains fixed in the porous gel (705). In some embodiments the gelling agent is introduced prior to protein digestion or denaturation. In some embodiments, the gelling agent is introduced after the protein digestion or denaturation.

FIG. 7(B) demonstrates a zoomed in description of FIG. 7(A), whereby (i) a long nucleic acid molecule (here chromatin comprising chromosomal nucleic acid (711) which is maintained in a dense configuration by nucleosomes (712)) is in a fluidic channel (701) of a fluidic device, and exposed to a protein digestion enzyme (702) that digests the nucleosomes. After digestion of the proteins, (ii) the chromosomal nucleic acid is released from the nucleosomes and swells a multiple of the original volume such that there is a distance relationship between two points that increases from prior digestion (713) to post digestion (714). Once swollen, (iii) the gelling agent that surrounds the nucleic acid (711) is fixed in gelled, allowing for reagent exchange (706) to partake in reactions with said swollen chromosome while said chromosome remains fixed in the porous gel (705).

Interrogating a swollen chromosome while fixed in a porous gel is particularly advantageous for 3D physical mapping applications wherein multiple fluorescent signals are interrogated simultaneously, and each signal corresponds to a specific location on the chromosome. First, by swelling the chromosome, the number of independent simultaneous measurements that can be performed increases as there is an inherent limit to the density of such measurements that can be performed within a volume for any given optical interrogation system. Second, distance measurements between two fluorescent signals that would normally be too close to optically resolve, may become resolvable after swelling. By measuring the degree of swelling of the chromosome, measured distance lengths can be corrected to their original value prior to swelling. In some applications, the absolute distance between two locations within a chromosome before swelling is estimated as least in part by using optical interrogation data of the chromosome during or after the swelling process. In some applications, only the relative position of location within a swollen chromosome is required.

In some embodiments, the nucleic acid molecules are removed from the device, and the 3D mapping reactions are performed externally. In some embodiments the nucleic acid molecules are exposed to at least one type of restriction enzyme to cleave the molecules in multiple locations. In some embodiments, after cleaving, on at least one pair of the cleaved ends a barcode is ligated, bound, attached, or incorporated. In some embodiments, the barcode is unique for nucleic acid originating from a single-cell. In some embodiments, the fluidic device is capable of capturing and maintaining physical separation of at least two different cells.

Generation of Spatially Resolved or Sub-Chromosomally Sampled Genomic Libraries by Embedding Chromosomes in a Photodegradable Matrix A method is presented for selective separation of a portion of nucleic acids from a whole population by embedding the population in a photocleavable or photodegradable matrix (901), preferably a photocleavable or photodegradable hydrogel, then subsequently releasing only a subset of the population on the basis of spatially limited photodegradation (905) of the hydrogel. Once the hydrogel is eliminated from the region proximal to the nucleic acid (906) it is accessible to enzymatic, chemical and mechanical manipulation, including removal (907) to a unique container (908). Non-limiting applications are to extract DNA present in an intact nucleus, a lysed nucleus, a chemically fixed or partially chemically fixed nucleus, a swollen nucleus, a swollen nucleus embedded in a matrix. Additional non-limiting applications include isolating partially condensed or fully condensed chromosomes deposited on a flat surface, structured surface, fluidic device or three dimensional device, alternately extracting RNA deposited throughout a cell, fixed cell, lysed cell or cell swollen in a matrix as in the practice of expansion microscopy. The method can be more broadly used to spatially dissect a fixed cell nucleus or intact cell.

In some embodiments, a method of isolating at least a portion of a chromosome from a population of chromosomes, wherein (a) the population of chromosomes are fixed in a photodegradable gel, (b) said fixed chromosomes are interrogated with an optical interrogation system and at least a portion of a chromosome is selected based on selection criteria informed at least partially from said interrogation, and (c) said portion is isolated from the population by targeted photo-degradation of the gel fixing said portion of chromosome, and then (d) eluting the selecting portion away from the remaining fixed population and collecting it. In some embodiments, the selected at least one portion of the chromosome is photo-cleaved from its originating chromosome. In some embodiments, the selected at least one portion of the chromosome has at least one bound labelling body. In some embodiments, said fixed chromosomes in a gel are exposed to at least one reagent. In some embodiments, said fixed chromosomes in a gel are exposed to at least one environmental condition. In some embodiments, said gel is a hydrogel. In some embodiments, said gel is a photodegradable gel. In some embodiments, the selected at least one portion of the chromosome comprises an elongated long nucleic acid molecule. In some embodiments, the selected at least one portion of the chromosome comprises a physical map. In some embodiments, a comparison of said physical map to a reference at least in part informs the selection criteria. In some embodiment, the physical map is a linear physical map. In some embodiment, the physical map is a 2D physical map. In some embodiments, the physical map is a 3D physical map. In some embodiment, the chromosomes are combed on a substrate, in a fluidic device, or on a fluidic device prior to being fixed in a gel. In some embodiments, the chromosomes are at least partially elongated in a fluidic channel within a fluidic device, or on a fluidic device, before being fixed in a gel.

Preferred embodiments take condensed chromosomes and deposit them on flat or structured glass or polymer substrate, and manipulate them to selectively isolate DNA present in one or more specific chromosomal locations. This embodiment utilizes the wide body of knowledge of cytogenetic analysis in order to prepare spreads of chromosomes, stain them, and analyze their banding patterns to detect high order structural variations. The embodiment builds upon this by allowing a cytogeneticist, other scientist or automated instrument to interrogate chromosomes containing at least one labeling body, compare against a reference in order to select individual molecules, portions of individual molecules, multiple portions of individual molecules or multiple portions of multiple molecules to analyze further by selectively isolating that region of interest, possibly by generation of a DNA sequencing library from the region of interest.

The method relies on the ability to specifically break apart a matrix in a high resolution manner by focusing visible or ultra violet radiation onto a photosensitive matrix. In the preferred embodiment the matrix is a photodegradable hydrogel described below. The method also relies on the coupling of an interrogation system, preferably consisting of microscope containing brightfield optics, most preferably consisting of a fluorescence interrogation system consisting of brightfield optics in combination with fluorescent optics, with a photodegradation system described below.

The method can be performed with varying degrees of automation. The following embodiment is disfavoured in that it does not scale well to multiple samples, is inconvenient for the operator and is likely to have incomplete mass transfer of isolated nucleic acids, but it is presented to illustrate that automation is not essential for the basic technique: An operator of a manual microscope can observe the sample using light that will not cleave the matrix and can manually position a microscope stage relative to a pre-calibrated location. The operator then turns on a light source to direct visible or ultraviolet radiation toward the portion of the matrix that is at the pre-calibrated location. Subsequently the operator takes a manual pipette and fluidically manipulates the site of irradiation to manually aspirate nucleic acid that has been liberated from the matrix. The operator then transfers the contents to a microcentrifuge or equivalent tube and proceeds to use a commercially available sequencing library kit to prepare a DNA sequencing library from the sample according to manufacturer's protocols.

In a more preferred embodiment, automation assists the user to more precisely target a region of interest, for example by integrating a precisely timed light pulse in an arbitrary shape to target the focused light onto the sample to initiate matrix photodegradation. The system could collect a series of samples from an immediate vicinity, for example a user could identify a center of region of interest as a circle of a defined radius, a polygon, or a free-form shape by tracing a pattern over an image of the sample. The instrument could collect the entire region in one pass, or it could manually or in an automated fashion subdivide the region into multiple subregions and perform sequential extraction of each subregion to increase the spatial sampling resolution.

In some embodiments the instrument could collect a multiplicity of samples by sequentially photodegradation the matrix in a systematic manner, for example by taking a thin sample and raster scanning it in two dimensions or by dividing a thick section into a three-dimensional volume. Certain sampling geometries are advantageous to maximize stability of the residual, intact matrix and minimize crosstalk between sampling locations, but the benefits of the overall technique can be enjoyed when samples are subdivided into a variety of geometric shapes and each section sampled in a variety of orders.

In some embodiments an entire single chromosome (902) could be selected from a population of chromosomes (904 and 902) such as a chromosome spread from a single cell. The chromosomes could be selected based on interrogation to identify one of more labeling bodies such as Giemsa bands or alternately they could be subject to fluorescent interrogation to identify the presence of a fluorescent labeling body such as a FISH probe. For example, a chromosome could be selected on the basis of it having an abnormally large arm (903) due to an insertion. In other embodiments an operator or automated instrument could repeatedly identify and select the same chromosome from a multiplicity of cells, for example multiple copies of chromosome 7 that were observed from cells isolated from a human patient could be isolated and extracted together and pooled or isolated one by one for separate downstream analysis. In other embodiments a portion of a chromosome could be isolated, not limited to one or more teleomeric regions, entire sister chromatids, centromeric regions, entire arms, portions of arms, or any combination of the above.

In some embodiments the method could be used subsequent to karyotyping in order to perform a follow on diagnosis of potential structural variations observed by karyotyping, or to analyze specific sites suspected of harboring a structural variation based on prior information about the sample or patient.

In other embodiments, DNA sequences could be identified by sequence specific means and used to direct isolation of DNA. For example a FISH probe specific to viral DNA that has integrated in a host genome could be used to identify regions of single chromosomes where it had integrated. The fluorescence signal acquired by the fluorescent interrogation system would then be used to target hydrogel photodegradation around that location and the sample collected to further characterize the integration site using short read sequencing.

In other embodiments the method of downstream analysis of the selected portion of the sample could include generation of physical maps, either by moving the sample to another fluidic device or surface or by moving the sample to an adjacent portion of the same device.

In some embodiments the method could be used in concert with a fluidic device which contained multiple samples and one or more interrogation regions or manipulation regions. By selectively liberating only portions of the analyte, possibly based on imaging of the analytes, the method could allow only certain copies of the analyte to progress through the device and enter the interrogation region or manipulation region.

In other embodiments, cells in culture or intact tissue could be fixed and the photodegradable matrix placed over them. The cells could then be selectively sampled by removal of the matrix. This could occur in a blind fashion for example by placing a N×M grid of sampling locations over the sample, or could occur in a more coordinated manner, for example by sampling a brain histology slice at intervals along the dorsal ventral axis. Single or multiple neurons could be sampled along the length of their projections and mRNA isolated at various points along the projections for analysis by RNASEQ.

In other embodiments a cell nucleus could be fixed with a fixing agent, preferably formaline, and photodegradable hydrogel polymerized around the nucleus. Through successive steps of photodegradation, chromatin degradation and elution and sample aspiration, the nucleus could be dissected one voxel at a time and DNA libraries could be constructed from each voxel. Comparison of the sequencing data would allow construction of a map of genomic content. Preferably, the Hi-C method of high resolution genome spatial tagging is done prior to hydrogel polymerization, and the combination of voxel data and Hi-C data are used to create a high resolution 3D map.

Chromosome Anti-Contraction Methods

The genomic resolution of photodegradable hydrogel isolation and release depends on the density of the nucleic acids in basepairs per square micron in the case of 2D release or basepairs per cubic micron in the case of a 3D release. Methods to lower the density as described below will allow finer genomic resolution.

The degree of swelling or contraction of a long nucleic acid or nucleic-acid:protein complex can be controlled by well established methods, as evidenced by an extensive volume of laboratory protocols for cytogentic analysis of chromosomes [Lawce 2017]. Chromosomes progress through various stages of compaction during the cell cycle, from diffuse interphase heterochromatin to tightly bound sister chromatids during prometaphase. The addition of the small molecule Colcemid is able to have a dramatic effect on the size of observed chromosomes by blocking cell cycle progression and leaving chromosomes in a condensed state with sister chromatids attached. The degree of compaction of chromosomes, and hence the banding patterns observed during G-banding and other types of cytogenetic analysis, have a strong effect on the clinical utility of the prepared chromosomes. The need to modulate the degree of compaction, which is often measured as the total number of chromosomal bands per haploid set detected, has led to a wide variety of protocols to modulate compaction.

Finer control of chromosome size can be achieved by two classes of complementary laboratory methods [Lawce 2017]. First, alternate cell cycle synchronization methods are gentler, such as the addition of Methotrexate to interrupt the purine pathway followed by the addition of Thymidine to release the cells from the block. Synchronized cells can then be arrested with much lower concentrations of Colcemid, which produces more swollen chromosomes than Colcemid alone, or cells can simply be harvested when chromosomes are observed to be suitably compact. A second class of methods treats chromosomes with various chemical agents such as colchicine, velban, ethidum bromide, Actinomycin D, acridine orange, Hoechst 33258, DAPI, distamycin A, 5-azacytidine, 9-Aminoacridine, and BrdU. The identity and concentration of salts also has been used to modulate chromosome morphology, including KCl, Ohnuki's hypotonic solution, dilute Hanks' BSS, and Sodium citrate. Further methods loosen chromatin by means of proteolytic digestion. This can be accompanied by methods to disentangle crossed DNA strands by the addition of topological enzymes such as Topoisomerase II.

Exemplary high resolution chromosomal banding is demonstrated by [Drouin 1991] at the 1000 band per haploid set level, where after careful cell cycle release with thymidine, chromosome spreads are prepared and banded, resulting in elongated chromosomes with a swollen linear density of between 5-10 MB/micron depending on sequence.

Chromatin Disruption and DNA Fragmentation

Even after condensed chromosomes are partially liberated from the hydrogel, the covalent bonds holding together DNA, topological interactions amongst DNA and non-covalent linkages of protein/nucleic acid complexes that make up chromatin will keep DNA from freely diffusing away. These interactions need to be broken before nucleic acids can be released, and the manner in which they are broken has impacts on the suitability of the products for downstream processing.

In one embodiment where the application is to create a focused short read sequencing library, DNA is stained with the intercalating dye YOYO-1 prior to photodegradation of the hydrogel. After each step of hydrogel photodegradation, the same region is irradiated with 488 nm light to further stimulate DNA cleavage via radical damage. Depending on the wavelength of light used to photodegrade the hydrogel, YOYO-1 might already have started to degrade DNA and subsequent irradiation is not necessary.

In the most preferred embodiment, after every course of degradation a cocktail of trypsin and NEBNext dsDNA Fragmentase (New England Biolabs) as flowed over the exposed nucleic acids and or chromatin and incubated at 37 C for 10 mins.

In other embodiments, protease and endonucleases are added to solution while tethered to microbeads which impede their ingression into the still polymerized regions of the hydrogel.

In other embodiments, the nucleic acids and or chromatin are partially or wholly digested by proteases and endonucleases prior to encapsulation by hydrogel. This can be done at a low pH to enhance nucleic acid affinity to the substrate and prevent DNA elution, and the pH can subsequently be raised after the sample is fully embedded in the hydrogel.

Fragmentation of DNA for genomic library construction or other downstream analysis methods can occur by a variety of means, not limited to mechanical disruption, hydrodynamic shearing, nebulization, disruption from acoustic waves or focused acoustic waves, restriction endonuclease digestion, nickase and single stranded nuclease digestion, photocleavage from accumulation of single-strand nicks from fluorescent photocycling of an intercalating fluorophore with or without a single-strand nuclease, and transposase cleavage and insertion. The liberation and fragmentation of DNA from the chromosome is assisted by the digestion of chromatin proteins coating the DNA by means of proteolytic enzymes not limited to proteinase K or trypsin.

Photodegradation System

An optical device embodiment wherein photodegradation of a photodegradable hydrogel matrix by delivering light of a specific wavelength and fluence to a precisely defined area whose coordinates are known relative to a record of an interrogation event from an interrogation system.

Here in this document, "high resolution" refers to the ability to selectively release and recover a portion of a nucleic acid which is within 1 micron of a portion of the nucleic acid that remains attached to a support. The process can be repeated to sequentially liberate adjacent sections, such that the material is systematically dissected and separated. Here the 1 micron specification means that >80% of nucleic acid is retained in one area of a device but 1 micron away <20% of the nucleic acid has been removed. In other embodiments the resolution is 2 microns, 4 microns, 8 microns, 16 microns, 32 microns, 500 nm, 250 nm, 125 nm, 63 nm, or 32 nm.

Optically, there are variety of ways by which light can be directed to the hydrogel in order to photodegrade it in a high resolution manner. High resolution requires high NA illumination such as is routinely achieved by well corrected imaging objectives. In one non-limiting embodiment a Nikon 60× 1.4 NA VC is used for both imaging with red light, which does not appreciably photodegrade an oNB derived hydrogel matrix, and also for irradiation with UV or violet light. The illumination pathway illuminates a digital micromirror device and then images it to the sample such that the central portion of the device is the same size as the portion of the image that is visible to the primary detection camera. For example, this would comprise imaging the central 2048×2048 pixels of the 0.47 inch diagonal DLP471TP device (Texas Instruments), which corresponds to a magnification of 1/60×. To achieve full optical resolution imaging of the device, it is illuminated with a numerical aperture>the objective NA/magnification (1.4/60=0.023) and the pupil is approximately imaged to the objective rear pupil. By setting the on or off state of each pixel in the digital micromirror device and then applying a dose of photodegradation light, it is possible to selectively illuminate an arbitrary pattern of the hydrogel.

In an alternate embodiment, a collimated laser beam can be used to photodegrade the sample, and the beam is directed to the region of interest by a combination of galvo mirrors and laser intensity modulation as is known for confocal microscopy.

Since high NA light fans out after it goes through focus, the area of hydrogel which is cleaved is not precisely resolved beyond the depth of focus. This is not a problem for thin samples that can be compressed in a thin flow lane (<2 um) as part of a flowcell, or samples that do not extend far from the glass in an axial direction. For thicker samples, lower NA light can be used in order to obtain more uniform resolution as a function of sample depth. In addition to or in concert with lowering the NA, beams with a Bessel function profile can be used in order to obtain an extended depth of field. Such beams can be generated for example by use of diffractive or refractive axicon lenses. Other embodiments avoid axial spread by utilizing focused two-photon excitation such as focusing femtosecond pulses from a Ti: Sapphire laser.

Other embodiments utilize TIRF excitation to prevent light from freely propagating through the medium. TIRF illumination can be classically achieved by focusing a laser at the back focal plane of the objective, off axis by an amount d>(focalLength_objective)×(NA_sample). The laser can continuously strike this region or can move around in a circle to lessen illumination artifacts. Structured illumination can be achieved by splitting the beam into more than one beam and launching them together through opposite sides, or other appreciably different locations, as long as they are all far enough away from the optical axis to obey the inequality above.

Other embodiments change the TIRF illumination setup to only illuminate a tightly focused area, by means of launching a hollow cylinder of collimated light into the objective. Non-limiting means of achieving this include launching a wide, collimated laser at the objective after passing through an annular stop, or alternately using a diffraction limited off axis parabolic mirror with a hole in the middle to collimate laser or LED light that emerged from a single mode fiber or pinhole aperture. Imaging light would pass through a hole in the middle of the off axis parabola that was parallel to the collimated beam. Other embodiments could launch a laser through a pair of positive and negative axicon lenses to create a collimated ring beam. Alternate embodiments could combine the two approaches to allow electronic selection of either mode, for example in the case of the double axicon example by mirror combining both a fiber tip as well as a tapered light guide that acts as a light pipe homogenizer.

In the case of TIRF or two photon photodegradation illumination where there is axial suppression of the hydrogel dissection beam, it is possible to systematically slice the hydrogel apart in 3 dimensions. TIRF will only act on the portion of the hydrogel adjacent to the coverglass, and this is also the preferred direction for multiphoton excitation due to beam quality deterioration with increased sample penetration. The plane next to the cover glass can be dissolved all at once with standard TIRF, or in a raster scanning motion with focused TIRF. After a plane has been dissolved, there is a fluid layer between the coverglass and the sample. The sample can then be moved towards the sample by means of mechanical compression.

Hydrogel Photochemistry

Photodegradable hydrogels [Kloxin 2009] are used in tissue engineering, 3D printing of tissues and organs, investigations of mechanical environment in cell signaling, burn care and drug delivery systems. Methods for forming gels and applications are reviewed in Koetting 2015 and all references are incorporated herein.

Multiple routes exist to creating photodegradable hydrogels. In the most preferred embodiment PEG molecules are polymerized together using reactive groups that also contain an ortho nitrobenzyl photodegradation group. What is meant by photodegradation is the breakage of crosslinking molecules that are required for the structural integrity of the hydrogel. In this case, irradiation with longwave UV (365-405 nm) cleaves the ortho nitrobenzyl groups, releases modified PEG monomers and destroys the gel crosslinking. For example, [Kloxin 2009] demonstrate hydrogels polymerized using a crosslinker containing PEG-bis-amine that is bis functionalized with a photodegradable acrylate pendant via a peptide linkage. The gel is created by redox-initiated free radical polymerization in dark conditions and three dimensional shapes can be fabricated from the resulting polymer.

In an alternate embodiment, the hydrogel is pre-applied to a surface and contains chemical moieties that interact with nucleic acids. In the preferred embodiment, amine groups on 2-amino ethyl methacrylate (AEMA) interact with chromosomal DNA, in contrast to prior use for selective release of nucleic acid based drug compounds [Alsberg 2013], reviewed in [Du 2010]. This hydrogel does not need to be applied over the analyte and can be pre-polymerized before addition of the analyte, but does not enable 3-D sectioning of the hydrogel.

In another embodiment, a photodegradable hydrogel is formed by polymerizing glycol chitosan with a PEG monomer derivatized at both ends with oNB to form PEG-4-(3-(1-(N-hydroxysuccinimidyl carbonicester)ethyl)-4-nitrophenoxy)butanoate. [Wu 2019]

In an alternate embodiment, photochemistry is employed both in the construction and destruction of the hydrogel, preferably by using photochemical groups with differing wavelength sensitives. Irradiation with the construction wavelength is used to selectively deposit hydrogel, while irradiation with the photodegradation wavelength is used to selectively remove hydrogel. In alternate embodiments the hydrogel is comprised of azobenzene groups which reversibly deform in response to different wavelengths of light. In one embodiment the hydrogel is comprised of N,N-dimethylaminoethyl methacrylate (DMAEMA) and 4-methyl-[7-(methacryloyl)oxy-ethyl-oxy]coumarin (CMA), is polymerized with 405 nm light and photodegraded with 254 nm light [He 2011].

In an alternate embodiment, after a sample of nucleic acids containing at least one labeling body has been interrogated by an interrogation device and a portion has been selected for further analysis, the selected molecule or portion of the molecule, or multiple portions of one or more molecules can be selectively manipulated by applying a hydrogel precursor to the entire sample and photopolymerizing it only in locations where the sample of interest is not. In the most preferred embodiment, the hydrogel precursor is PEG DA, which is cured in the presence of Irgacure 2959 by irradiation with light between 320 and 390 nm.

Closed and Open Devices and Impacts on Elution and Collection

The photodegradable hydrogel can be placed in either open or closed fluidic device. An example of an open system is a microscope coverglass that is exposed to a microscope objective and if applicable optical coupling fluid on the underside, has the sample deposited on the top side and is then exposed to air. Air can comprise environmentally conditioned air of controlled temperature, humidity, pressure or partial pressures of constituent molecules. Other features of the device can exist proud of the top surface of the device, for example. the coverglass and sample can be the bottom of a well.

The photodegradable hydrogel can alternately be placed inside an enclosed microfluidic device as defined earlier. In this case the depth and planar extent of the hydrogel can be limited by the depth of the flowlane, shape of the flowlane, surface chemistry or surface patterning, or flow of one or more alternate streams of fluid.

There are advantages and disadvantages to each approach. In the case of closed devices where the entirety of the flowchannel is filled with a hydrogel, any attempt to washout depolymerized hydrogel or elute sample will first require that the hydrogel in proximity to the entrance and exit ports is cleared away to a substantial degree so that a continuous fludic path is available to route fluid from entrance to exit. Some embodiments first polymerize a thin layer of hydrogel then place a ceiling over the hydrogel to form a flowlane with enough clearance between the ceiling and the hydrogel that fluid can move between an entrance and exit port without any need to cut channels. Preferred embodiments instead limit the extent of the hydrogel polymerization by means of selective delivery of the hydrogel precursor to a specific portion of the device prior to polymerization. Once a fluidic pathway is capable of moving regents to and from the hydrogel area, closed microfluidic systems are able to achieve very quick and thorough washing of the hydrogel areas with minimal fluidic volume, which translates to minimal expense of reagent such as proteases, endonucleases or polymerases. Open systems can still achieve the same degree of washing but may require a greater amount of reagent to be delivered.

Extraction of sample from open devices can proceed by deposition of fluid on top of the hydrogel, optionally mixing the fluid, then aspiration of the fluid. Preferred embodiments utilize a robotic pipetting arm and replaceable pipette tips, and deposit samples in a 384 well plate.

Extraction of sample from closed devices can proceed by flowing sample through a flowlane to another portion of the fluidic device, or out of the fluidic device and through a capillary to another fluidic device, or out of the fluidic device for deposition in a collection system, most preferably an automated fraction collector stationed over a 384 well plate. Alternately, the sample can be placed in a fluidic droplet in an emulsion, with or without prior mixing with barcoding reagents.

FRET Proximity Labelling Body Pairs

In another set of embodiments, at least two fluorescent labelling bodies are separately bound to different regions of a higher order nucleic acid structure, such that within the collection of at least two labelling bodies, there is exists a pair of labelling bodies that can form a FRET pair when in sufficient proximity to each other. Unlike methods of interrogating proximity relationships between segments of long nucleic acid molecules that rely on cross-linking, and thus limit proximity information to a single point in time, the disclosed method can dynamically form FRET pairs as the sample evolves, allowing for the monitoring of real-time proximity relationship dynamics over a duration of time. By interrogating the FRET signal generated by a FRET pair when being fluorescently interrogated by an interrogation system, in which the pair are each bound to two different locations within the structure, the number of times, and the duration of each time the two locations are in sufficient proximity to each other to generate a FRET signal can be monitored. In addition, the magnitude, angle, and polarization of the FRET signal can be used to infer information about the distance and orientation of the FRET pair from each other.

In some embodiments, the nature of a FRET signal is interrogated over at least a portion of a cell cycle, for example when the cell is in interphase, or prophase, or prometaphase, or metaphase, or anaphase, or telophase. In some embodiments, the nature of a FRET signal is interrogated over at least a portion of a cell's life, for example during apoptosis. In some embodiments, the nature of a FRET signal is interrogated over at least a portion of a change in a cell's morphology, for example blebbing, plasmolysis, karyorrhexis, pyknosis, or DNA fragmentation. In some embodiments, the nature of a FRET signal is interrogated over at least a portion of a physical change in a nucleic acid structure in a cell, including a change in physical composition, morphology, density, conformation, or topology. In some embodiments, the nature of a FRET signal is interrogated over at least a portion of a cell's checkpoint. In some embodiments, the nature of a FRET signal is interrogated over at least a portion of a period in which a cell undergoes a certain enzymatic activity, for example transcription, loop extrusion, gene regulation, formation or deconstruction of a transcription complex, In some embodiments, the nature of a FRET signal is interrogated over at least a portion of a period when a package or long nucleic acid molecule is exposed to a certain reagent, or combination of reagents, or concentration of reagent. In some embodiments, the nature of a FRET signal is interrogated over at least a portion of a period when a package or long nucleic acid molecule is exposed to an environmental condition. In some embodiments, the nature of a FRET signal is interrogated over at least a portion of a period when a package or long nucleic acid molecule is exposed to a certain protein, or enzyme.

In some embodiments, a higher order nucleic acid structure may have one acceptor and more than one possible donors bound. In some embodiments, a higher order nucleic acid structure may have one donor and more than one possible acceptors bound. In some embodiments, a higher order nucleic acid structure may have more than one possible donor, and more than one possible acceptor bound.

Figure 10:
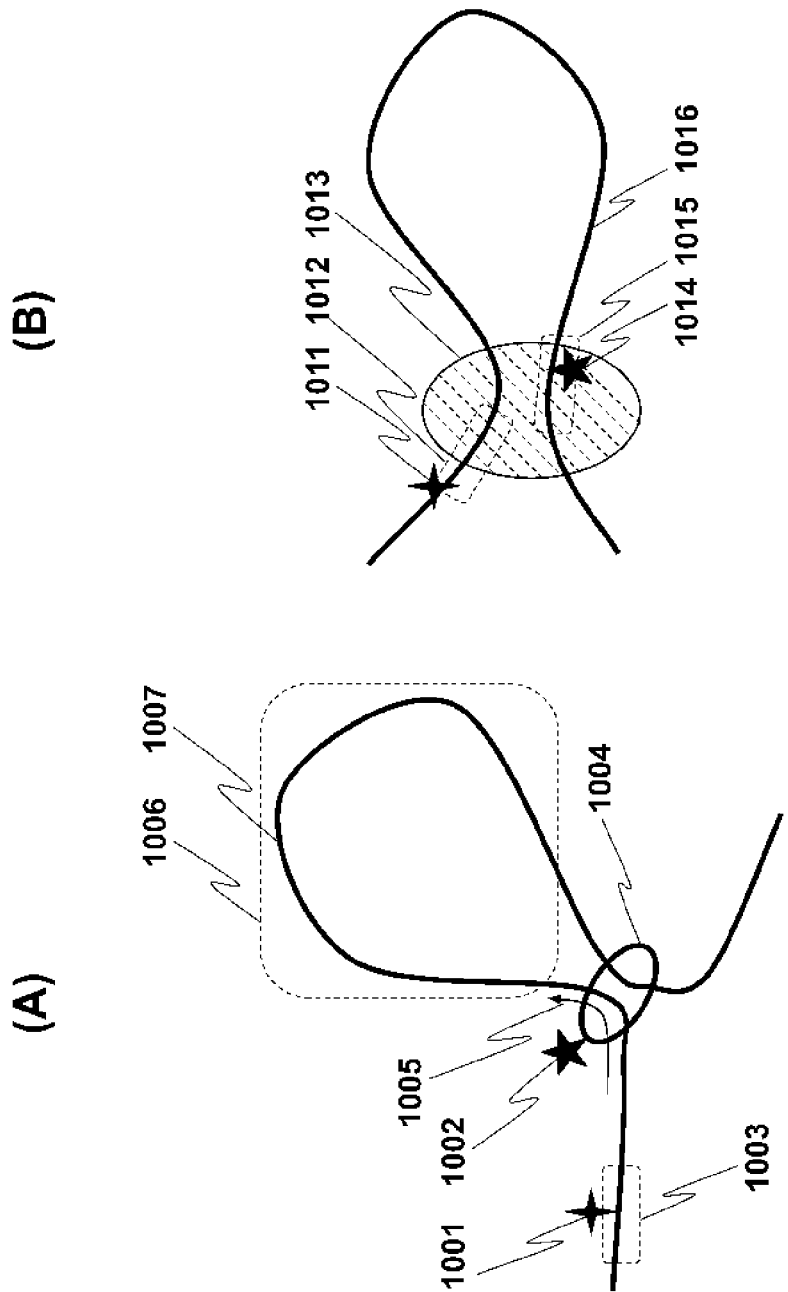
FIG. 10(A) demonstrates a long nucleic acid molecule with a condensin complex labelled with a FRET pair such that the proximity dynamics of the FRET pair can be interrogated.
FIG. 10(B) demonstrates a long nucleic acid molecule with a transcription complex labelled with a FRET pair such that the proximity dynamics of the FRET pair can be interrogated.

FIG. 10(A) demonstrates an embodiment where-by a long nucleic acid molecule (1007) with a higher order nucleic acid structure consisting of a loop (1006) and cohesin complex (1004) are labeled with two labelling bodies that together can form a FRET pair when in sufficient proximity to each other. In this particular embodiment, a donor labelling body (1001) is bound at, or in near to, a CTCF site (1003), while the acceptor labelling body (1002) is bound to the cohesin complex. With such an embodiment, a FRET signal can be detected during interrogation of the FRET pair as the pair come into proximity during the process of loop extrusion (1006).

FIG. 10(B) demonstrates an embodiment where-by a long nucleic acid molecule (1016) with a higher order nucleic acid structure consisting of a loop and transcription complex (1013) are labeled with two labelling bodies that together can form a FRET pair when in sufficient proximity to each other. In this particular embodiment, a donor labelling body (1011) is bound at, or in near to, a promoter site, while the acceptor labelling body (1014) is bound at, or near to, the enhancer site. With such an embodiment, a FRET signal can be detected during interrogation of the FRET pair as the pair come into proximity during the process of transcription.

In some embodiments, statistics on the nature of the FRET signal of at least one individual FRET acceptor labelling body are recorded by an optical interrogation system. In some embodiments, more than 2 individual acceptors, or more than 10 individual acceptors, or more than 100 individual acceptors.

In some embodiment, statistics of the nature of a FRET signal generated by a population of acceptors are collected from a population of more than 10 acceptors, or more than 100 acceptors, or more than 1,000 acceptors, or more than 10,000 acceptors.

In some embodiments, the FRET pair labelling bodies are bound to the higher order nucleic acid structure when said structure is contained within or on a fluidic device. In some embodiments, the FRET pairs bound to the higher order nucleic acid structure are fluorescently interrogated while said structure is contained within a fluidic device.

Cleavable Proximity Barcoded Crosslinker (CPBC)

In this set of embodiments methods we describe a body here defined as a "Cleavable Proximity Barcode Crosslinker" (CPBC). A CPBC is an entity that comprises at least two capture probes, of which, at least one capture probe is a releasable capture probe that can be physically separated from the CPBC via cleaving one or more cleavable linkers that connects said at least one resealable capture probe to the CPBC. By crosslinking the CPBC with one or more bio-molecules via the binding of the capture domains with their respective target bio-molecule(s), the proximity relationship of those bio-molecule(s) can be maintained and tracked via the barcodes after the releasable capture probes have been released from the CPBC.

In the preferred embodiment, the capture probes, which the CPBC is comprised of, each have a barcode that collectively form a "relationship set", such that knowledge of the identify of one barcode within the relationship set, allows for the determination of the identity of the other barcodes within the same relationship set. In some embodiments, all of the barcodes that form a relationship set are identical. In some embodiments, at least two barcodes within the relationship set include complementary sequences of each other. In some embodiments, at least one barcode in the relationship set can be determined from another barcode in the same relationship set via a mathematical function, or look-up table. In the preferred embodiment, each CPBC has a unique relationship set of barcodes, such that if given a collection of barcodes that originate from multiple CPBC's, the collection of barcodes can be sorted into the originating relationship sets. For example, if given a collection of barcodes that originate from CPBC-1, CPBC-2, and CPBC-3, the collection can be sorted into three distinct relationship sets: a relationship set of barcodes that originate from CPBC-1, a relationship set of barcodes that originate from CPBC-2, and a relationship set of barcodes that originate from CPBC-3.

CPBCs offer highly advantageous method of identifying and tracking the proximity relationships of various bio-molecules or portions of bio-molecules within a liquid environment over a duration of time, or at a specific time point, as both the proximity and temporal relationship of the bio-molecules, or portions of bio-molecules can be determined from the bound capture probes. In some embodiments, a CPBC can be introduced to an environment that contains at least some target bio-molecules at desired time point. In some embodiments, a CPBC is introduced to target bio-molecule inside of, or on, a fluidic device. In some embodiments, at least one capture domain of at least one capture probe can be activated or deactivated at a desired time to cross-link with its target bio-molecule. In some embodiments, the activation or deactivation mechanism is a certain wavelength of light, or a temperature, or a pH.

In some embodiments, multiple CPBCs may be introduced to an environment containing target molecules at different time points. In the preferred embodiment, at least a portion of the information contained within the barcodes can be associated with the time of introduction or the order of introduction.

A CPBC may be designed such the physical volume that which capture probes occupy can be selected for a particular application. In such a manner, a CPBC may be designed to investigate proximity relationships between bio-molecules, or portions of bio-molecules that span a large range of physical distances. In some embodiments, it may be desired to select a particular sized CPBC to track the proximity relationships of different sized higher order nucleic acid structures.

A CPBC in particular is advantageous for applications where-by it is desired to maintain the long-range order or integrity of the bio-molecule (or bio-molecules) being tracked. Unlike existing commonly used proximity detection methods (see definitions for "Proximity 3D mapping") that require digestion of nucleic acid molecule after capture in order to maintain the proximity relationship of the neighboring molecules, or portions of molecules, a CPBC maintains knowledge of the proximity relationship via barcodes, which can be released from the CPBC via the cleavable linker. In this way, not only can the proximity relationship be maintained via the barcodes, but the long-range sequence content of the nucleic acid molecule can also be maintained. This is particularly important when the sample being interrogated is a single cell, and maintaining long-range integrity of the long nucleic acid molecules is critical for identifying structural variations. Furthermore, by cleaving the cleavable linkers, the molecule(s) can be allowed to re-position into a different physical configuration, allowing for an additional round of binding the by capture probes, either from a new CPBC, or from remaining capture probes from the original CPBC.

In some embodiments, the identify of a barcode is identified via directly sequencing the barcode, or indirectly sequencing an amplification product of the barcode. In some embodiments, the identify of a barcode is identified via binding a labelling body that is designed to specifically bind to a specific barcode, set of barcodes, or sub-set of barcodes.

In the preferred embodiment, at least one CPBC is introduced into an environment where-by conditions are preferable for the capture domain associated with each capture probe to bind to its target bio-molecule. After at least one releasable capture probe is bound to its target bio-molecule via the probe's capture domain, the at least one releasable capture probe is then released from the remaining CPBC via cleaving of the cleavable linker(s).

Figure 11:
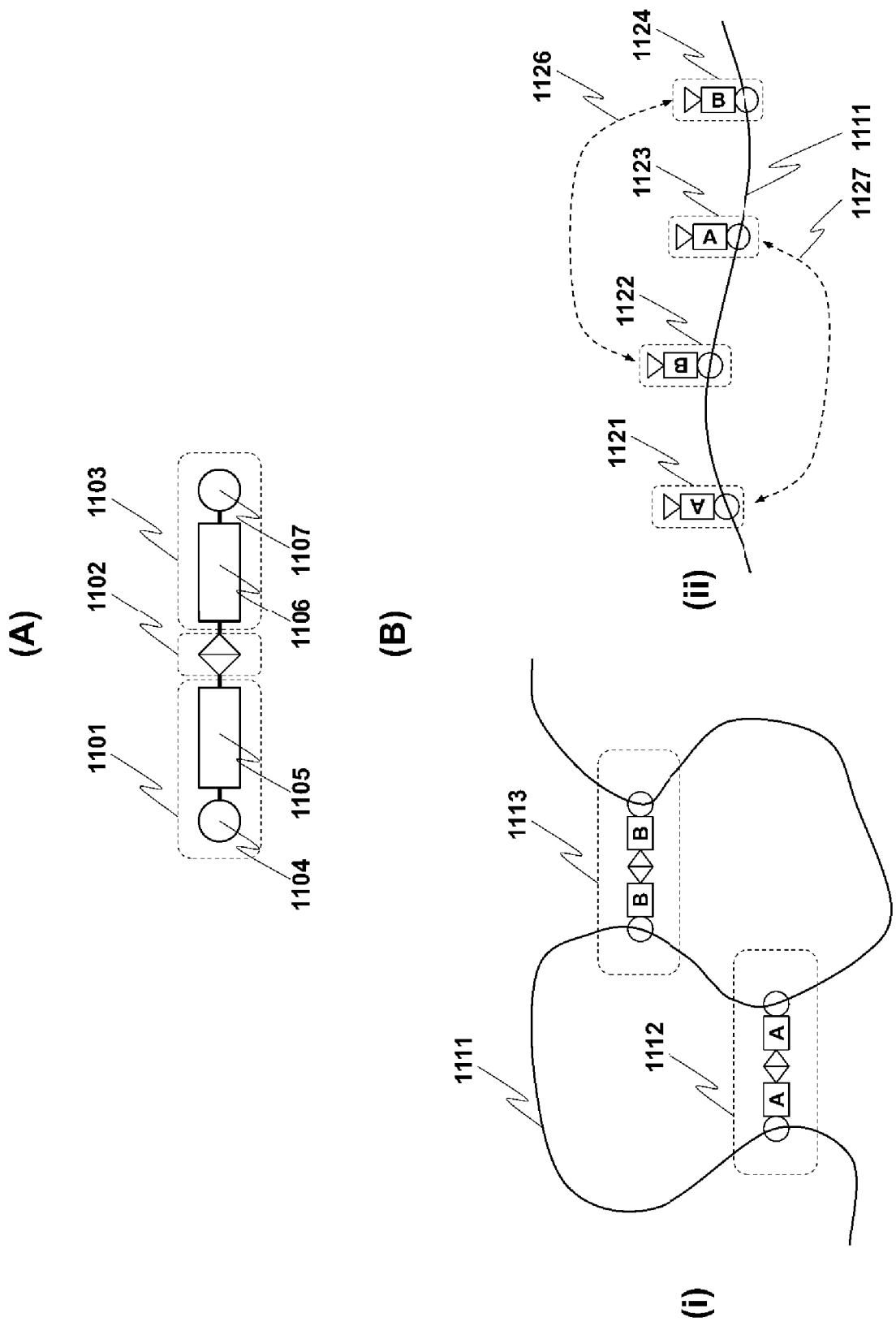
FIG. 11(A) demonstrates an example of a cleavable proximity barcode crosslinker (CPBC) comprising two capture probes linked by a cleavable linker.
FIG. 11(B) demonstrates an example use of the CPBC shown in FIG. 11(A). Here (i) two such CPBCs with different barcodes are cross-linked to a long nucleic acid molecule, and then (ii) the CPBCs are cleaved, removing the crosslinking, and resulting in the long nucleic acid molecule with bound capture probes, wherein the barcodes retain knowledge of the previous proximity relationships.

FIG. 11(A) identifies one possible embodiment of the CPBC. Here, the CPBC is comprised of two capture probes (1101 and 1103) that are joined by a cleavable linker (1102). In this particular embodiment, the first capture probe (1101) is comprised of a capture domain (1104) and a barcode (1105). In addition, the second capture probe (1103) is comprised of a barcode (1106) and a capture domain (1107). Here, the barcodes (1105 and 1106) belong to a relationship set.

FIG. 11(B) demonstrates one possible embodiment use of the CPBC described in FIG. 11(A) to capture proximity knowledge of portions of a long nucleic acid molecule. Here, there are two distinct CPBCs (1112 and 1113) are crosslinked to the same long nucleic acid molecule (1111), each CPBC with a unique relationship set of barcodes, the first CPBC (1112) with relationship set A, and the second CPBC (1113) with relationship set B. Here in this example, all capture domains associated with both CPBCs are designed to non-specifically bind to nucleic acid or chromatin, such that at time point (i) a long nucleic acid molecule (1111) is cross-linked by both CPBCs (1112 and 1113) at regions where two portions of the long nucleic acid molecule (1111) are sufficiently close in proximity to each other that they can be bridged by the CPBC cross-linking. At a later point in time (ii), the cleavable linkers within CPBCs are cleaved, releasing the capture probes that originate from the same CPBC from each other. Along the length of the long nucleic acid molecule (1111) there are now 4 bound capture probes (1121, 1122, 1123, 1124), in which knowledge of the previous proximity relationship of the portions of the molecule is maintained by the barcodes contained in the capture probes. Thus knowledge of the previous proximity relationship 1126 from the second CPBC is maintained by barcode relationship set B, and knowledge of the previous proximity relationship 1127 from the first CPBC is maintained by the barcode relationship set A.

Figure 12:
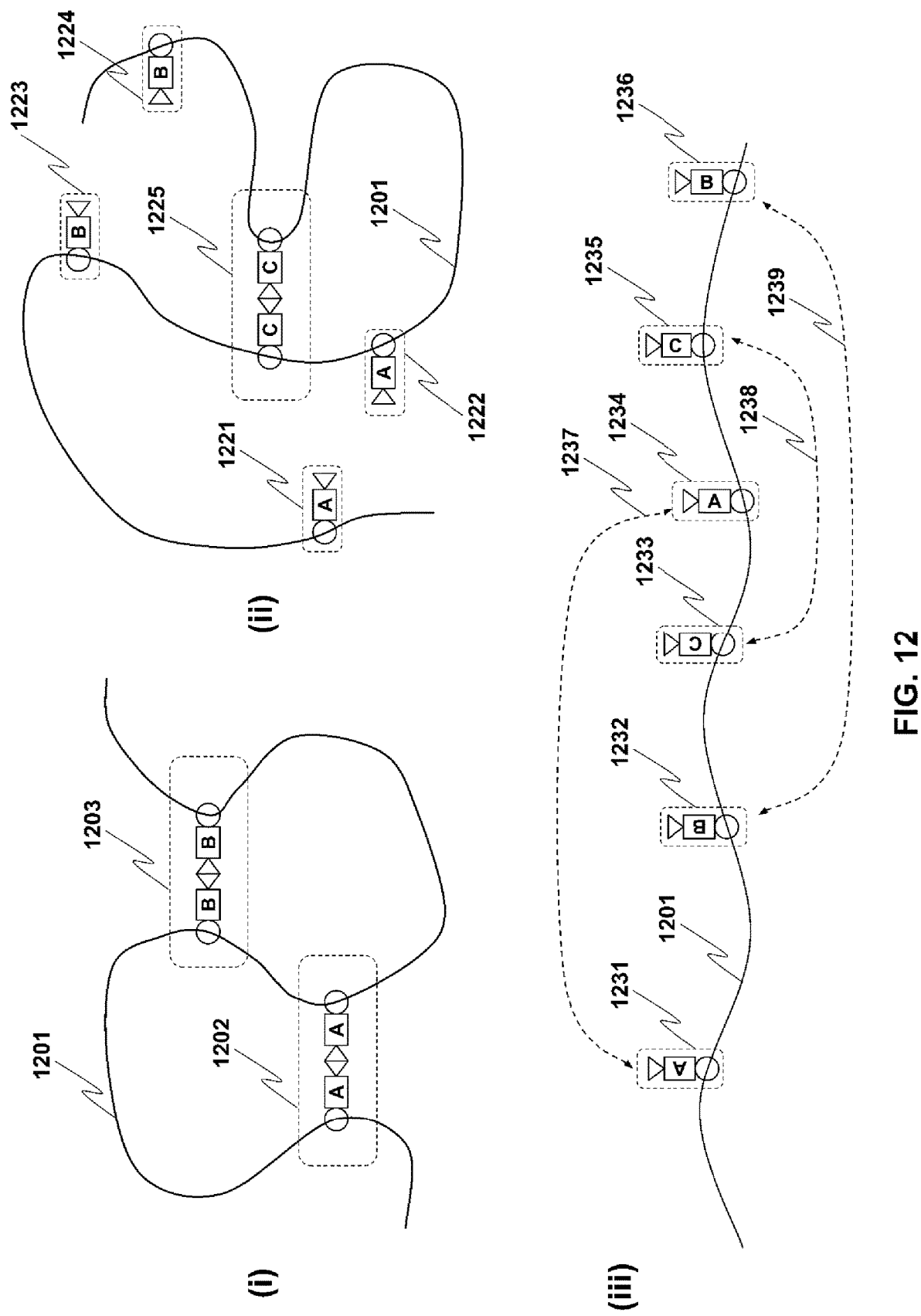
FIG. 12 demonstrates an example use of the CPBC shown in FIG. 11(A). Here (i) two such CPBCs with different barcodes are crosses-linked to a long nucleic acid molecule, and then later cleaved, removing the cross-linking. Next at a later time-point (ii), a third CPBC with a different barcode is cross-linked to the long nucleic acid molecule, and then later cleaved. This result is (iii) a long nucleic acid molecule with bound capture probes, wherein the barcodes retain knowledge of the previous proximity relationships at various time-points.

FIG. 12 demonstrates another possible embodiment use of the CPBC described in FIG. 11(A) to capture proximity knowledge of portions of a long nucleic acid molecule at two different time points. First (i) the proximity relationship of portions of the long nucleic acid molecule 1201 is captured by cross-linking the molecule at two locations of close proximity with two separate CPBCs, a first CPBC (1203) and a second CPBC (1202), each respectively with a unique barcode relationship set: B and A. As in the previous embodiment, here the CPBCs comprise capture domains that non-specifically bind to nucleic acid or chromatin. The two CPBC respective cleavable domains are then cleaved, thus removing the cross-linking, and allowing for the long nucleic acid molecule (1201) to reconfigure physically such that at a later time point (ii) an additional third CPBC is introduced (1225), with a barcode relationship set C., This third CPBC cross-links to the same long nucleic acid molecule (1201), while the previous proximity relationships are maintained by the bound capture probes (1221 and 1222 from the second CPBC (1202), and 1223 and 1224 from the first CPBC (1203)). Later, (iii) after the cleavable linker from third CPBC (1225) is cleaved, the long nucleic acid molecule (1201) has bound to it 6 capture probes that maintain the previous proximity and temporal relationships of segments of said molecule. Here, the proximity relationship 1237 from the second CPBC is maintained by bound capture probes of relationship set A (1231 and 1234), and the proximity relationship 1239 from the first CPBC is maintained by bound capture probes of relationship set B (1232 and 1236), while the later in time proximity relationship 1238 from the third CPBC is maintained by bound capture probes of relationship set C (1233 and 1235).

Figure 13:
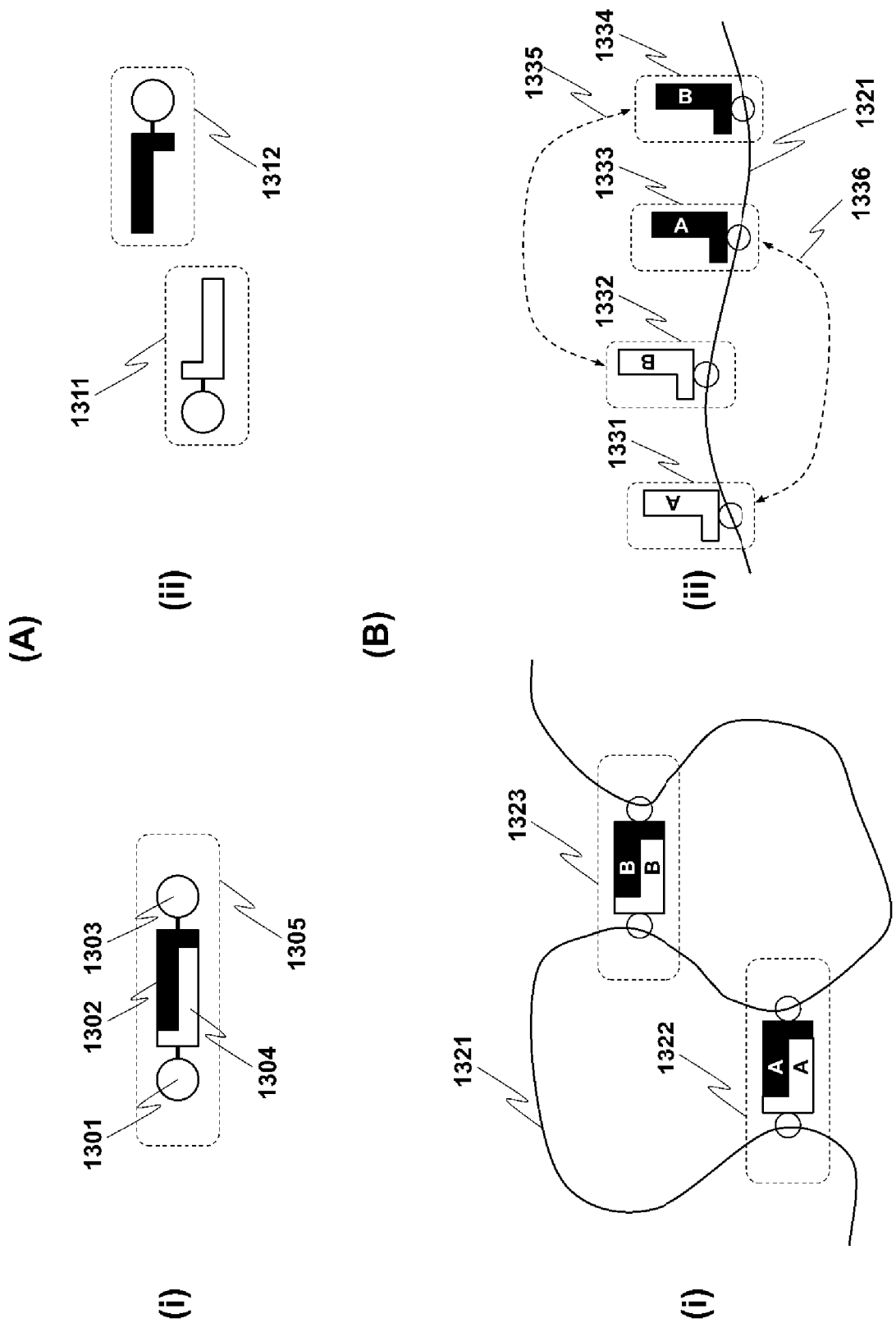
FIG. 13(A) demonstrates an example CPBC where the CPBC's cleavable linker comprises a double strand nucleic acid that can be melted under appropriate environmental conditions. Here, (i) the CPBC prior to melting, and (ii) post-melting, resulting in two isolated capture probes.
FIG. 13(B) demonstrates an example use of the CPBC shown in FIG. 13(A). Here (i) two such CPBCs with different barcodes are cross-linked to a long nucleic acid molecule, and then (ii) the CPBCs are cleaved (melted), removing the crosslinking, and resulting in the long nucleic acid molecule with bound capture probes, wherein the barcodes retain knowledge of the previous proximity relationships.

FIG. 13(A) describes another embodiment of a CPBC (1305). In this embodiment, the cleavable linker consists of two nucleic acid molecules (1304 and 1302) that are hybridized together, in which the cleaving mechanism to separate the two capture probes can comprise a variety of methods, as described previously in the definition of "cleavable linker", specifically when the cleavable linker comprises a nucleic acid. In this particular embodiment, the two nucleic acid molecules (1304 and 1302) are hybridized together, but do not share a phospho-diester backbone, and cleaving is achieved via melting of the hybridization bond between them. In the preferred embodiment, the two strands are not 100% complementary, and have a >50% AT base-pair content, such that their effective melting temperature is lower than the average melting temperature of any target long nucleic acid molecule that their respective capture probes may cross-link with. In some embodiments, the capture probe's barcode comprises at least a portion of the nucleic acid to be melted. In some embodiments, the capture probe's barcode does not comprise any portion of the nucleic acid to be melted. In this particular embodiment, after melting (cleaving) the cleavable linker, (ii) two capture probes are released from each other (1311 and 1312), where-by the first capture probe 1311 comprises a capture domain (1301) and barcode (1304), and the second capture probe 1312 comprises a capture domain (1303) and barcode (1302).

FIG. 13(B) demonstrates one possible embodiment use of the CPBC described in FIG. 13(A) to capture proximity knowledge of portions of a long nucleic acid molecule. Here, there are two distinct CPBCs, a first CPBC (1322) and a second CPBC (1323), each with a unique relationship set of barcodes, the first CPBC (1322) with relationship set A, and the second CPBC (1323) with relationship set B. Here in this example, all capture domains associated with both CPBCs are designed to non-specifically bind to nucleic acid or chromatin, such that at time point (i) a long nucleic acid molecule (1321) is cross-linked by both CPBCs (1322 and 1323) at regions where two segments of the long nucleic acid molecule (1321) are in sufficiently close proximity to each other, that they can be cross-linked by a CPBC. At a later point in time (ii), the cleavable linkers within CPBCs are cleaved (melted), releasing the capture probes that originate from the same CPBC, from each other. Along the length of the long nucleic acid molecule (1321) there are now 4 bound capture probes (1331, 1332, 1333, 1334), in which knowledge of the previous proximity relationship of the portions of the molecule is maintained by the barcodes contained in the capture probes. Thus knowledge of the previous proximity relationship 1335 from the second CPBC is maintained by barcode relationship set B, and knowledge of the previous proximity relationship 1336 from the first CPBC is maintained by the barcode relationship set A.

In another set of embodiments of this method, the CPBC can be comprised of nucleic acid dendrimer structures, DNA nanotechnology structures, or origami structures. In some embodiments, such structures may comprise loops, junctions, or knots. With such embodiments, the CPBC can comprise more than two capture probes. In some embodiments, the CPBC may comprise 3, or 4, or 5, or 6, or 7, or 8, or 9, or 10, or 11, or 12 capture probes. In some embodiments, the CPBC may comprise more than 2 capture probes, more than 3 capture probes, more than 5 capture probes, more than 10 capture probes, more than 15 capture probes, more than 20 capture probes, more than 50 capture probes, more than 100 capture probes, more than 500 capture probes.

Figure 14:
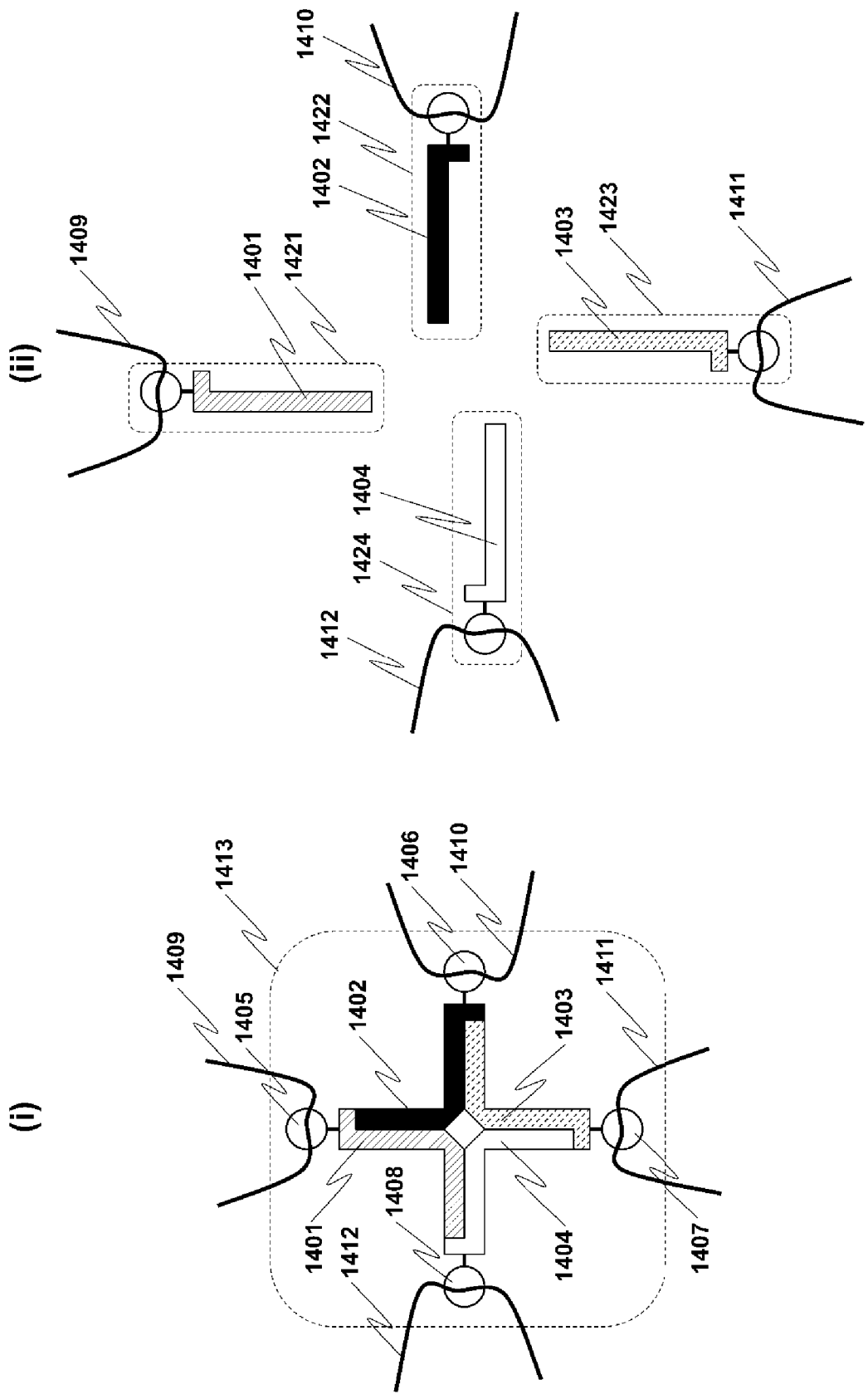
FIG. 14 demonstrates an example CPBC where the CPBC comprises a DNA origami structure, similar to that of a Holliday Junction, such that CPBC comprises 4 capture probes. (i) After cross-linking to the target molecule(s), (ii) the CPBC's cleavable linkers are then melted, releasing the 4 capture probes from each other.

FIG. 14 demonstrates an embodiment where-by a CPBC is comprised of 4 capture probes, each of which are associated with a respective nucleic acid molecule and capture domain, wherein the 4 nucleic acid molecules form a type of Holliday Junction. In this particular embodiment, the CPBC first (i) cross-links 4 segments of long nucleic acid molecules (1409, 1410, 1407, 1412), which may originate from one, or multiple long nucleic acid molecules. In this particular embodiment, the capture probes are comprised of a capture domain and a nucleic acid molecule that comprises both the barcode and a portion of the cleavable linker. The first capture probe 1421 is comprised of capture domain 1405 and nucleic acid polymer 1401. The second capture probe 1422 is comprised of capture domain 1406 and nucleic acid polymer 1402. The third capture probe 1423 is comprised of capture domain 1407 and nucleic acid polymer 1403. The fourth capture probe 1424 is comprised of capture domain 1408 and nucleic acid polymer 1404. Similar to the previous example of FIG. 13(A), the capture probes are hybridized to each other to form cleavable linkers at the region of hybridization, without sharing a phospho-diester backbone. Here, the first capture probe (1421) has one portion of its nucleic acid polymer hybridized to a portion of the fourth capture probe, and a second portion of its nucleic acid polymer hybridized to a portion of the second capture probe. In this particular embodiment, an example of a releasable capture probe (1421) that is connected to a CPBC via two cleavable linkers is demonstrated. This sequence is repeated for the other capture probes as shown in FIG. 14, time point (ii), such that all capture probes are then released.

In this particular embodiment of FIG. 14, the CPBC comprising the four capture probes is capable of cross-linking the target molecule (or molecules) that fall within the volume, or proximity capture region, occupied by the CPBC (1413). Thus, the desired proximity distance to be captured can be modified by selecting a DNA origami structure with different branch lengths, numbers of branches, and physical configurations.

For some embodiments, the CPBC is at least partially assembled by self-assembling of molecules that comprise at least one single-strand of nucleic acid polymer, via hybridization of at least a portion of said at least one single-strand nucleic acid polymer to another nucleic acid polymer. For some embodiments, the additional nucleic acid molecule polymer material may be included as filler to modify the length or flexibility of the contract probes or branches, such that proximity capture region of the CPBC (1413) can be modified and tuned as desired. In some embodiments, the filler does not comprise any part of the capture probe's barcode or cleavable linker.

In another set of embodiments of this method, the CPBC can be comprised of a central 'bead', which may be functionalized such that at least two capture probes may be connected to the bead, of which at least one capture probe is a releasable capture probe connected to the bead through a cleavable linker. In some embodiments the bead may be a dendrimer, or a polystyrene bead, or a nanoparticle, or a nanodot, or a quantum dot. In some embodiments the bead comprises a fluorescent property. For example, the bead may comprise a fluorescent bead. In some embodiments, the bead comprises a photoluminescence property. For example, the bead may comprise a solid-state quantum dot capable of emission of a certain wavelength of light when stimulated with UV light. In some embodiments, the bead comprises a magnetic property. For example, the bead may comprise a magnetic bead.

Figure 15:
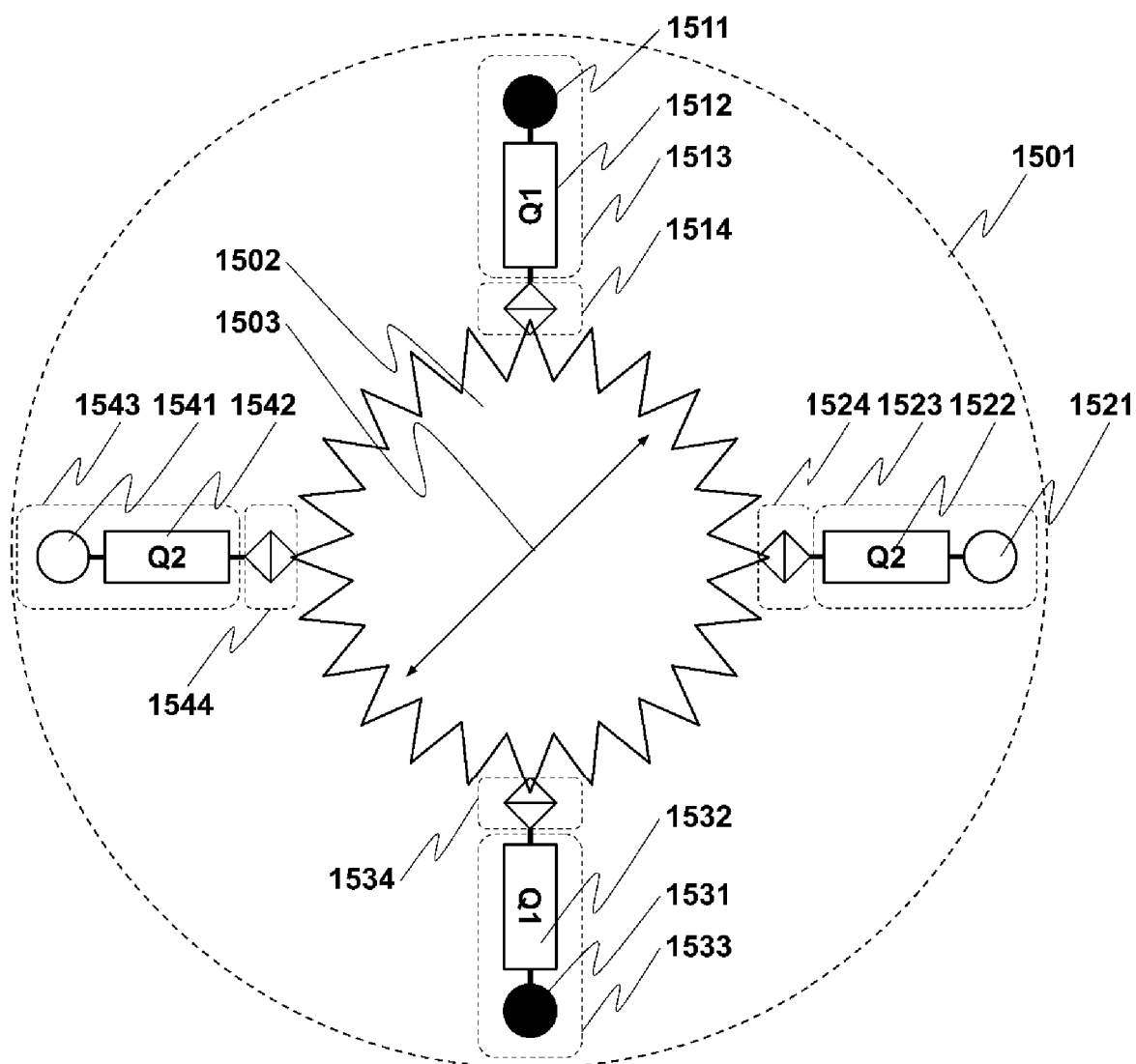
FIG. 15 demonstrates an example of a CPBC comprising a ball that is a functionalized dendrimer, to which 4 capture probes are attached via a cleavable linker.

FIG. 15 describes one embodiment CPBC which comprises a bead (1502) of diameter 1503, onto which there are 4 capture probes (1513, 1523, 1533, 1543) which are bound to the bead via their respective cleavable linkers (1514, 1524, 1534, 1544). In this particular embodiment, there are two sub-sets of relationship sets: Q1 and Q2. Capture probes 1513 and 1533 share barcodes from the same sub-set Q1, while capture probes 1523 and 1543 share barcodes from the same sub-set Q2. In this particular example, all barcodes belonging to sub-sets Q1 and Q2 belong to the same parent relationship-set Q, which associates all barcodes within the set with the CPBC shown in FIG. 15. However, the sub-sets Q1 and Q2 are also associated with a type of capture domain, here sub-set Q1 with a capture domain (1511 and 1531) that targets a first target type of bio-molecule, and sub-set Q2 with a capture domain (1521 and 1541) that targets a second target type of bio-molecule. This is advantageous, as it allows for tracking of particular bio-molecule types (or portions of bio-molecules) that fall within the proximity capture region (1501) such that they can be cross-linked by the CPBC.

A variety of different relationship sub-sets may be used within a CPBC. In some embodiments, the sub-set may be associated with physical location within the bead. For example, the north or south hemisphere, or distance from the core of the bead. For beads that are permeable, such as non-dense dendrimers, there may be several layers of shells, each with a different diameter and unique relationship sub-set. The sub-set may be associated with the target type of the capture domain. The sub-set may be associated with the physical length, conformation, or rigidity of the capture probe. The sub-set may be associated with a particular type of activation that can activate the capture domain such that it can cross-link with its target bio-molecule. For example, a certain wavelength of light, heat, pH or catalyst. The sub-set may be associated with a particular type of cage that blocks the capture domain (eg: with a photoliable protecting group) until said capture domain is unblocked. For example: at time point 1, the un-caged capture probes of a CPBC of sub-set Q1 cross-link all target molecules within proximity. Then, at a later time point 2, the caged captured probes of said CPBC of sub-set Q2 are then un-caged via exposure to a wavelength of light, and are then free to cross-link all target molecules within proximity.

In some embodiments, all capture domains target the same target type. In some embodiments, each capture domain targets a different target type. In some embodiments, there are at least two capture domains that capture the same target type. In some embodiments, a CPBC may crosslink only one type of target type, or at least one target type, or at least two different target types, or at least three different target types, or at least five different target types.

In some embodiments, a target type may be a nucleic acid, a long nucleic acid, a chromatin, a AT-rich region of long nucleic acid molecule, a CG-rich region of a long nucleic acid, a particular gene, a particular enhancer, a particular promoter, a regulator region, a non-functional region, a region of telomere, a region of centromere, a particular sequence, a protein, a particular protein, an enzyme, a particular enzyme, a DNA binding protein, a particular DNA binding protein, an organic molecule, an ATP, a particular higher order nucleic acid structure.

Figure 16:
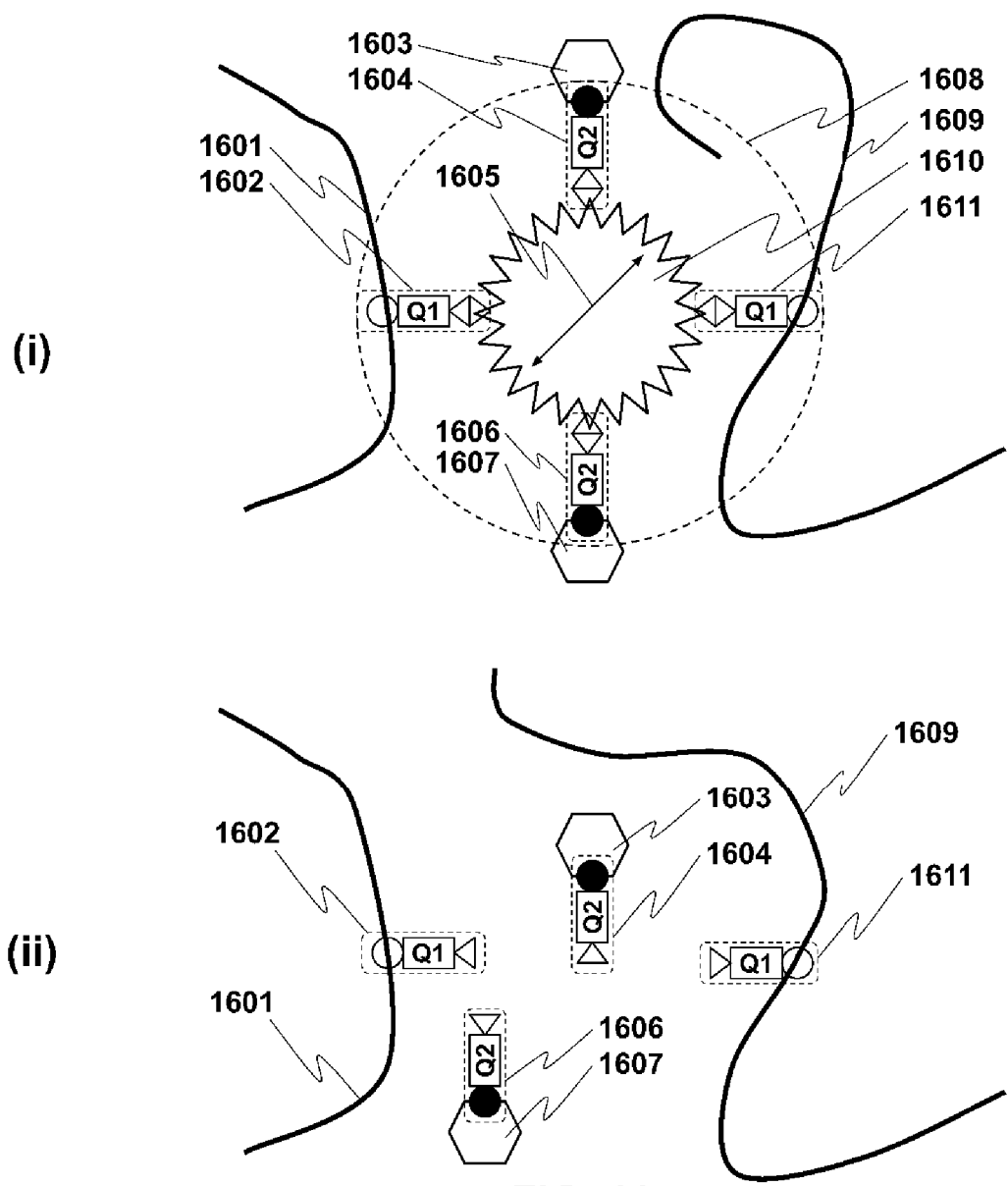
FIG. 16 demonstrates an example use of the CPBC shown in FIG. 15. Here (i) the CPBC is cross-linked to long nucleic acid molecules and proteins. After cross-linking (ii), the capture probes are released from the CPBC, resulting in proteins and nucleic acid bound to capture probes that retain knowledge of the previous proximity relationship of the bio-molecules.

FIG. 16 demonstrates an embodiment of a CPBC that comprises two different relationship sub-sets Q1 and Q2, where-by Q2 is associated with binding to a particular protein, and Q1 is associated with non-specific binding to a nucleic acid polymer. In this particular embodiment, the bead (1610) of a certain diameter (1605) has 4 capture probes, two of which (1604 and 1606) are associated with relationship sub-set Q2, and via their respective capture domains, and are crosslinked to a particular protein target type (1603 and 1607) that came within the proximity region (1608) of the CPBC. The other two capture probes (1611 and 1602) are associated with relationship sub-set Q1, and via their respective capture domains, are crosslinked to long nucleic acid molecules (1609 and 1601) which also came within the proximity region of the CPBC.

At a later time point (ii), the various capture probes associated with the CPBC are then released from the bead via cleaving of the cleavable linker. Post-release, the long nucleic acid molecules (1601 and 1609) remain bound to their respective capture probes (1602 and 1611), and the particular proteins (1603 and 1607) remain bound to their respective capture probes (1604 and 1606).

In some embodiments, the CPBC comprises at least two different capture probes, in which the two capture probes have different type of cleavable linker. In some embodiments, the type of cleavable linker associated with the capture probe can be identified by barcodes belonging to a unique relationship sub-set. This can be highly advantageous when it desired to release a particular sub-population of captured molecules at different time points. For example, barcodes from relationship sub-set Q1 are associated with capture probes that have capture domains that bind to long nucleic acid molecule(s), and are connected to a bead via a cleavable linker of type 1. Similarly, barcodes from relationship sub-set Q2 are associated with capture probes that have capture domains that bind to a protein type, and are connected to said bead via a cleavable linker of type 2. With such an embodiment, many possible work flows are possible. In one example workflow, after crosslinking with the captured molecules (or portions of molecules) that come into proximity with the CPBC, the capture probes cross-linked to the long nucleic acid are first released from the bead via the cleaving mechanism associate with cleavable linker type 1. Then, at a later point in time, and preferably in a different environment, the capture probes cross-linked to the proteins are then released from the bead via the cleaving mechanism associated with cleavable linker type 2. This is highly advantageous, as the down-stream processes required to analyze the capture molecule and identify the barcodes associated with their bound capture probes may be different. In this particular example, the CPBC bead comprising a magnetic property would be highly advantageous, as the bead could easily be extracted from the solution after the type 1 linkers are cleaved.

In some embodiments the physical volume, or average diameter, of the CPBC may be selected to capture target molecules in different sized proximity volumes or proximity regions. In some embodiments, the CPBC may have an average diameter of more than 5 nm, or more than 10 nm, or more than 15 nm, or more than 20 nm, or more than 30 nm, or more than 50 nm, or more than 75 nm, or more than 100 nm, or more than 150 nm, or more than 200 nm, or more than 500 nm, or more than 750 nm, or more than 1000 nm. In particular, the size of the CPBC may be selected to target various particular types of higher order nucleic acid structures. In addition, in some applications, the different sized CPBC may be used simultaneously or in series on a particular sample so as to probe different proximity relationships with different CPBCs.

After the bio-molecule and its bound capture probe(s) are released from the CPBC via cleaving the cleavable linker(s), a variety of potential post-cross-linking analysis can be performed to both identify the barcodes associated with the capture probes, and analyze the bio-molecule itself. For embodiments where-by the bio-molecule is a long nucleic acid molecule, the molecule may be sequenced, or encapsulated in a droplet, or a physical map be generated from said molecule, or both. In some embodiments, a physical map is generated by interrogating fluorescent labelling bodies bound to the molecule while the molecule is at least partially elongated in a microfluidic device. In some embodiments, a physical map is generated by interrogating fluorescent labelling bodies bound to the molecule while the molecule is at least partially immobilized on a surface of the microfluidic device via a combing method. Combing the long nucleic acid molecule is a particularly advantageous method as the bound capture probes are then readily available to various solution and reagent exchanges that allow for reactions with said probes. For example, the nucleic acid polymer that comprises the probe's barcode can be bound with sequence specific fluorescent tags, or amplified in-situ, or sequenced in-situ. In some embodiments, the barcodes may be sequenced by synthesis, sequenced by hybridization, or sequenced by ligation. In particular such interrogation of the probes can be performed after their physical position is registered in reference to the underlying physical map of the long nucleic acid molecule to which they are bound.

Figure 17:
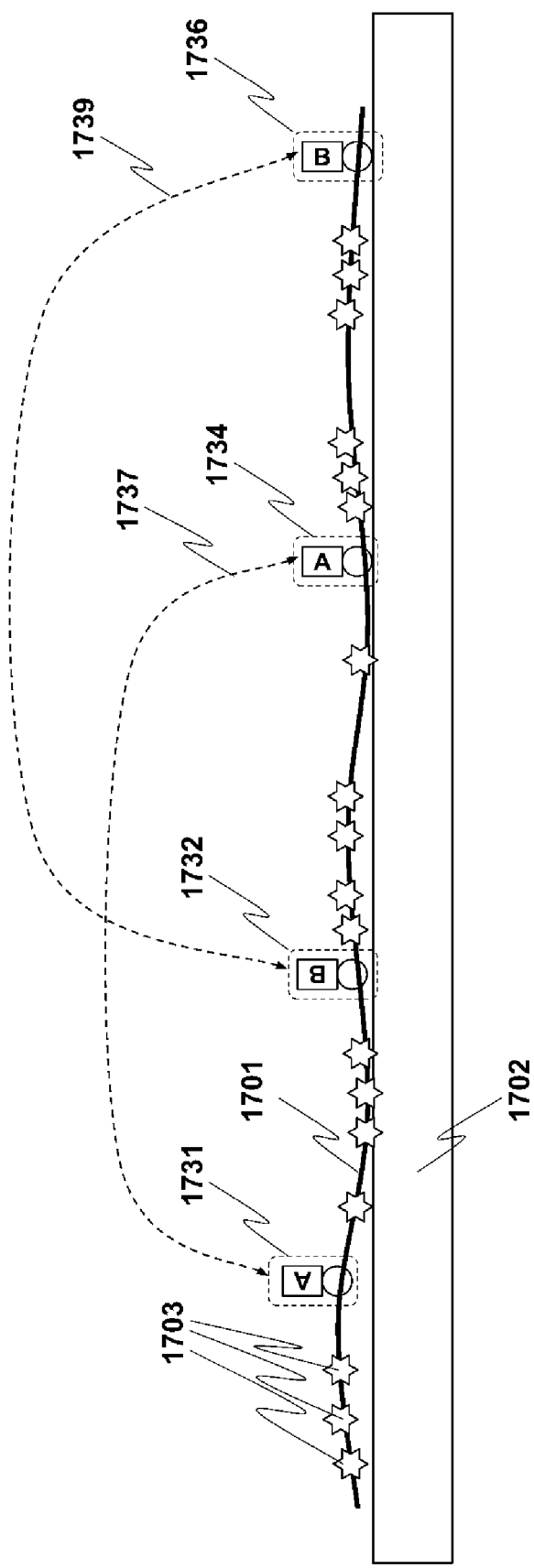
FIG. 17 demonstrates an example of interrogating a long nucleic acid molecule bound with capture probes from CPBCs by combing the molecule on a substrate such that the positional location of the probes with respect to the molecule's physical map can be established via fluorescent interrogation.

FIG. 17 describes an embodiment where-by long nucleic acid molecule (1701) is combed on a substrate surface (1702) and is labeled with fluorescent labelling bodies (1703) along the length of the molecule such that physical map can be generated via fluorescent interrogation with an optical interrogation system. In addition, the molecule is bound with capture probes associated with relationship set A (1731 and 1734) that retain knowledge of a previous proximity relationship (1737) between these two locations along the molecule, and capture probes associated with relationship set B (1732 and 1736) that retain knowledge of a previous proximity relationship (1739) between these two locations along the molecule.

In some embodiment, the substrate surface (1702) on which the long nucleic molecule with bound capture probes is combed on, is a fluidic device.

In some embodiments, it may be advantageous to digest the long nucleic acid molecule bound with capture probes, with at least one type of restriction enzyme. After digesting the long nucleic acid molecule into smaller molecules, there will be a subset of smaller molecules that contain at least a portion of the original long nucleic acid molecule, and a bound capture probe containing a nucleic acid barcode, together which form a pair. After appropriate pre-processing of the pair of nucleic acid polymers such that additional nucleotides can be added to the ends, an additional nucleic acid barcode can be added to their ends, and used to identify them as a "pair". Methods may include SPRIT and ChiA-Drop [Jerkovic, 2021].

In some embodiments, it may be advantageous to introduce at least one CPBC to a sample in which the sample is contained within a fluidic channel or on an exterior surface of a fluidic device. In some embodiments, the sample may be immobilized on the exterior surface, or on a fluidic channel wall. In some embodiments, the sample may be immobilized in a material that has been gelled. In some embodiments, at least one specific region in 2D or 3D space of a sample may be targeted for crosslinking with a CPBC by photo-activating any CPBC occupying said space. In some embodiments, a fluorescent property of the CPBC is used to track said CPBC physical location within the microfluidic device, and within the sample, via fluorescent interrogation.

In some embodiments, each at least one capture probe includes a biotin such that once released from the CPBC, the capture probe can then itself be captured with a streptavidin, or a body that comprises a streptavidin.

In some embodiments, a long nucleic acid molecule bound to at least one releasable capture probe may be enzymatically processed prior to or after said capture probe is released from the CPBC. Enzymatic processing on the long nucleic acid molecule may comprise nicking, digestion, polymerase incorporation of a nucleotide (including modified, labelled, terminated, or reversibly terminated nucleotides), and ligation.

In some embodiments, not all captured bio-molecules capture by a CPBC are captured within a short duration of time. For example, bio-molecules may be captured over a period of several seconds, or minutes, or hours, or days. In some embodiments, the bio-molecules enter the proximity region of the CPBC via diffusion, or fluid flow, or an externally applied force. In some embodiments, the bio-molecules may enter the proximity region of the CPBC at different time-points. In some embodiments, the CPBC captures bio-molecules within a fluidic channel of a microfluidic device.

EXAMPLES

Example 1: Fluidic Device Trapping Swelled Chromosome in Gel

As an initial proof of concept for swelling a chromosome in a fluidic device, and then fixing said chromosome in a gel for further fluorescent interrogation, a model device, an interrogation system, and method of use are described.

A fluidic device comprising of an etched channel in a borofloat glass substrate bonded to a PDMS film is first designed and assembled. A double-side polished borosilicate glass wafers (Pyrex 7740) wafer 0.120 mm thick is uniformly coated with an adhesion layer of chromium (20 nm) and seed layer of copper (200 nm), and then a film of photoresist (AZ9260) is coated on the substrate, exposed through the photomask, and developed according to the manufacturers instructions so as pattern a fluidic device similar to that shown in FIG. 6. In this example device, the primary channel (610) and secondary channel (605) are both 500 microns wide, resulting in a 500 micron by 500 micron intersection region (606). The filtering features (607, 604) comprise of pillars that are 2 microns in diameter, with a 0.5 micron spacing between nearest neighbor pillars. (Note: in this example, there is no filtering features 608 as shown in FIG. 6) Nickel is then electroplated to a thickness of 2 microns on the exposed regions of copper, after which the photoresist is removed by solvent and the Cr/Cu plating layer by reactive ion etching (RIE) to expose the glass substrate. The exposed glass substrate masked by the electroplated nickel is then etched in an inductively coupled plasma etcher using a plasma gas mixture of C4F8 and O2 to a depth of 5 microns to define a fluidic channel.

The glass substrate is then thoroughly washed in a heated mixture of water, ammonia, and hydrogen peroxide to remove any remaining organic material and facilitate particle removal from the surface. Finally, a PDMS film 1 mm thick and the patterned glass are exposed to a surface-activation plasma, and then bonded together at room temperature to encapsulate the channel Inlet and outlet ports are provided by hole punching through the PDMS in alignment with the enclosed channels. Luer lock connections are then inserted into the inlet and outlet PDMS ports to facilitate fluidic connections and pumping.

A blood sample is taken from a patient and enriched for potential CTCs using a commercially available microfluidic sorter (Parsortix, Angle plc) and eluted per manufacturer's protocol. Eluted cells are cultured and cell cycle arrested. Cells are stained using a mixture of Alexa 488 labelled anti Cytokeratin antibody, Alexa594 labelled anti CD45 antibody, and DAPI, and harvested.

The fluidic device is mounted on a holder allowing for interfacing with fluidic tubing for solution exchange within the device and an optical microscope for interrogation. Fluorescence imaging is performed using an inverted microscope equipped with a 60×/1.00 water immersion objective and an SCMOS camera. The temperature inside the device is controlled by a heater held in contact with the backside of the device.

Prior to receiving the cells, the device is flushed by 1% sodium dodecyl sulfate, buffer solution (0.5 TBE, 3% b-mercaptoethanol (BME) and 0.5% Triton X-100) and BSA at 1 mg/mL for 10 minutes.

The stained cells are introduced through the inlet port into the fluidic device and flowed along the primary channel (610) using pressure driven flow. Cells are individually inspected in the intersection region (606) by stopping the flow upon detection of the cell with brightfield microscopy. The cell is then imaged for all three fluorophores and CTC candidates are selected for fixing in gel based on fulfillment of all three criteria: (a) presence of a nucleus (b) positive for Cytokeratin and (c) negative for CDC45. If the cells fails the criteria, the flow is resumed and another cell is flowed into the intersection region for examination.

Next, once a CTC candidate cell has been found, an alkaline lysing solution is flowed along the secondary channel (605) and through the intersection region (606), which lyses the cell and releases the metaphase chromosomes. Once released, the chromosomes are maintained in the intersection region by the pillars, while the lysed cell debris is filtered out. Next the chromosomes are prepared for fixing in gel by flowing proteinase K and RNase for digestion, and YOYO-1 to stain the chromosomes (all reagents from Thermo Fisher) through the secondary channel at a rate of 1-10 microns/sec. All digested molecules, non-chromosome nucleic acid material, and excess reagent is filtered through the pillars, maintaining the chromosomes stripped of protein in the intersection region. The stained chromosomes are then interrogated by the interrogation system to monitor their swelling over a period of 30 minutes at 37 degrees Celsius, during which time the chromosomes swell to a length approximately 10 times their original length. In addition, during this time the non-reagent buffer solution is occasionally flowed in an oscillatory manner through the secondary channel, in coordination and control of the interrogation system, to gently disperse the chromosomes within the intersection region.

Next, a solution of 1.5% (w/w) low-gelling agarose (Agarose Type IX, Sigma-Aldrich) is flowed through the secondary channel, displacing the previous solution, and immersing the chromosomes in the gel solution in the intersection region, and then the device was placed at 4° C. for 30 minutes to ensure agarose gelation. With chromosomes fixed in the gelled agarose, the PDMS lid is then removed, exposing the fixed chromosomes in a porous gel, contained within the channel, less than 5 microns from the surface, swelled along a 2D plane.

In this state, the chromosomes are easily accessible to a variety of different in-situ labeling and image protocols.

Example 2: Creating a DNA Library from a Portion of a Single Human Chromosome Observed to have Abnormal Banding Patterns A blood sample is taken from a human patient, cell cycle synchronized with methotrexate, released with thymidine, arrested with Colcemide, swollen in a hypotonic solution, and dropped onto a well with polypropylene walls and a 170 um coverglass bottom (801) to yield prometaphase chromosomes spreads (802). Slides are G banded and placed into an inverted Nikon TE2000 microscope. The microscope is equipped with a UV light engine (Young Optics NVR Plus DLP UV Engine) customized to image a digital mirror device at the sample.

A photodegradable hydrogel is polymerized on top of the sample (803) by mixing poly(ethylene glycol)-di(photolabile acrylate) (PEG-DPA) and ammonium persulfate (APS) and tetramethylethylenediamine (TEMED) as redox initiator and catalyst. The solution is immediately pipetted onto the glass and allowed to cure for 30 minutes at room temperature. The fluidic well is subsequently washed 5 times with 20 ul of 25 mM MES pH 5.8.

Using a 638 nm LED as a light source, brightfield images of banded chromosomes are acquired and the labeling pattern compared with a table of G banding patterns. A chromosomal insertion is identified on a single sister chromatid of chromosome 17 at location 17p5, and a decision is made to excise it for further analysis.

The operator traces a box around an image of the chromosome using custom written software on a control computer. When the box is finished, the computer scales and translates the box coordinates into a binary mask pattern and programs the DLP chip with the pattern before turning on a 385 nm LED and irradiating the region of the chromosome (804). This photodegrades the region of the hydrogel in close proximity to the chromosome (805).

The control computer directs a robotic pipette tip to perform 2 washes with 20 ul NEBuffer r2.1, then adds EcoRI and trypsin in NEBuffer r2.1 and incubates at 37 C for 10 mins. This digests (807) the protein portions of the chromatin and chops the exposed DNA (806) into small pieces (808). The sample is then aspirated and transferred (809) to a microcentrifuge tube and the device washed with 20 ul additional NEBuffer r2.1, which is pooled with the first aspirate. The sample is then used to construct a DNA sequencing library using Ultra II DNA Library Prep Kit (NEB).

Example 3: Cleavable Proximity Barcoded Crosslinker

As an initial proof of concept, we here describe an example method of using a Cleavable Proximity Barcoded Crosslinker (CPBC). In this example, the CPBC consists of two capture probes, each of which consists of a capture domain consisting of Psoralen group attached to a double-strand nucleic acid barcode 15 base-pairs in length, wherein the two capture probes have identical barcodes. The two capture probes are then connected to each through a cleavable linker comprising a double stranded nucleic acid that includes a PAM sequence followed by a 20 base pair length recognition segment that can be recognized by a specifically designed guide RNA to activate a cleave when used as part of a CRISR-Cas9 system. All CPBCs are manufactured to ensure that the CPBCs have unique barcodes from each other, and that the CPBCs share the same recognition segment in their cleavable linker region.

A sample comprised of suspended human metaphase blood cells in solution are exposed to CPBCs and UV radiation for 30 minutes to initiate cross-linking of the Psoralen and the nucleic acid contained within the cell's chromosomes. After cross-linking, the cells are lysed, and the proteins are digested. The CPBCs are cleaved via recognition of the recognition segment by the CRISP-Cas9 system, separating the capture probes from each other. The long nucleic acid molecules with bound capture probes are then purified in low melting point agarose plugs [Zhang, 2012]. The sample is electroeluted into low salt denaturing buffer (0.1×TBE, 20 mM NaCl, 2% beta-mercaptoethanol) with YOYO-1 at a ratio of 1 dye per 10 nucleotide pairs and incubated at 18C overnight. The sample is diluted 1:1 with formamide with minimal manipulation and heated to 31C for 10. minutes [Tegenfeldt, 2009, 10,434,512] before quenching on ice to generate a AT/CG density physical map of YOYO-1 along the length of the long nucleic acid molecules.

Long nucleic acid molecules are then combed on a surface by dispensing the solution of DNA onto silanized glass while maintained at a 45 degree angle, allowing the trailing meniscus of the solution to attach the long nucleic acid molecule ends to the hydrophobic glass surface. The long nucleic acid molecules are then interrogated with a fluorescent imaging system to generate an in-silico representation of the molecule's physical map, which is then compared with pre-computed reference physical maps that are derived from sequences of the human genome assembly GRCh37 analyzed for melting state by the method of [Tostesen, 2005].

What is claimed is:

1. A method of tracking proximity relationships comprising: (a) introducing a body into a solution of bio-molecule(s), said body comprising at least two capture probes, wherein each capture probe comprises a barcode and a capture domain, and at least one capture probe is a releasable capture probe, connected to the body via at least one cleavable linker; (b) allowing at least two capture probes to bind to their respective target bio-molecule(s) via their respective capture domains; and (c) releasing the at least one releasable capture probe from the body by cleaving its at least one cleavable linker.

2. The method of claim 1, wherein at least one capture domain within the body non-specifically binds to a nucleic acid.

3. The method of claim 1, wherein at least one capture domain within the body specifically binds to a nucleic acid having a specific nucleic acid sequence.

4. The method of claim 1, wherein at least one capture domain within the body specifically binds to a specific protein.

5. The method of claim 1, wherein at least one capture domain within the body non-specifically binds to a protein.

6. The method of claim 1, wherein at least one capture domain within the body binds to an available target bio-molecule when subjected to activation.

7. The method of claim 1, wherein at least one capture domain is caged by a photolabile protecting group.

8. The method of claim 1, wherein at least one capture probe from a first body binds to the bio-molecule, and at least one capture probe from a second body also binds to the same bio-molecule.

9. The method of claim 1, wherein at least one releasable capture probe from a first body binds to the bio-molecule, and after said releasable capture probe is released from the first body, at least one capture probe from a second body also binds to said bio-molecule.

10. The method of claim 1, wherein the body comprises a bead, to which all capture probes are connected to through cleavable linkers.

11. The method of claim 10, wherein the bead is a dendrimer.

12. The method of claim 1, wherein the at least one bound bio-molecule is a double strand nucleic acid of at least 1 kbp in length.

13. The method of claim 12, wherein said double strand nucleic acid of at least 1 kbp in length comprises a higher order nucleic acid structure.

14. The method of claim 12, wherein at least a portion of the double strand nucleic acid of at least 1 kbp in length is further processed.

15. The method of claim 14, wherein the processing comprises generating a physical map.

16. The method of claim 14, wherein the processing comprises sequencing.

17. The method of claim 14, wherein the processing comprises hybridization of a nucleic acid molecule.

18. The method of claim 14, wherein the processing comprises amplification of at least a portion of a nucleic acid.

19. The method of claim 14, wherein the processing comprises an enzymatic reaction.

20. The method of claim 14, wherein the processing comprises an incorporation of a nucleotide using a polymerase.

* * * * *